(12) United States Patent
Ndao et al.

(10) Patent No.: US 8,043,825 B2
(45) Date of Patent: Oct. 25, 2011

(54) SERUM BIOMARKERS FOR CHAGAS DISEASE

(75) Inventors: Momar Ndao, La Prairie (CA); Brian Ward, Montreal (CA); Rebecca Caffrey, Mountain View, CA (US); Terence William Spithill, Notre Dame D'lle Perrot (CA); Hongshan Li, West Roxbury, MA (US); Vladimir Podust, Fremont, CA (US); Regis Perichon, Media, PA (US)

(73) Assignee: McGill University, Montreal (CA)

( * ) Notice: Subject to any disclaimer, the term of this patent is extended or adjusted under 35 U.S.C. 154(b) by 129 days.

(21) Appl. No.: 11/006,119

(22) Filed: Dec. 6, 2004

(65) Prior Publication Data

US 2005/0260691 A1    Nov. 24, 2005

Related U.S. Application Data

(60) Provisional application No. 60/625,519, filed on Nov. 6, 2004, provisional application No. 60/565,093, filed on Apr. 22, 2004, provisional application No. 60/527,153, filed on Dec. 5, 2003.

(51) Int. Cl.
 *G01N 33/53* (2006.01)
 *G01N 33/569* (2006.01)
 *G06F 19/00* (2011.01)

(52) U.S. Cl. .................................. 435/7.22; 702/19
(58) Field of Classification Search .................. None
 See application file for complete search history.

(56) References Cited

U.S. PATENT DOCUMENTS

| | | | |
|---|---|---|---|
| 4,705,751 A * | 11/1987 | Mosher ...................... 435/70.4 |
| 5,281,522 A | 1/1994 | Senyei et al. |
| 5,719,060 A | 2/1998 | Hutchens et al. |
| 5,786,156 A | 7/1998 | Taddei-Peters et al. |
| 6,030,835 A * | 2/2000 | Musser et al. ............... 435/340 |
| 6,107,045 A | 8/2000 | Koren et al. |
| 6,156,546 A * | 12/2000 | Konkel et al. ............... 435/91.2 |
| 6,225,047 B1 | 5/2001 | Hutchens et al. |
| 6,675,104 B2 | 1/2004 | Paulse et al. |
| 7,094,549 B2 * | 8/2006 | Jackowski et al. ............ 435/7.1 |
| 7,605,003 B2 * | 10/2009 | Chan et al. ................... 436/178 |
| 2003/0054367 A1 * | 3/2003 | Rich et al. ....................... 435/6 |
| 2003/0078192 A1 * | 4/2003 | Winter et al. .................... 514/2 |
| 2003/0108960 A1 | 6/2003 | Zrein |
| 2004/0096917 A1 * | 5/2004 | Ivey et al. .................... 435/7.32 |
| 2005/0048519 A1 * | 3/2005 | Chien et al. ...................... 435/6 |

(Continued)

FOREIGN PATENT DOCUMENTS

WO    WO 99/41610    8/1999

(Continued)

OTHER PUBLICATIONS

Ouaissi, All et al, European Journal of Cell Biology, v. 59, 1992, p. 68-79.*

(Continued)

*Primary Examiner* — Albert Navarro
*Assistant Examiner* — Ginny Portner
(74) *Attorney, Agent, or Firm* — Dowell & Dowell, P.C.

(57) ABSTRACT

The present invention provides protein-based biomarkers and biomarker combinations that are useful in qualifying Chagas disease status in a patient. In particular, the biomarkers of this invention are useful to classify a subject sample as infected with Chagas disease or non-infected. The biomarkers can be detected by SELDI mass spectrometry.

24 Claims, 36 Drawing Sheets

MW: 9.3 F1WL

U.S. PATENT DOCUMENTS

| | | | | |
|---|---|---|---|---|
| 2005/0187159 | A1* | 8/2005 | Bridon et al. | 514/12 |
| 2006/0253259 | A1* | 11/2006 | Fernandez | 702/19 |
| 2007/0031832 | A1* | 2/2007 | Watt et al. | 435/6 |
| 2009/0042229 | A1* | 2/2009 | Folkman et al. | 435/23 |

FOREIGN PATENT DOCUMENTS

| | | | |
|---|---|---|---|
| WO | 03/046569 | * | 6/2003 |

OTHER PUBLICATIONS

Lohr et al, Blood, vol. 76(10) Nov. 15, 1990, pp. 2117-2224, The amino terminal 29- and 72-Kd fragments of Fibronectin Mediate Selective Monocyte recruitment.*

Quade, Bradley J. et al, The Journal of Biological Chemistry, vol. 263(36), Dec. 25, 1988, pp. 19602-19609, Fibronectin's amino terminal matrix assembly site is located within the 29 kDa Amino-terminal domain containing Five Type I repeats.*

Andrade, Sonia et al, Am. J. Trop. Med. Hyg., vo. 40(3), pp. 252-260, 1989Sequential changes of the connective matrix components of the myocardium (Fibronectin and Laminin) and evolution of cardiac fibrosis in mice infected with *Trypanosoma cruzi*.*

Garcia-Pardo, Angeles et al, The Journal of Biological Chemistry, vol. 260(18) Aug. 25, 1985, pp. 10320-10325, Primary structure of Human Plasma Fibronectin.*

Grijalva, Mario Javier, Ph.D., 1997, Immunological characterization of the antigen released in vitro by *Trypanosma cruzi* infected cells and determination of the risk of transfusion-associated transmission of Chagas disease in Ecudor. vol. 58/09-B of Dissertation Abstracts International, p. 4598, Ohio University, 141 pages, Abstract only.*

Truyens, Carine et al, Experimental Parasitology, vol. 80, pp. 499-506, 1995, High Circulating levels of Fibronectin and antibodies against its RGD adhesin site during Mouse *Trypanosoma cruzi* infection: relation to survival.* dos Santos, Paula V.A. e tal, Microbes and Infection, vol. 3, pp. 971-981, 2001, Prevalence of CD8+ alpha/Beta T cells in *Trypanosoma cruzi*-elicited myocarditis is associated with acquisition of CD62Llow LFA-1highVLA-4High activation phenotype and expression of IFN-gamma inducible adhesion and chemoattractant molecules.*

Noisin, EL et al, Infection and Immunity, vol. 57(4), p. 1030-1034, Apr. 1989, Fibronectin increases *Trypanosoma cruzi* Amastigote binding to and uptake by Murine Macrophages and Human monocytes.*

Chiller, TM et al, Am. J. Trop. Med. Hyg. vol. 43(6), pp. 650-656, Igg antibody reactivity with *Trypanosoma crugzi* and *Leishmania* antigens in sera of patients with Chagas disease and Leishmaniasis.*

Mendes, Rodolfo P. et al, Journal of Clinical Microbiology, vol. 35(7), Jul. 1997, pp. 1829-1834, Serological Diagnosis of Chagas' Diease: a Potential Confimatory Assay using perserved protein antigens of *Trypaosoma cruzi*.*

Ferreira, Marcelo S e tal, Clinical Infectous Diseases, vol. 25(6), Dec. 1997, pp. 1397-1400, Reactivation of Chagas Disease in Patients with AIDS: Report of three new cases and Review of the Literature.*

Ndao, M. et al, Journal of clinical microbiology, Apr. 2010, pp. 1139-1149, vol. 48, No. four, Identification of novel diagnostic serum biomarkers for Chagas' disease in asymptomatic subjects by mass spectrometric profiling.*

Cano, R. et al. "Levels of Apolipoproteins and Cholesterol of Low and High Density Lipoproteins in Asymptomatic Chagas Disease." *Medicina* (Buenos Aires), 45(3):269-272 (1985).

dos Santos, P. V. A. et al. "Prevalence of $CD84^+\alpha\beta$ T cells in *Trypanosoma cruzi*-elicited myocarditis is associated with acquisition of $CD62L^{Low}LFA-1^{High}VLA-4^{High}$ activation phenotype and expression of IFN-γ-inducible adhesion and chemoattractant molecules." *Microbes and Infection*, vol. 3, pp. 971-984 (2001).

Marino, A.P.M.P. at al. "*Trypanosoma cruzi* infection: a continuous invader-host cell cross talk with participation of extracellular matrix and adhesion and chemoattractant molecules." *Braz J Med Biol Res*, 36(8):1121-1133 (2003).

Scharfstein, J. et al. "Induction of the Acute-Phase Protein Serum Amyloid P in Experimental Chagas' Disease." *Infection and Immunity*, 35(1):46-51 (Jan. 1982).

Araújo-Jorge et al., "Implication of transforming growth factor-beta1 in Chagas disease myocardiopathy", *J Infect Dis.* Dec. 15, 2002;186(12):1823-8.

Avila et al., "Antibodies to Laminin in American Cutaneous Leishmaniasis," *Infect Immun.* Jan. 1984; 43(1): 402-406.

Cotta-De-Almeida et al., "*Trypanosoma cruzi* infection modulates intrathymic contents of extracellular matrix ligands and receptors and alters thymocyte migration," *Eur J Immunol.* Sep. 2003;33(9):2439-48.

Magalhaes,-Santos et al., "Fibrogenesis and collagen resorption in the heart and skeletal muscle of *Calomys callosus* experimentally infected with *Trypanosoma cruzi*: immunohistochemical identification of extracellular matrix components," *Mem Inst Oswaldo Cruz.* Jul. 2002;97(5):703-10.

Pestel et al., "Polyclonal cell activity of a repeat peptide derived from the sequence of an 85-kilodalton surface protein of *Trypanosoma cruzi* trypomastigotes," Infect Immun. Feb. 1992; 60(2): 715-719.

Truyens et al., "High circulating levels of fibronectin and antibodies against its RGD adhesion site during mouse *Trypanosoma cruzi* infection: relation to survival," May 1995;80(3):499-506.

European Supplementary Search Report, European Application No. 04813321.9, Jan. 28, 2009, 3 pages.

Ouaissi, A. et al., "Fibronectin Cleavage Fragments Provide a Growth Factor-Like Activity for the Differentiation of *Trypanosoma cruzi* Trypomastigotes to Amastigotes," European Journal of Cell Biology, 1992, pp. 68-79, vol. 59, No. 1.

Poon, T.C.W. et al., "Comprehensive Proteomic Profiling Identifies Serum Proteomic Signatures for Detection of Hepatocellular Carcinoma and Its Subtypes," Clinical Chemistry, American Association for Clinical Chemistry, May 1, 2003, pp. 752-760, vol. 49, No. 5.

Thulasiraman, V. et al., "Detection and Identification of Virulence Factors in *Yersinia pestis* Using SELDI Proteinchip® System," Biotechniques, Informa Life Sciences Publishing, Feb. 1, 2001, pp. 428-432, vol. 30, No. 2.

European Patent Office Communication, European Patent Application No. EP 04813321.9, Aug. 24, 2010, six pages.

Rivarola, H.W. et al., "*Trypanosoma cruzi* Trypanothione Reductase Inhibitors: Phenothiazines and Related Compounds Modify Experimental Chagas Disease Evolution," *Current Drug Targets—Cardiovascular & Haematological Disorders*, 2002, vol. 2, No. 1, pp. 43-52.

Vartio, T. et al., "Monoclonal Antibody Against the N-terminal End of Human Plasma Fibronectin," *Biochem. J.*, 1983, vol. 215, pp. 147-151.

European Examination Report, European Application No. 04813321.9, Apr. 27, 2009, 7 pages.

* cited by examiner

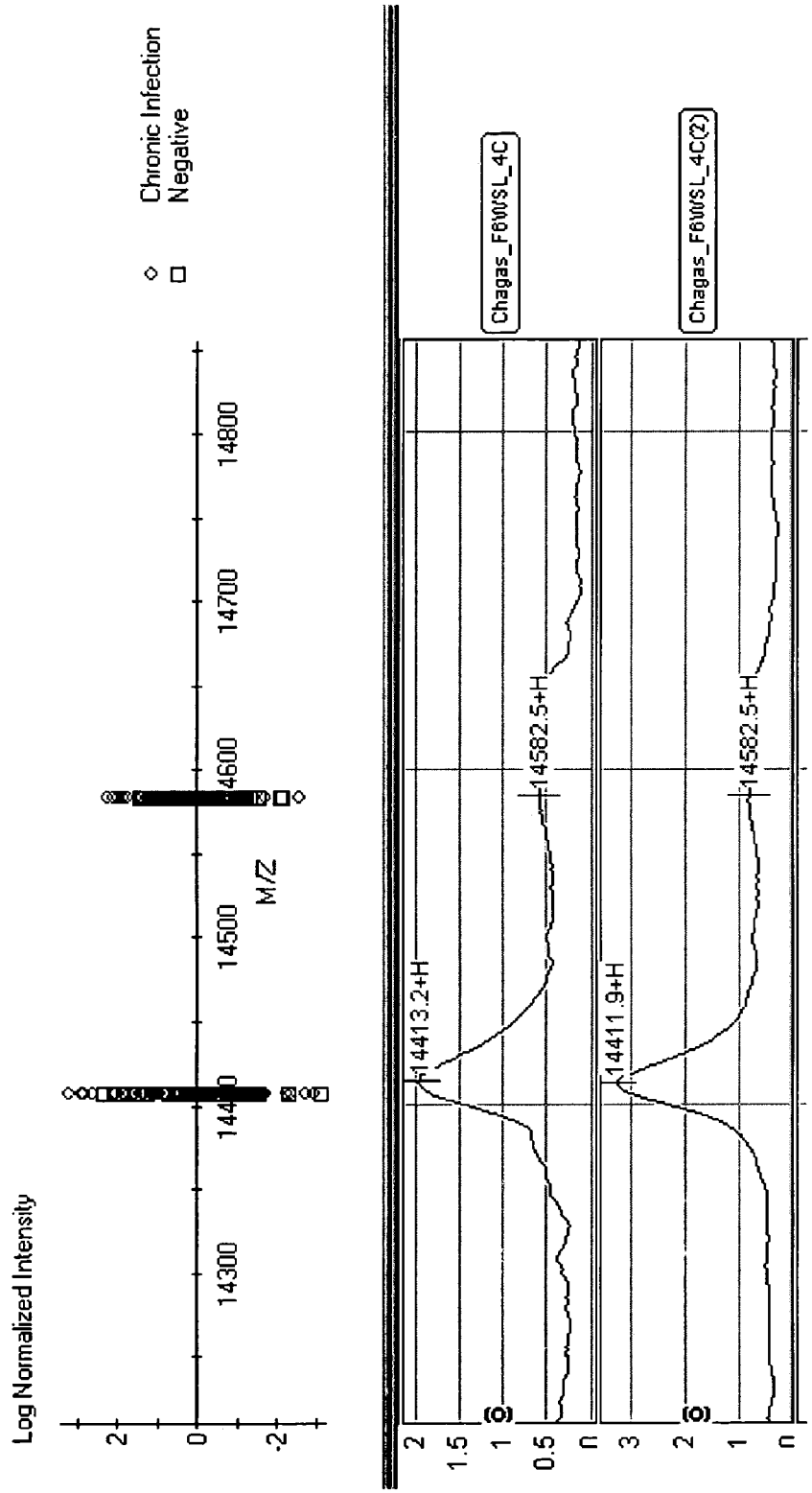

Chagas Venezuela vs Guatemala EKG+ F1WL, MW: 8.127 kDa (Apo-1) P

SERUM BIOMARKERS FOR CHAGAS DISEASE

CROSS-REFERENCE TO RELATED APPLICATIONS

This application claims the benefit of U.S. provisional patent application No. 60/527,153, filed Dec. 5, 2003; U.S. provisional patent application No. 60/565,093, filed Apr. 22, 2004; and U.S. provisional patent application No. 60/625,519, filed Nov. 6, 2004, the disclosure of each of which is incorporated herein by reference in its entirety for all purposes.

BACKGROUND OF THE INVENTION

American trypanosomiasis (Chagas disease) is a protozoan infection caused by the flagellate *Trypanosoma (Schizotrypanum) cruzi*, widespread in the Americas, and endemic to Central and South America. Chagas disease can be quickly fatal, especially in children, or it can be carried asymptomatically for decades. Between 10-30% of infected people eventually develop severe cardiac or digestive chronic involvement as late manifestations of Chagas disease. These complications are usually fatal. In the Americas, approximately 16-18 million people are estimated to be infected by the parasite. This estimate does not include Mexico and Nicaragua, for which accurate public health data are not available.

Due to recent patterns of urbanization and immigration, Chagas disease is no longer a unique problem for Latin American countries. Estimates a decade ago suggested that approximately 300,000 infected individuals were living in the city of São Paulo, and more than 200,000 in Rio de Janeiro and Buenos Aires. In addition, Chagasic patients with chronic and asymptomatic forms of the disease are immigrating northward to the USA and Canada, and even eastward to Europe. Several years ago it was estimated that around 100,000 infected individuals were already living in the USA, most of them having immigrated from Mexico and Central America. Many of these immigrants are unaware that they have contracted Chagas disease and continue to donate infected blood. Controlling "transfusional" Chagas disease is therefore of paramount importance in preventing infection in the USA and Canada.

Chagas disease may also be transmitted congenitally. Several American families never exposed by travel to endemic areas were congenitally infected by parents or grandparents from Central or South America. Programs in Central and South America are presently engaged in attempting to screen pregnant women and newborns to reduce the rate of congenital chagas.

Presently, no optimal test is available for the diagnosis of chronic-stage Chagas Disease. The most straightforward available method of excluding potentially infected donors from the blood pool is to ask questions about immigration and travel involving Central and South America. These geographic exclusions are somewhat insensitive and subject to the reliability of the potential donor. As a result, a large number of willing and healthy donors are inappropriately excluded, thus contributing to a blood donor shortage in Canada and the US. A quick, accurate, and inexpensive screening test is therefore needed to provide a rapid diagnosis of Chagas disease and to ensure the safety of blood supplies.

SUMMARY OF THE INVENTION

The present invention provides polypeptide-based biomarkers that are differentially present in subjects with Chagas disease, and particularly that are differentially present in chronically infected subjects versus uninfected healthy individuals. In addition, the present invention provides methods of using the polypeptide-based biomarkers to qualify Chagas disease in a subject or in a biological sample taken from a subject, including a sample of serum, blood or other donated tissue.

As such, the invention provides biomarkers that represent novel fragments of proteins expressed in infected individuals by *T. cruzi*, the pathogen responsible for Chagas disease. One such protein, referred to here as M110, is homologous to portions of a *Leishmania major* protein of unknown function (LM15-1.32). M110 and portions thereof provide useful biomarkers for Chagas disease.

In one aspect, the present invention provides a method for qualifying Chagas disease status in a subject, the method comprising: (a) measuring at least one biomarker in a biological sample from the subject, wherein the at least one biomarker is selected from the group consisting of the biomarkers of Table 1 and Table 2 (i.e., Tables 2A-2X) as well as those set forth in the figures; and (b) correlating the measurement with Chagas disease status. In one embodiment, the biological sample is a serum sample.

In one embodiment, the at least one biomarker is selected from the group consisting of the biomarkers of Tables 3 and 4. In another embodiment, the at least one biomarker is selected from the following biomarkers: MIP-1a, Apo 1A, Fibronectin, C3 anaphylatoxin and M110. In another embodiment, the method comprises measuring each of the following biomarkers: MIP-1a, Apo 1A, Fibronectin, C3 anaphylatoxin and M 110. In yet another embodiment, the method further comprises additionally measuring one or more of any of the biomarkers listed in Table 1, Table 2 and in the figures. In a preferred embodiment, highly sensitive biomarkers of molecular masses 4.4, 4.8, 7.8, 8.9, 9.3, 13.6, 16.3, 28.7, and 54.04 are utilized.

In one embodiment, the at least one biomarker is measured by capturing the biomarker on an adsorbent of a SELDI probe and detecting the captured biomarkers by laser desorption-ionization mass spectrometry. In certain embodiments, the adsorbent is a cation exchange adsorbent, whereas in other embodiments, the adsorbent is a metal chelation adsorbent. In another embodiment, the at least one biomarker is measured by immunoassay.

In another embodiment, the correlating is performed by a software classification algorithm. In a further embodiment, the Chagas disease status is selected from chronically infected versus uninfected. In yet another embodiments, the Chagas disease status is selected from chronically infected status versus acutely infected disease status, chronically infected asymptomatic status versus chronically affected with symptoms, or acutely infected status versus healthy uninfected status. In still another embodiment, the Chagas disease status is selected from Chagas versus healthy. In a preferred embodiment, the at least one biomarker is selected from the biomarkers of Table 3. In still another embodiment, the Chagas disease status is selected from Chagas versus non-Chagas. In a preferred embodiment, the at least one biomarker is selected from the biomarkers of Table 4. In another preferred embodiment, the at least one biomarker is selected from the biomarkers of molecular weight 8.351 kDa, 9.3 kDa, 7.3 kDa, 6.04 kDa, 4.4 kDa, 4.07 kDa and 5.1 kDa, as depicted in FIGS. 7-9.

In yet another embodiment, the method further comprises managing subject treatment based on the status. If the measurement correlates with Chagas disease, then managing subject treatment comprises administering to a patient drugs selected from a group consisting of, but not necessarily limited to, drugs such as nifurtimox, benznidazole or allopurinol.

In a further embodiment, the method further comprises measuring the at least one biomarker after subject management.

In another aspect, the present invention provides a method comprising measuring at least one biomarker in a sample from a subject, wherein the at least one biomarker is selected from the group consisting of the biomarkers set forth in Table 1 and Table 2 as well as in the figures. In one embodiment, the sample is a serum sample.

In one embodiment, the at least one biomarker is selected from the group consisting of the biomarkers of Tables 3 and 4. In another embodiment, the at least one biomarker is selected from the following biomarkers: MIP-1a, Apo 1A, Fibronectin, C3 anaphylatoxin and M110. In still another embodiment, the method comprises measuring each of the following biomarkers: MIP-1a, Apo 1A, Fibronectin, C3 anaphylatoxin and M110. In yet another embodiment, the method further comprises additionally measuring one or more of any of the biomarkers listed in Table 1, Table 2 and in the figures.

In one embodiment, the at least one biomarker is measured by capturing the biomarker on an adsorbent of a SELDI probe and detecting the captured biomarkers by laser desorption-ionization mass spectrometry. In certain embodiments, the adsorbent is a cation exchange adsorbent, whereas in other embodiments, the adsorbent is a metal chelation. In another embodiment, the at least one biomarker is measured by immunoassay.

In still another aspect, the present invention provides a kit comprising: (a) a solid support comprising at least one capture reagent attached thereto, wherein the capture reagent binds at least one biomarker from a first group consisting of the biomarkers set forth in Table 1, Table 2 and in the figures; and (b) instructions for using the solid support to detect the at least one biomarker set forth in Table 1, Table 2 and in the figures.

In one embodiment, the kit provides instructions for using the solid support to detect a biomarker selected from the biomarkers of Tables 3 and 4. In another embodiment, the kit provides instructions for using the solid support to detect a biomarker selected from the following biomarkers: MIP-1a, Apo 1A, Fibronectin, C3 anaphylatoxin and M110. In another embodiment, the kit provides instructions for using the solid support to detect each of the following biomarkers: MIP-1 a, Apo 1A, Fibronectin, C3 anaphylatoxin and M110. In yet another embodiment, the kit provides instructions for additionally measuring one or more of any of the biomarkers listed in Table 1, Table 2 and in the figures, preferably including one or more of the highly sensitive biomarkers of molecular masses 4.4, 4.8, 7.8, 8.9, 9.3, 13.6, 16.3, 28.7, and 54.04.

In another embodiment, the solid support comprising the capture reagent is a SELDI probe. In some embodiments, the capture reagent is a cation exchange adsorbent. In other embodiments, the kit additionally comprises (c) an anion exchange chromatography adsorbent. In other embodiments, the kit additionally comprises (c) a container containing at least one of the biomarkers of Table 1, Table 2 and in the figures, preferably including one or more of the highly sensitive biomarkers of molecular masses 4.4, 4.8, 7.8, 8.9, 9.3, 13.6, 16.3, 28.7, and 54.04.

In a further aspect, the present invention provides a kit comprising: (a) a solid support comprising at least one capture reagent attached thereto, wherein the capture reagent binds at least one biomarker from a first group consisting of the biomarkers set forth in Table 1, Table 2 and in the figures; and (b) a container comprising at least one of the biomarkers set forth in Table 1, Table 2 and in the figures.

In one embodiment, the kit provides instructions for using the solid support to detect a biomarker selected from the biomarkers of Tables 3 and 4. In one embodiment, the kit provides instructions for using the solid support to detect a biomarker selected from the following biomarkers: MIP-1a, Apo 1A, Fibronectin, C3 anaphylatoxin and M110. In still another embodiment, the kit provides instructions for using the solid support to detect each of the following biomarkers: MIP-1a, Apo 1A, Fibronectin, C3 anaphylatoxin and M110. In yet another embodiment, the kit provides instructions for additionally measuring one or more of any of the biomarkers listed in Table 1, Table 2 and in the figures.

In another embodiment, the solid support comprising the capture reagent is a SELDI probe. In some embodiments, the capture reagent is a cation exchange adsorbent or metal chelation adsorbent. In other embodiments, the kit additionally comprises (c) an anion exchange chromatography adsorbent.

In yet a further aspect, the present invention provides a software product, the software product comprising: (a) code that accesses data attributed to a sample, the data comprising measurement of at least one biomarker in the sample, the biomarker selected from the group consisting of the biomarkers of Table 1, Table 2 and in the figures; and (b) code that executes a classification algorithm that classifies the Chagas disease status of the sample as a function of the measurement.

In one embodiment, the classification algorithm classifies Chagas disease status of the sample as a function of the measurement of a biomarker selected from the biomarkers of Tables 3 and 4. In one embodiment, the classification algorithm classifies Chagas disease status of the sample as a function of the measurement of a biomarker selected from the group consisting of MIP-1a, Apo 1A, Fibronectin, C3 anaphylatoxin and M110. In still another embodiment, the classification algorithm classifies Chagas disease status of the sample as a function of the measurement of each of the following biomarkers: MIP-1a, Apo 1A, Fibronectin, C3 anaphylatoxin and M110. In yet another embodiment, the classification algorithm classifies the Chagas disease status of the sample as a function of the additional measurement one or more of any of the biomarkers listed in Table 1, Table 2 and in the figures. In yet another embodiment, the software classification algorithm classifies Chagas disease status of the sample as a function of the measurement of biomarkers including biomarkers F1WH__2, F4IH__4, F3WL__8, and F1IL__3 of Table 1.

In other aspects, the present invention provides purified biomolecules selected from the biomarkers set forth in Table 1, Table 2 and in the figures and, additionally, methods comprising detecting a biomarker set forth in Table 1, Table 2 and in the figures by mass spectrometry or immunoassay. In preferred embodiments of both of the foregoing aspects, the biomarker is selected from the biomarkers of Tables 3 and 4.

In yet another embodiment, the method further comprises testing and qualifying stocks of blood based on the status of blood which has been tested according to the methods described herein. If the measurements taken from blood samples correlate with Chagas disease, then the management of blood stocks comprises decontamination of the infected blood by treatment of the infected blood with purification agents available to one skilled in the art including, but not limited to, agents such as gentian violet, ascorbic acid, and aminoloquinolone WR6026. Alternatively, the infected blood may be discarded or destroyed and only stocks of blood which have not tested positively for Chagas disease are retained.

In another aspect, the present invention provides a method of measuring at least three biomarkers in a in a biological sample, wherein the at least three biomarkers are selected from the group consisting of the biomarkers of Table 1 and Tables 2A-2X. In a preferred embodiment, the at least three biomarkers are selected from the group consisting of the biomarkers of Tables 3 and 4. In yet another preferred embodiment, the at least three biomarkers are selected from the group consisting of MIP-1a, Apo 1A, Fibronectin, C3 anaphylatoxin and M 10. In yet another preferred embodiment, the at least three biomarkers are Apo1, Fibronectin and C3 anaphylatoxin. In yet another preferred embodiment, the at least three biomarkers are selected from the group including biomarkers F1WH_2, F4IH_4, F3WL_8 and F1IL_3 of Table 1.

In one aspect, the present invention provides a method for qualifying Chagas disease status in a subject in comparison to the status of a different parasitic disease (i.e., a non-Chagas parasitic disease), the method comprising: (a) measuring at least one biomarker in a biological sample from the subject, wherein the at least one biomarker specifically indicates the presence of Chagas disease and does not indicate the presence of a different parasitic infection; and (b) correlating the measurement with Chagas disease status in comparison to the status of a different parasitic infection. In one embodiment, the biological sample is a serum sample. In a preferred embodiment of this method, the at lest one biomarker is selected from the group of biomarkers of Table 4. In another preferred embodiment, the at least one biomarker is selected from the group of biomarkers of molecular masses 8.351 kDa, 9.3 kDa, 7.3 kDa, 6.04 kDa, 4.4 kDa, 4.07 kDa and 5.1 kDa, as depicted in FIGS. 7-9. In another preferred embodiment of this method, the parasitic infection comprises a kinetoplastidae infection. In still another preferred embodiment, the parasitic infection includes, but is not limited to, Leishmaniasis, African trypanosomiasis (sleeping sickness), malaria and babesiosis.

In another aspect, the present invention provides a method for monitoring the course of progression of Chagas disease in a patient comprising: (a) measuring at least one biomarker in a first biological sample from the patient, wherein the at least one biomarker specifically indicates the presence of Chagas disease; (b) measuring the at least one biomarker in a second biological sample from the subject, wherein the second biological sample was obtained from the subject after the first biological sample; and (c) correlating the measurements with the progression or regression of Chagas disease in the subject. In one embodiment, the at least one biomarker is selected from the group consisting of the biomarkers of Tables 1 and 2 and, preferably, of Tables 3 and 4. In another preferred embodiment, the at least one biomarker is selected from the group consisting of 8.127 kDa (Apo-1) and 8.937 kDa.

Other features, objects and advantages of the invention and its preferred embodiments will become apparent from the detailed description, examples and claims that follow.

DETAILED DESCRIPTION OF THE INVENTION

Introduction

Figure 1A:
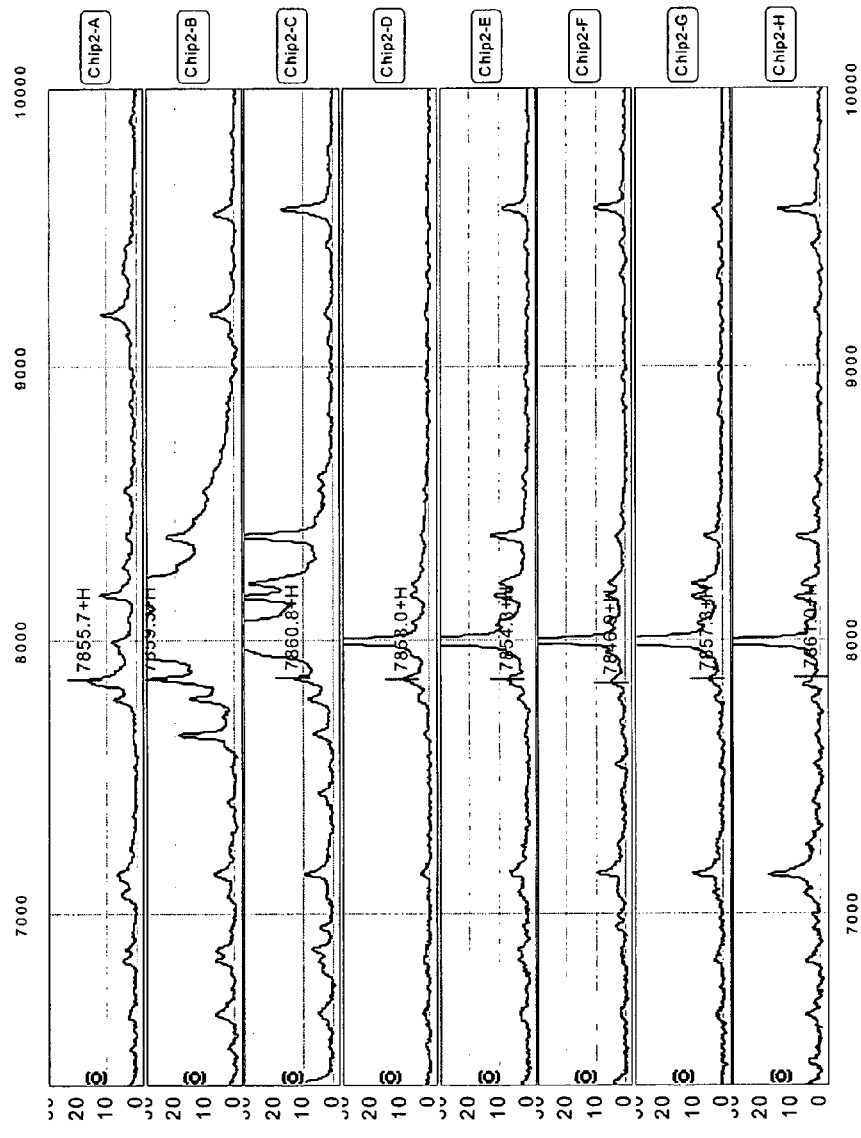
FIG. 1A-W shows representative mass spectra displaying several biomarkers of the invention and providing their mass-to-charge ratio.
Figure 1B:
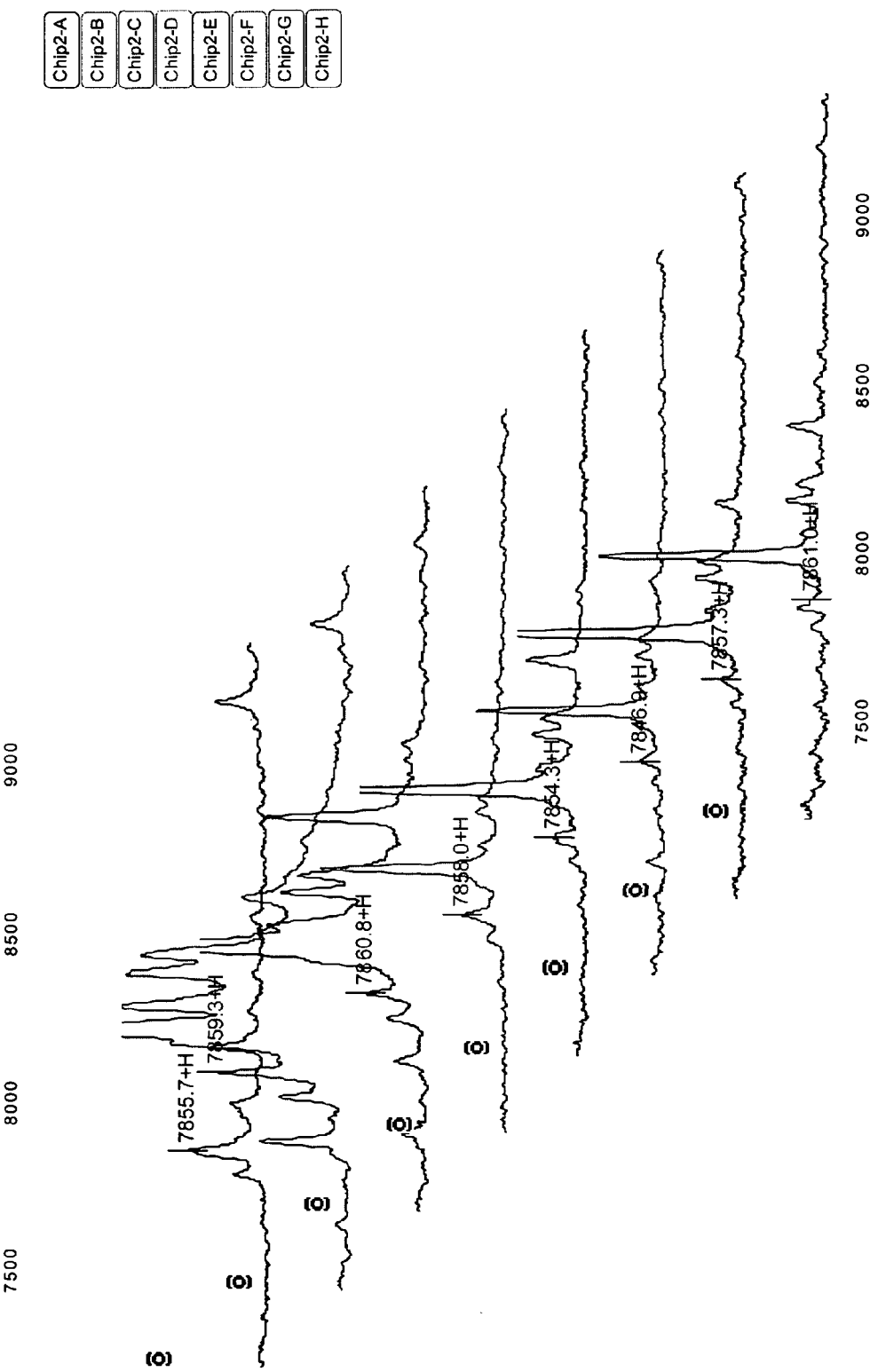
Figure 1C:
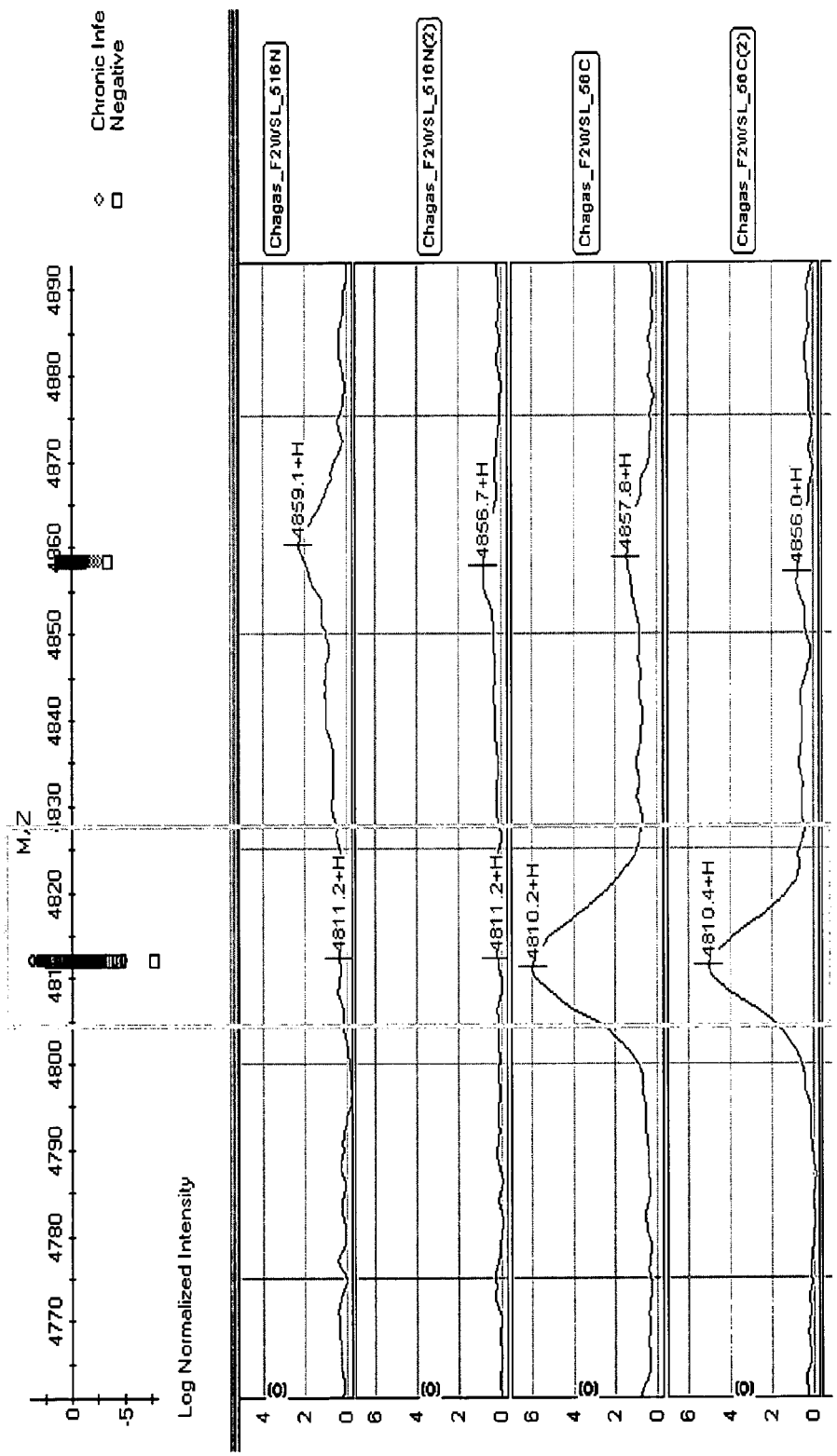
Figure 1D:
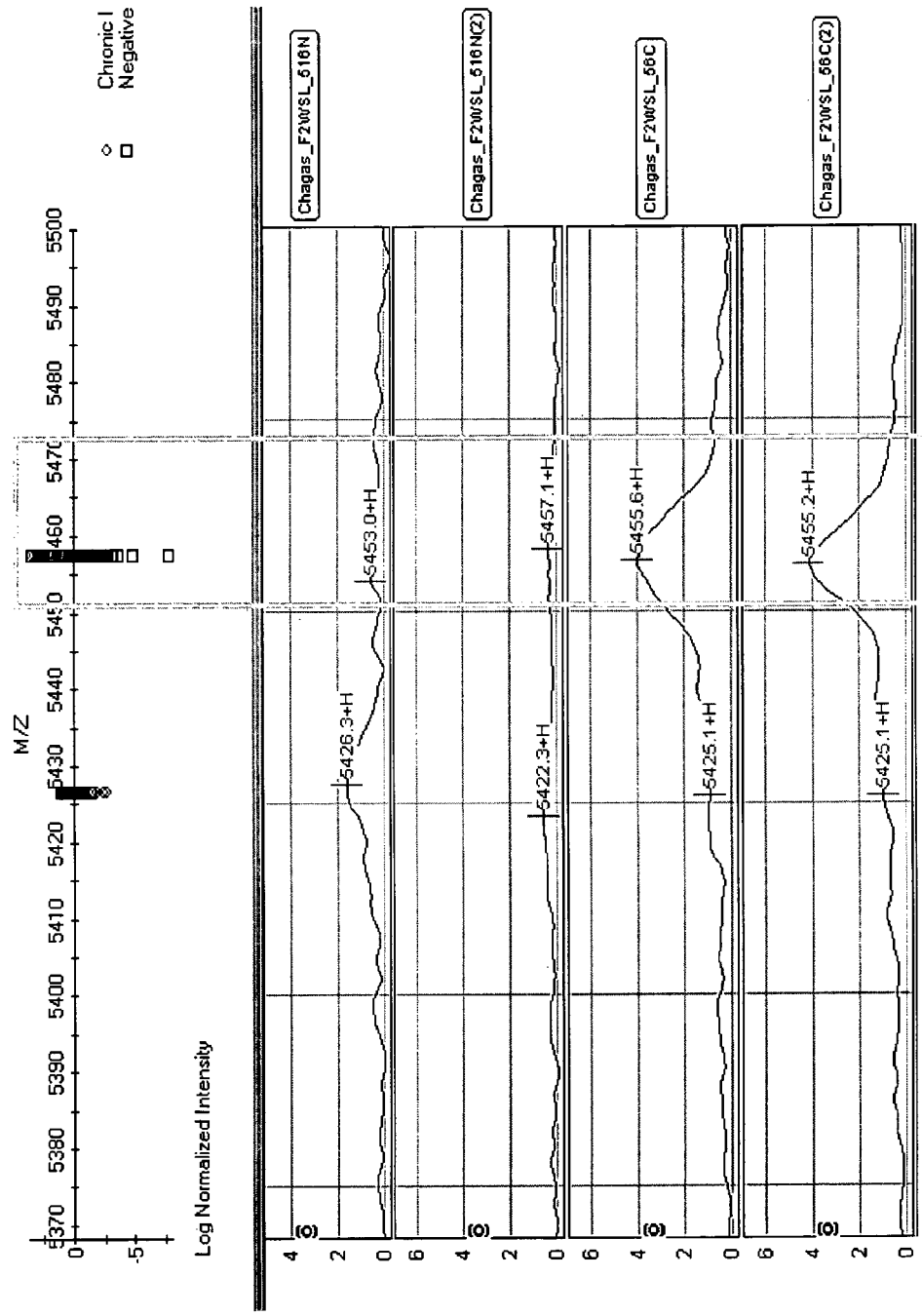
Figure 1E:
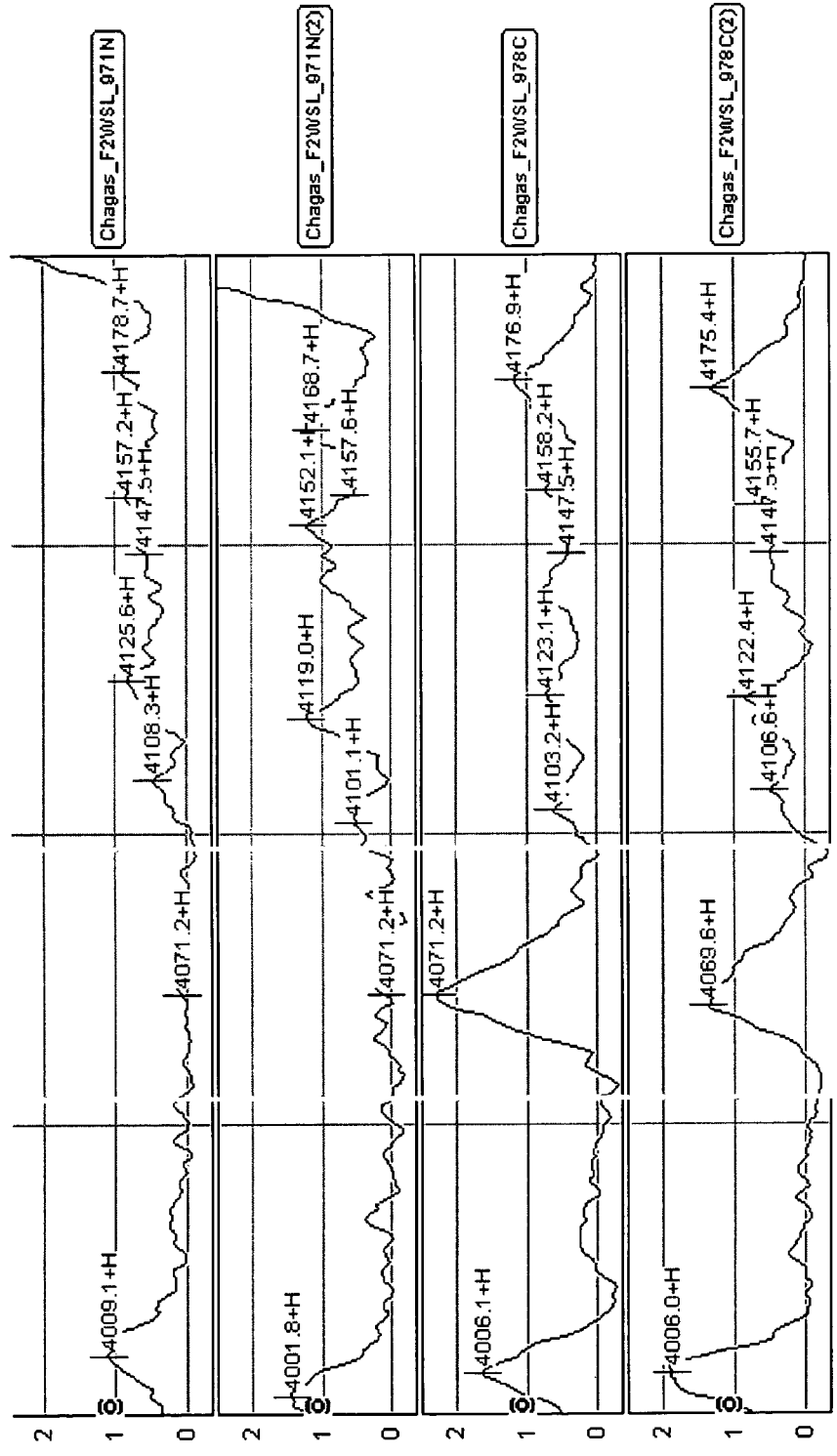
Figure 1F:
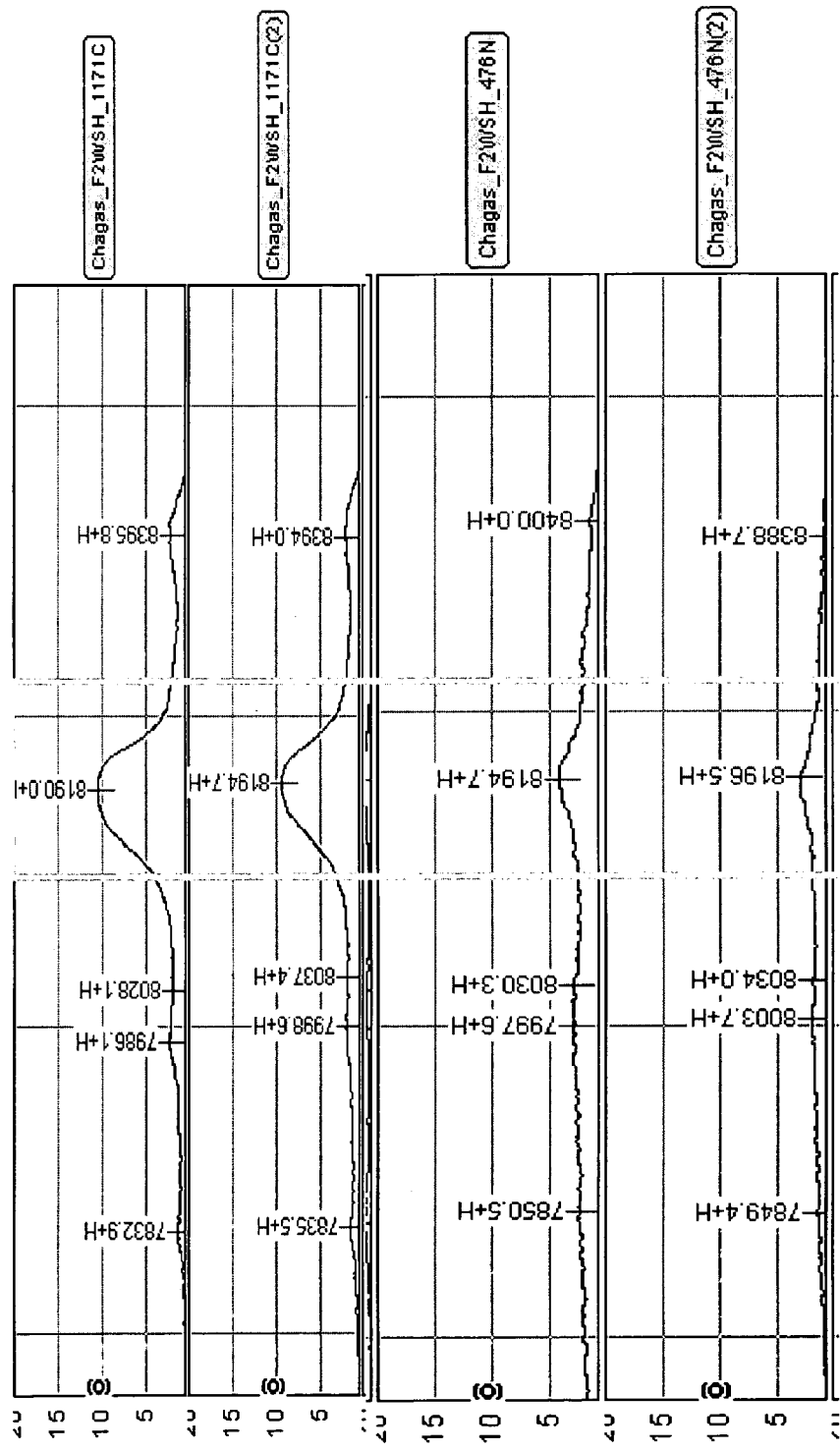
Figure 1G:
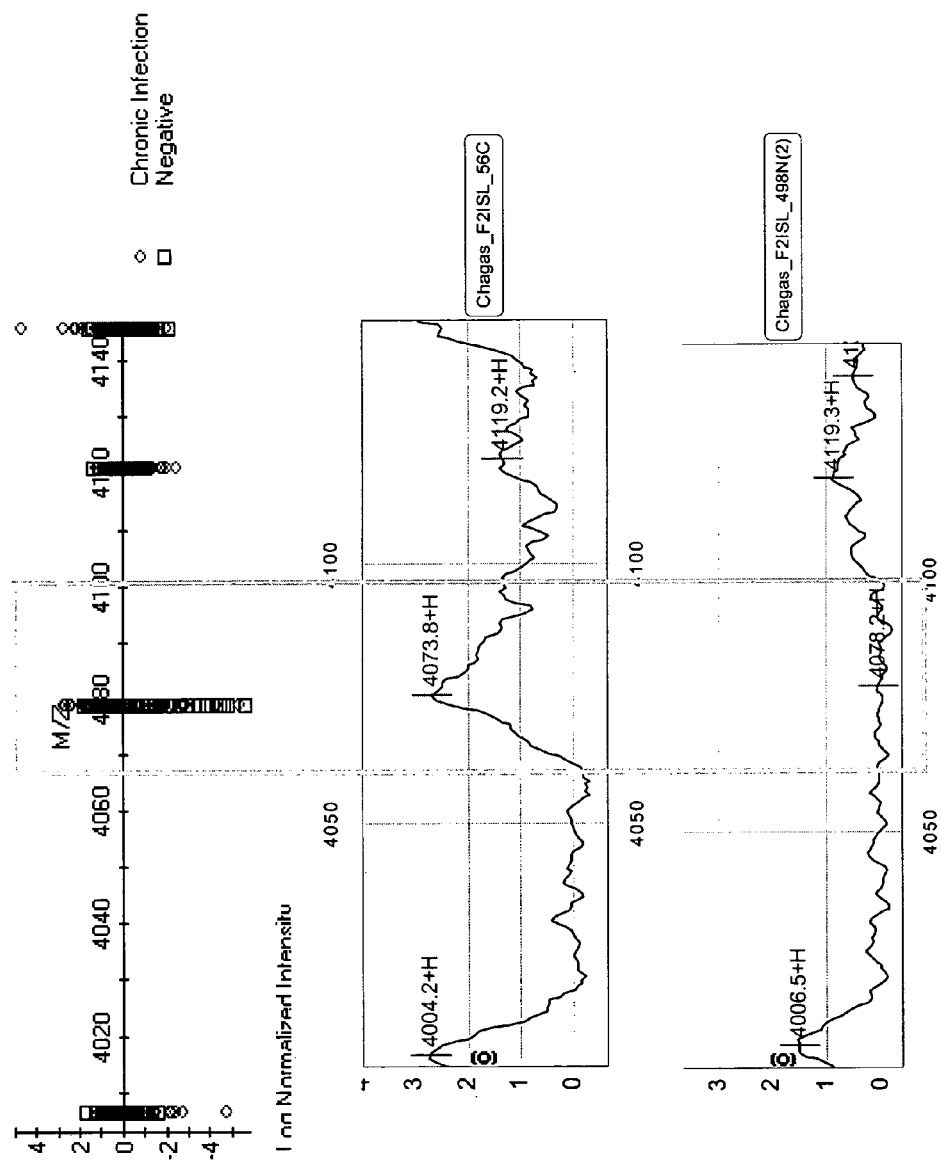
Figure 1H:
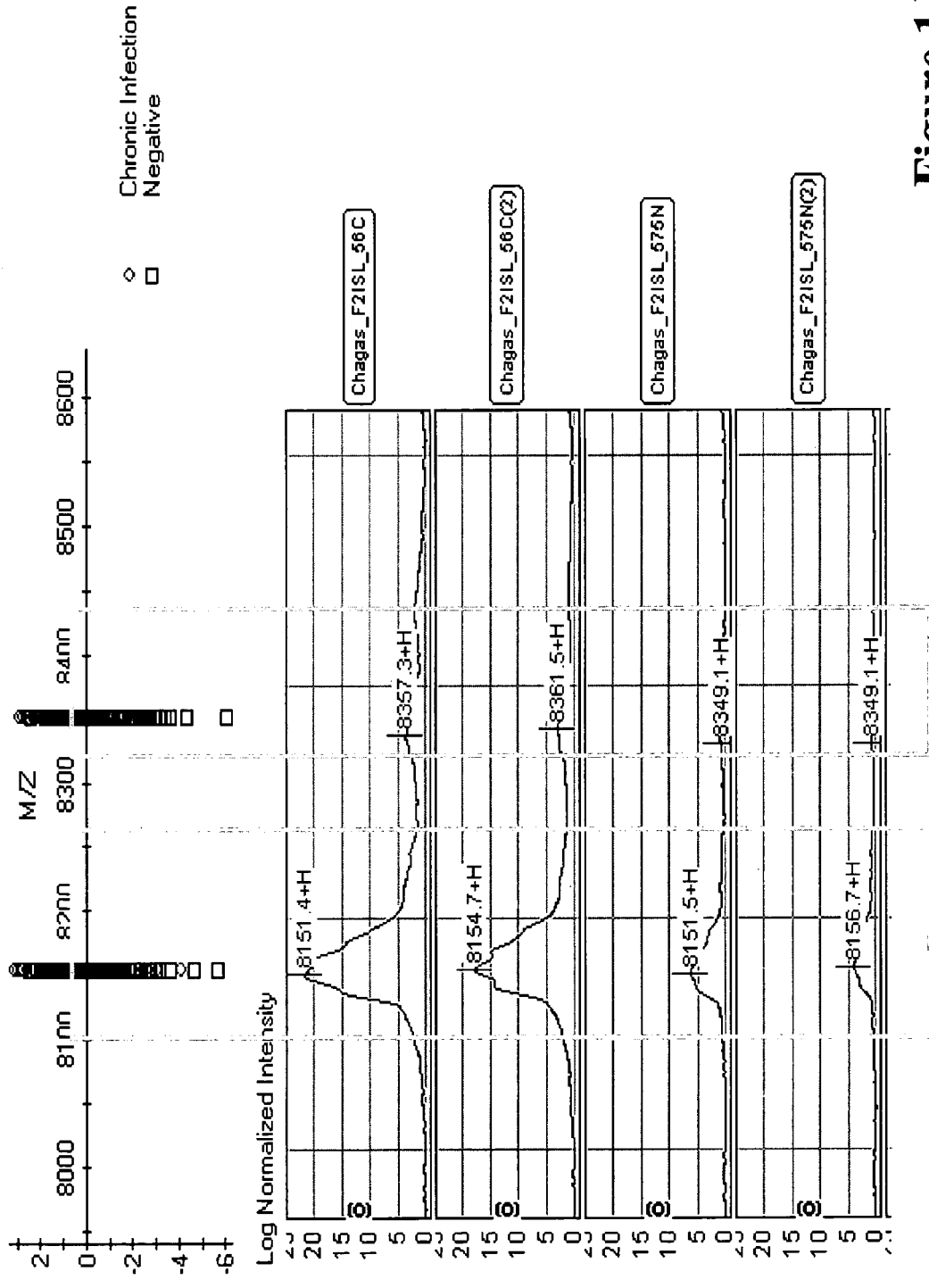
Figure 1I:
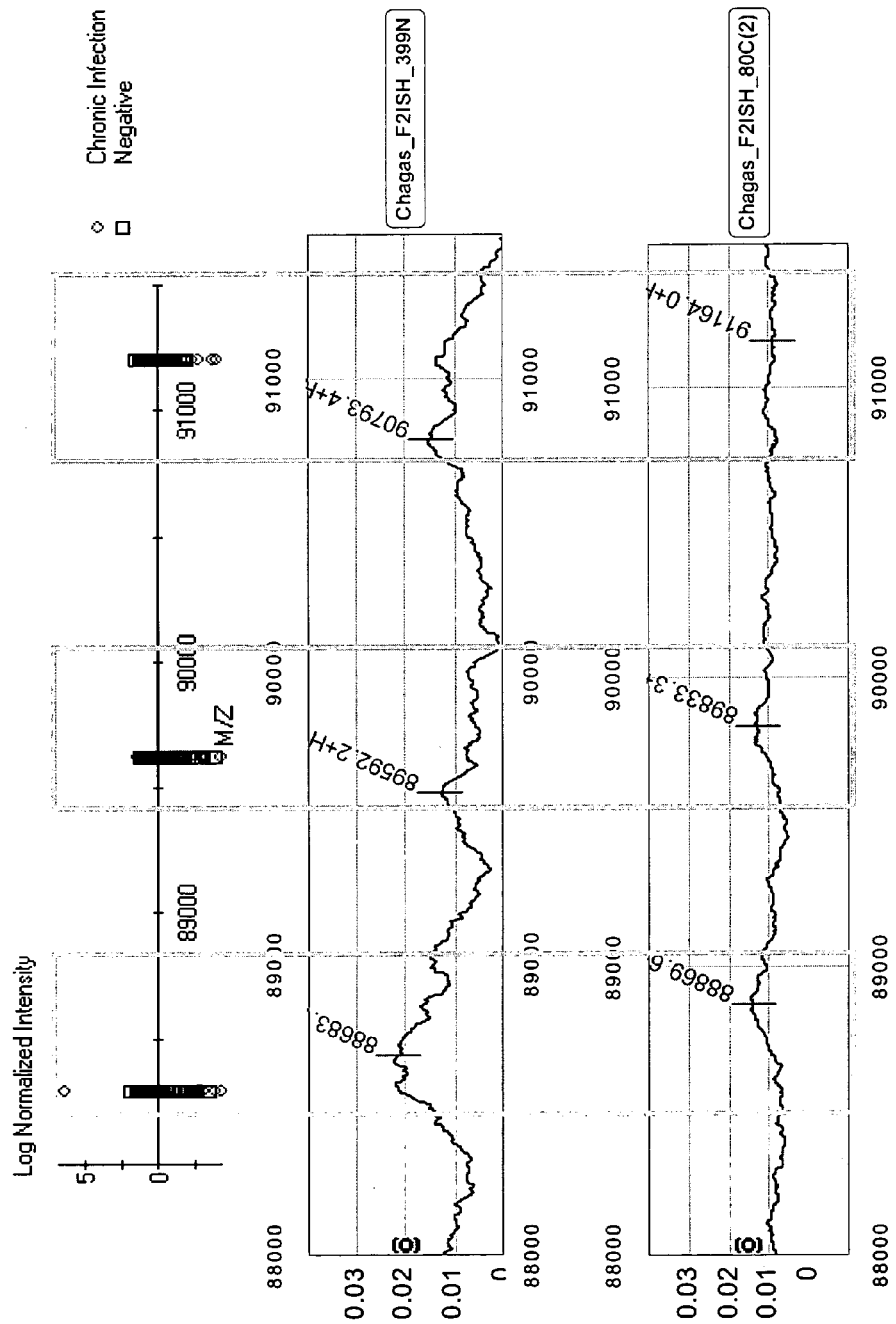
Figure 1J:
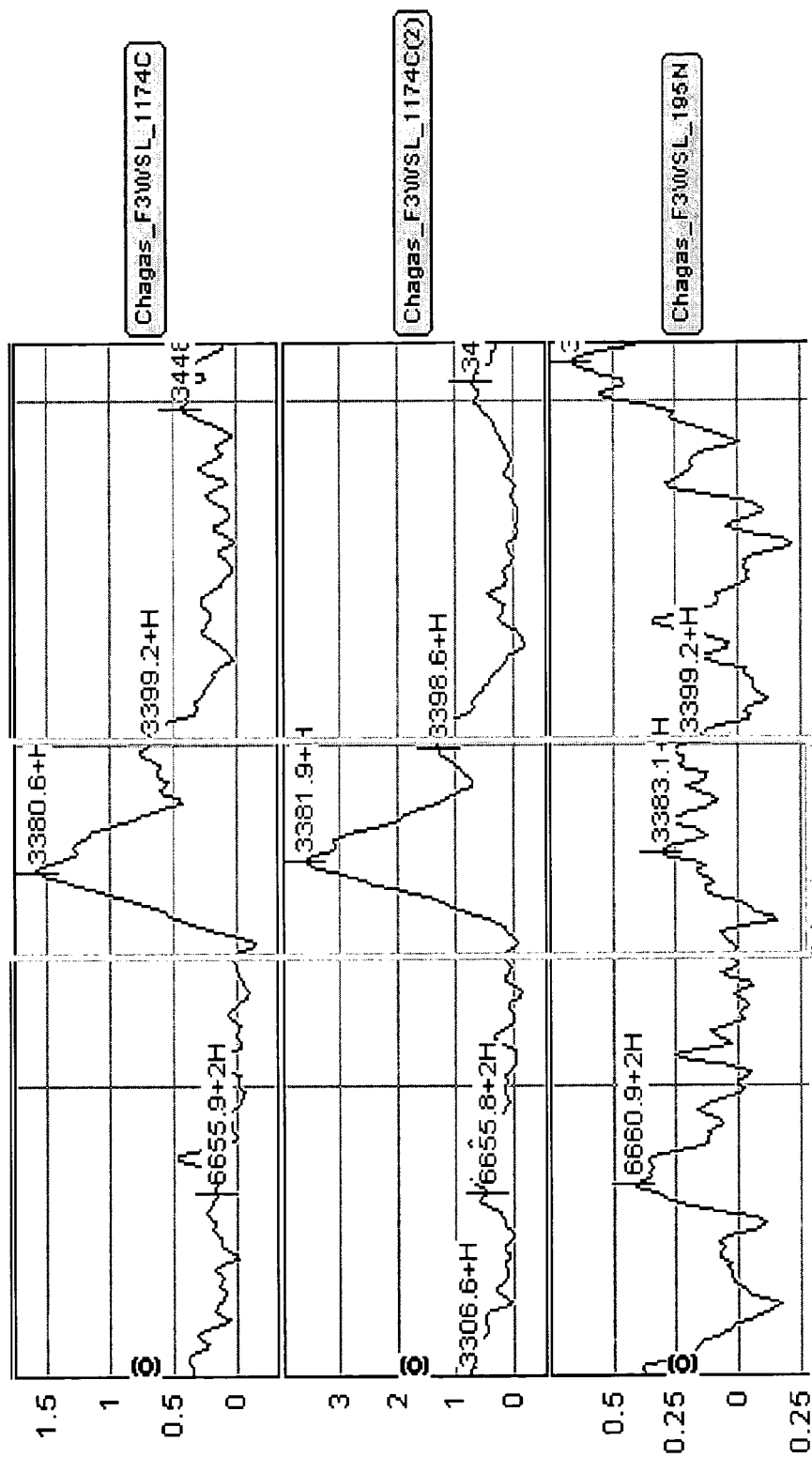
Figure 1K:
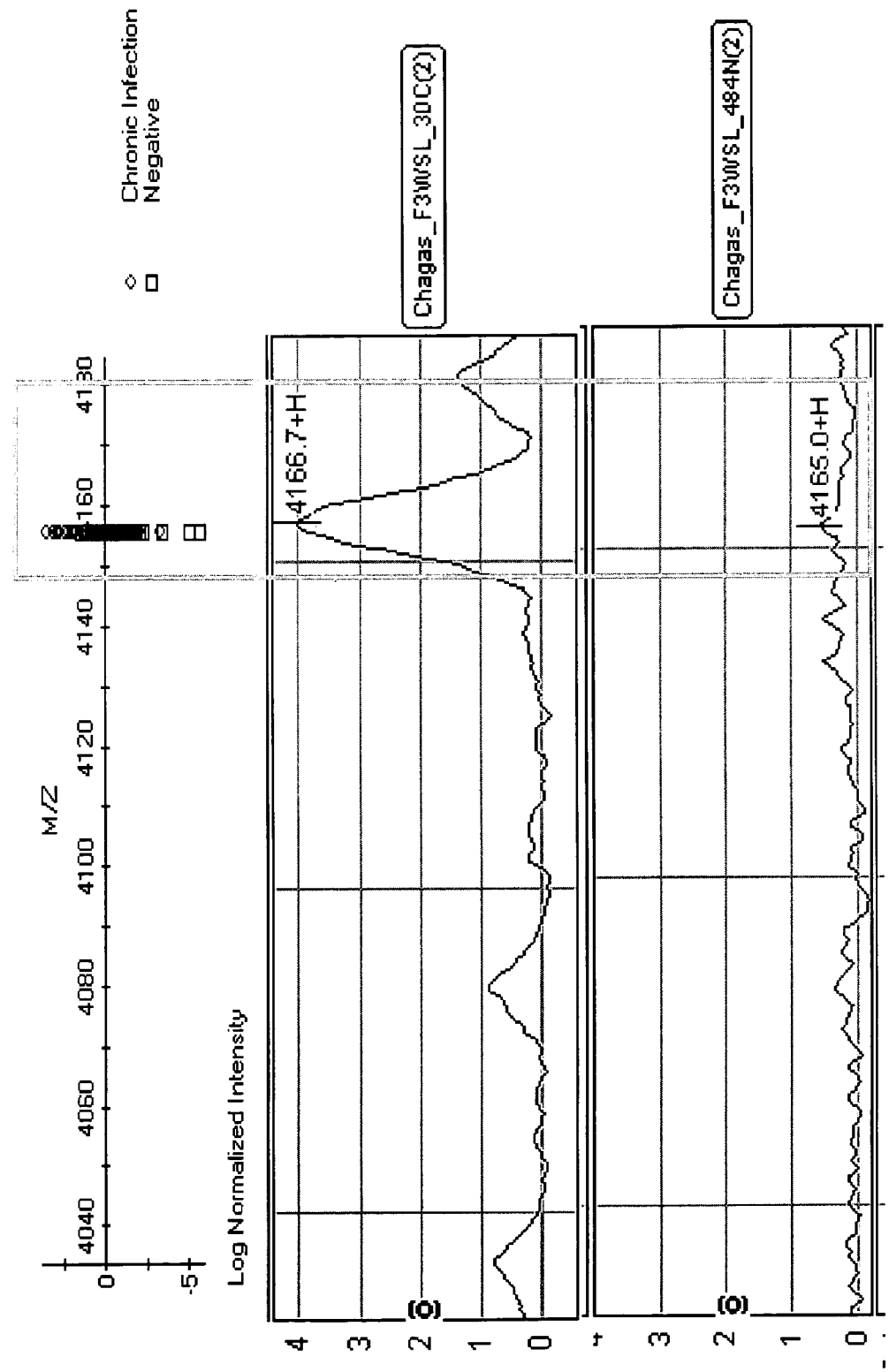
Figure 1L:
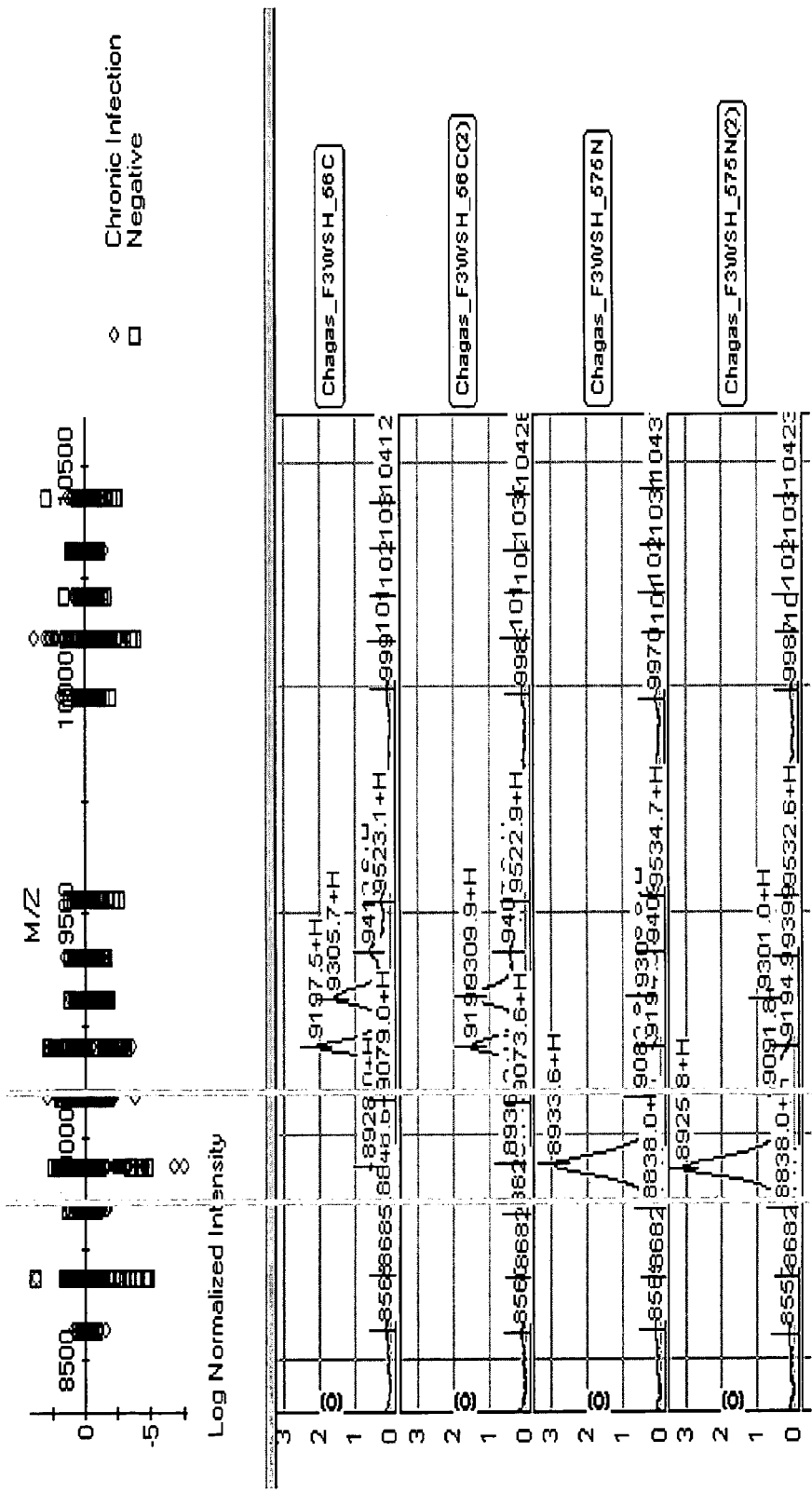
Figure 1M:
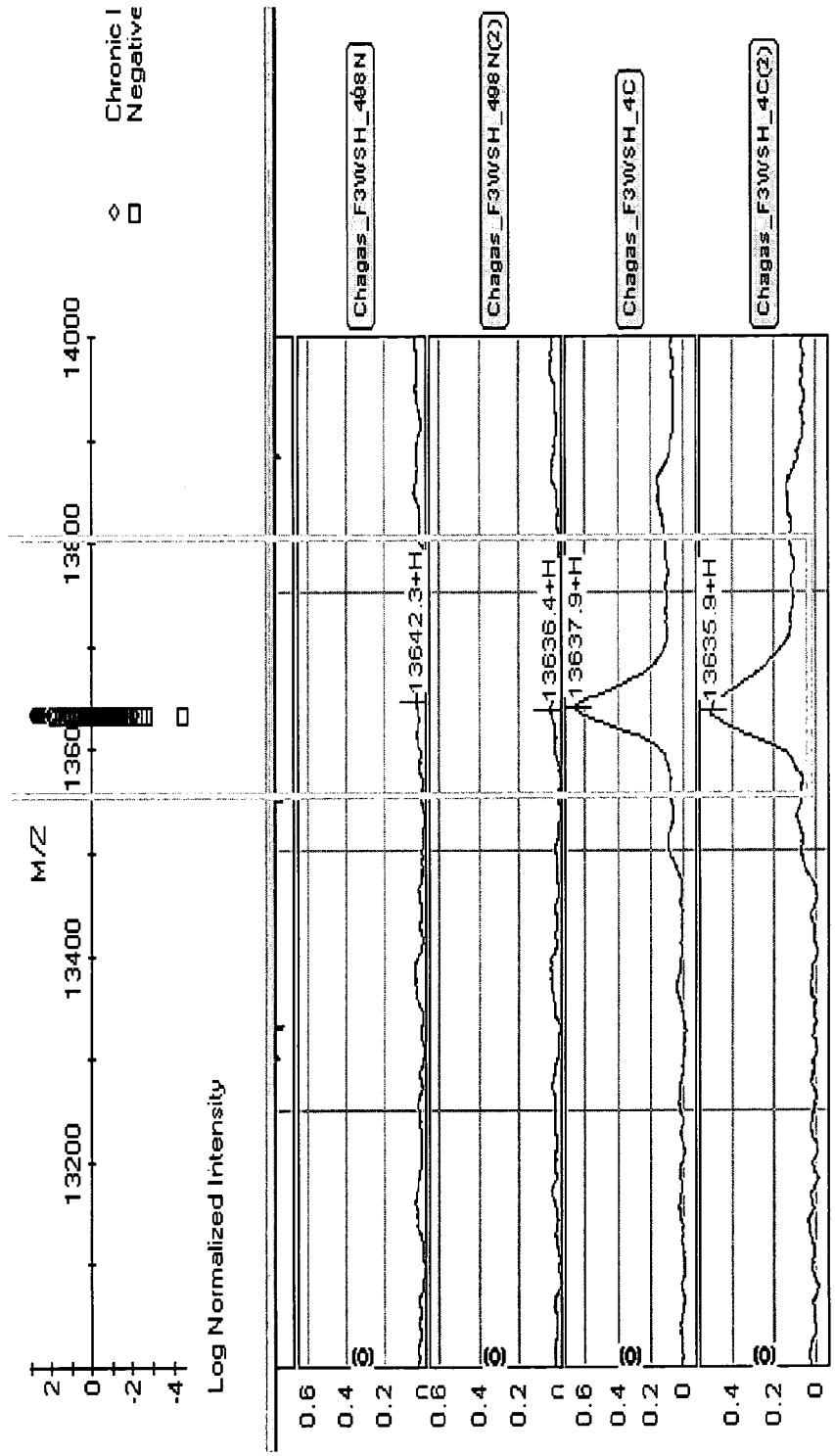
Figure 1N:
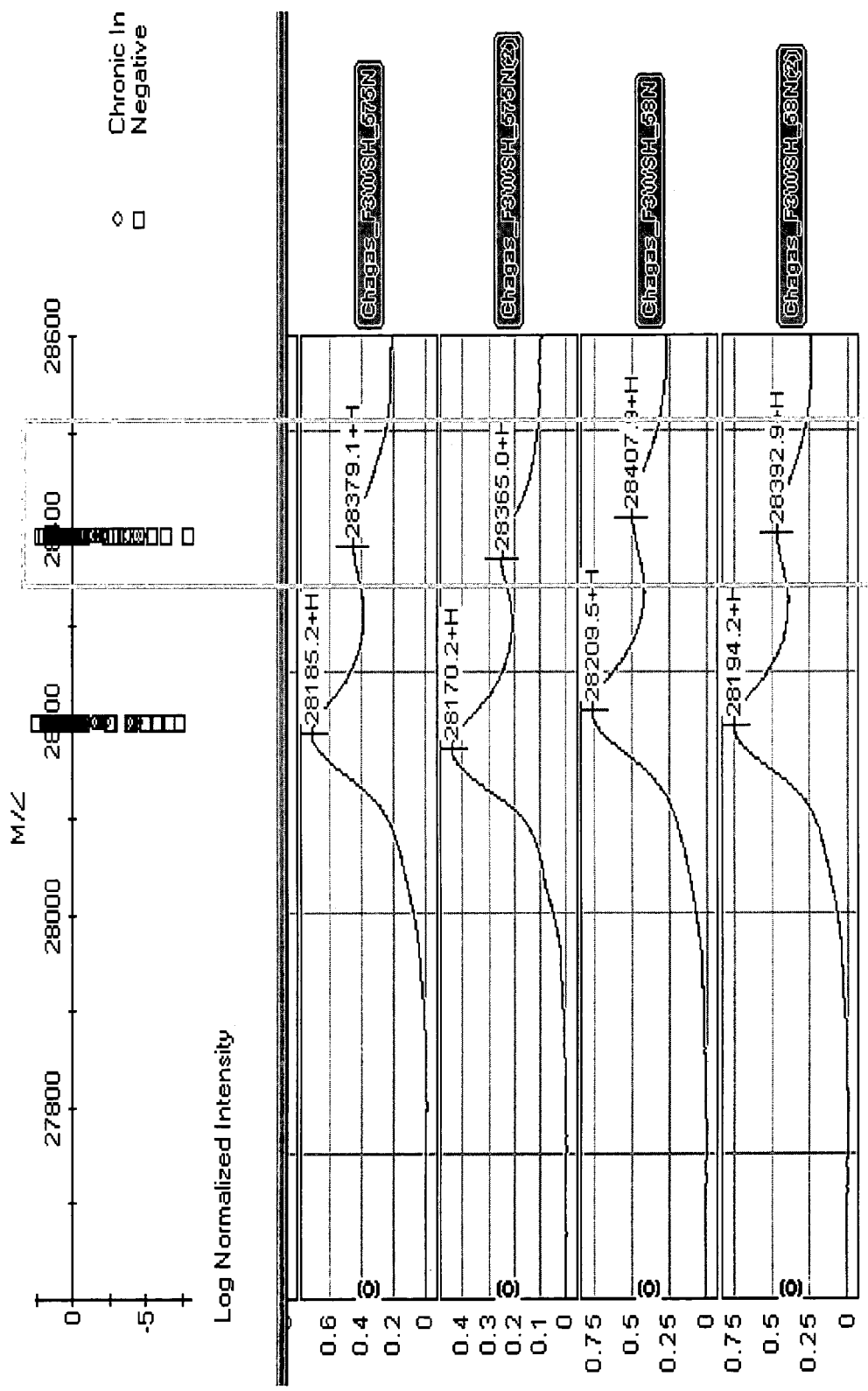
Figure 10:
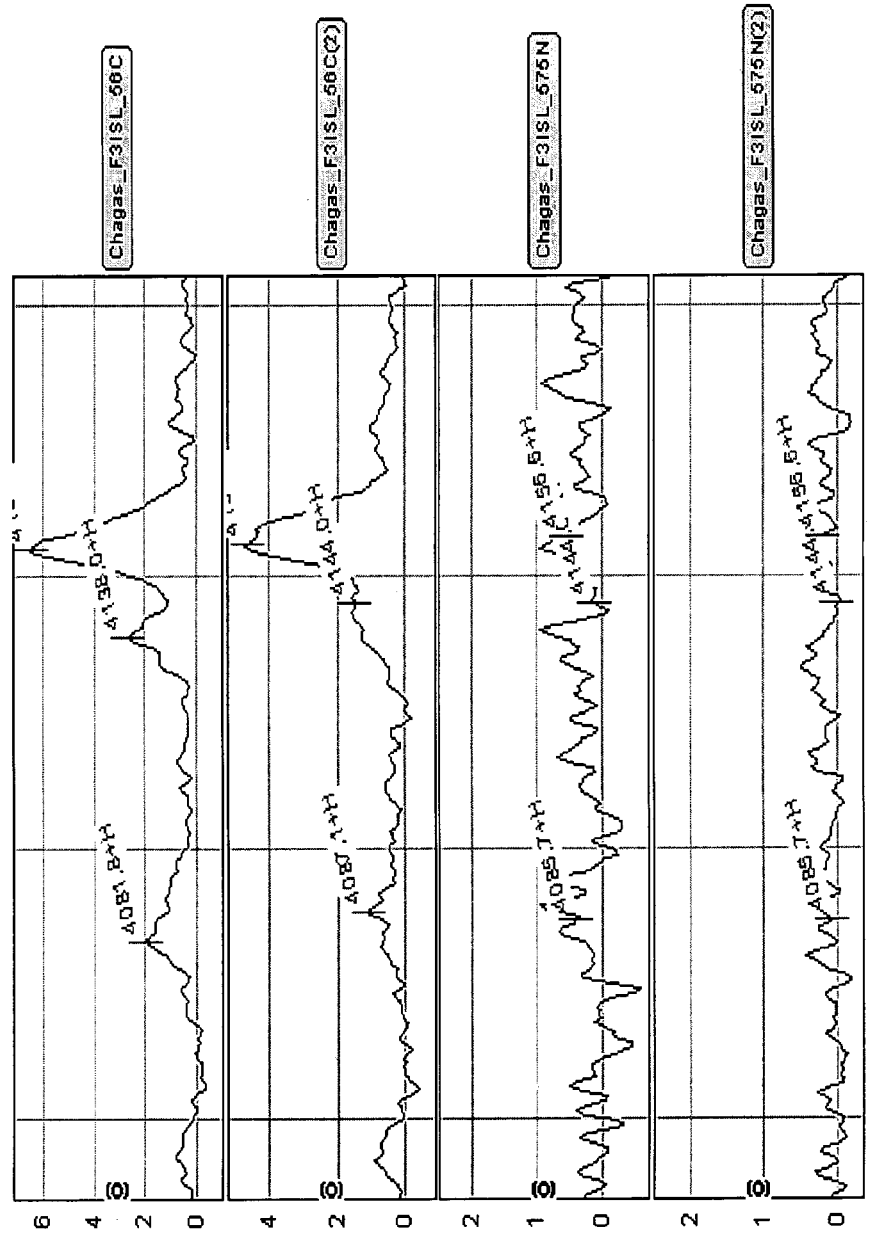
Figure 1P:
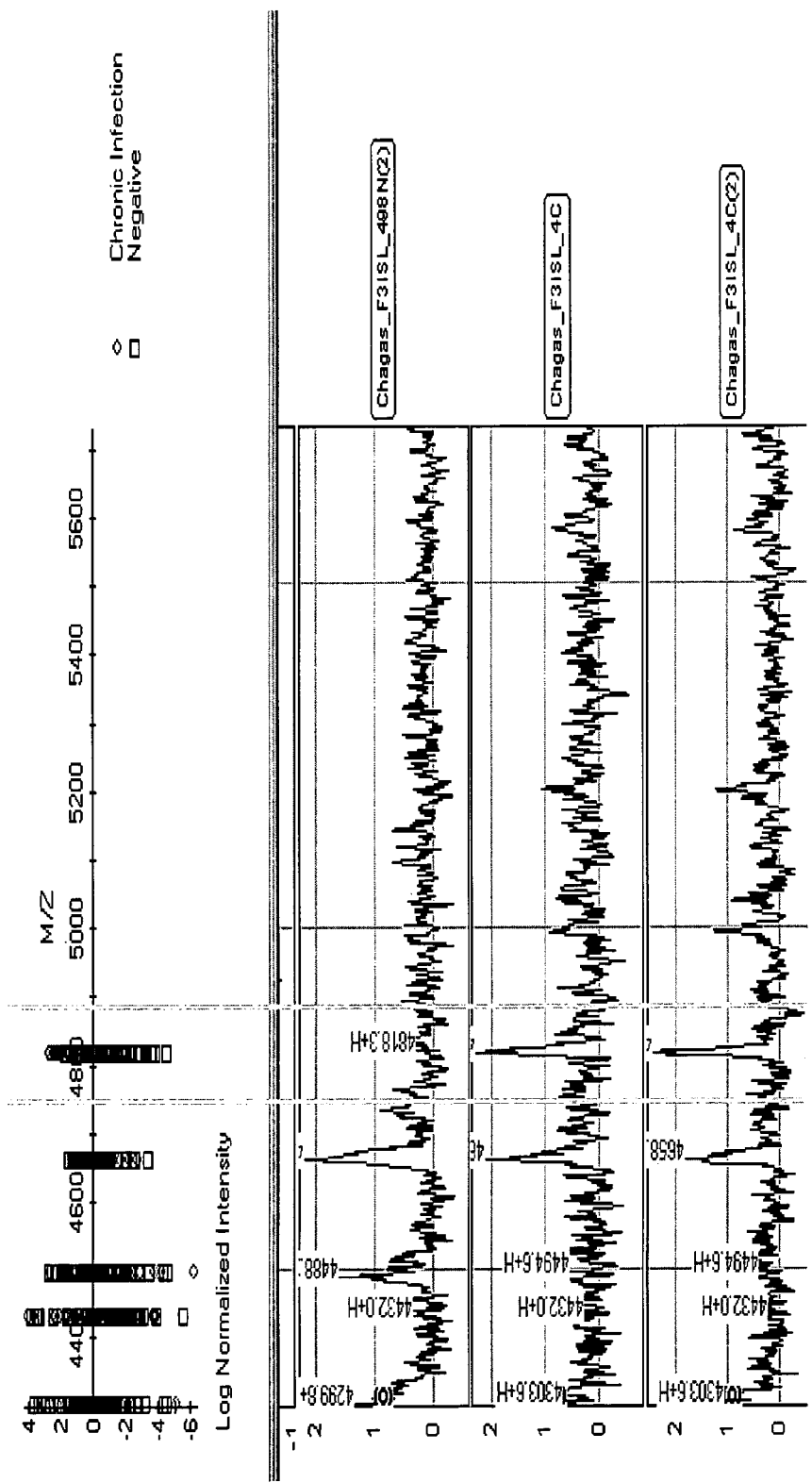
Figure 1Q:
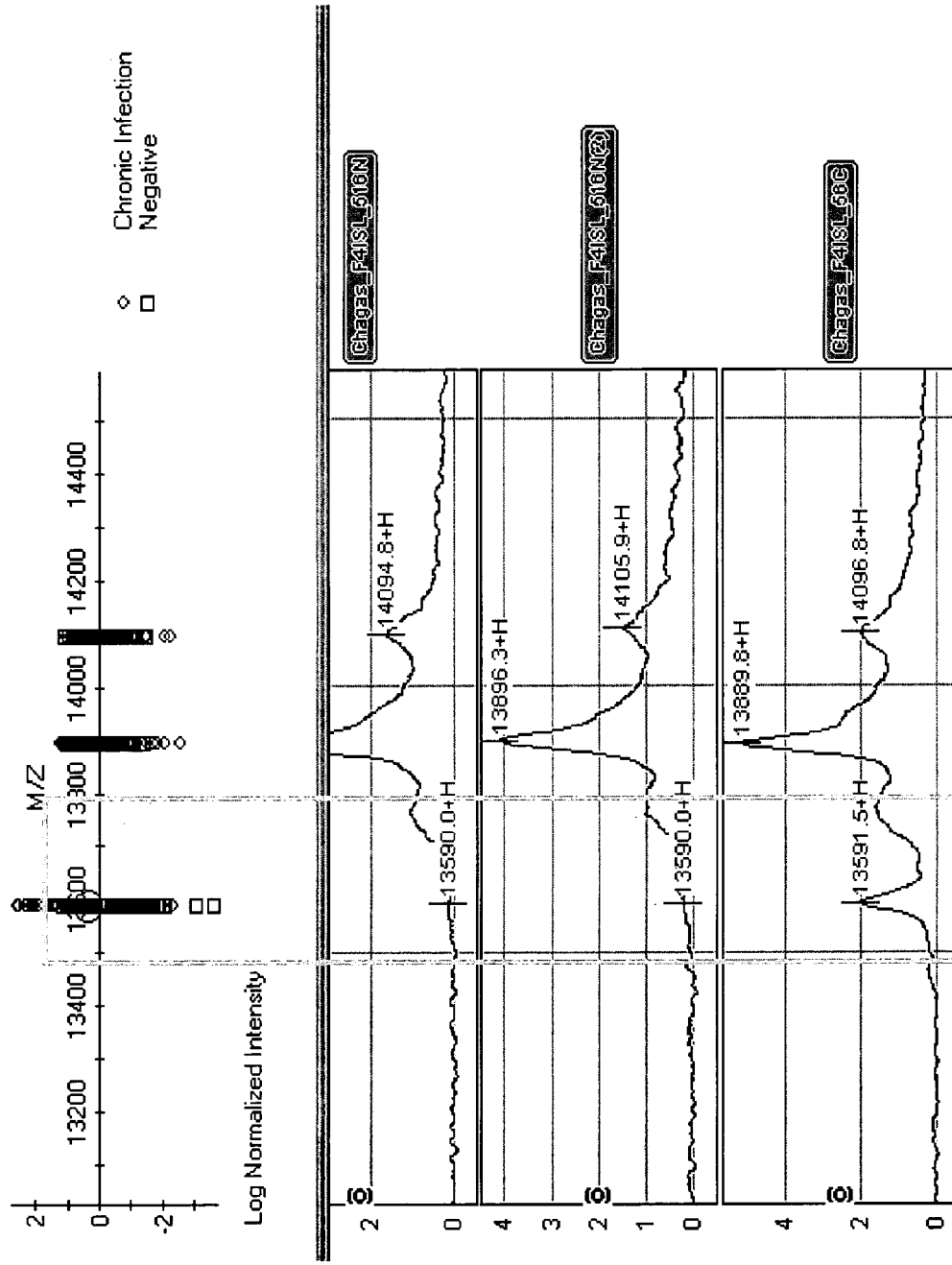
Figure 1R:
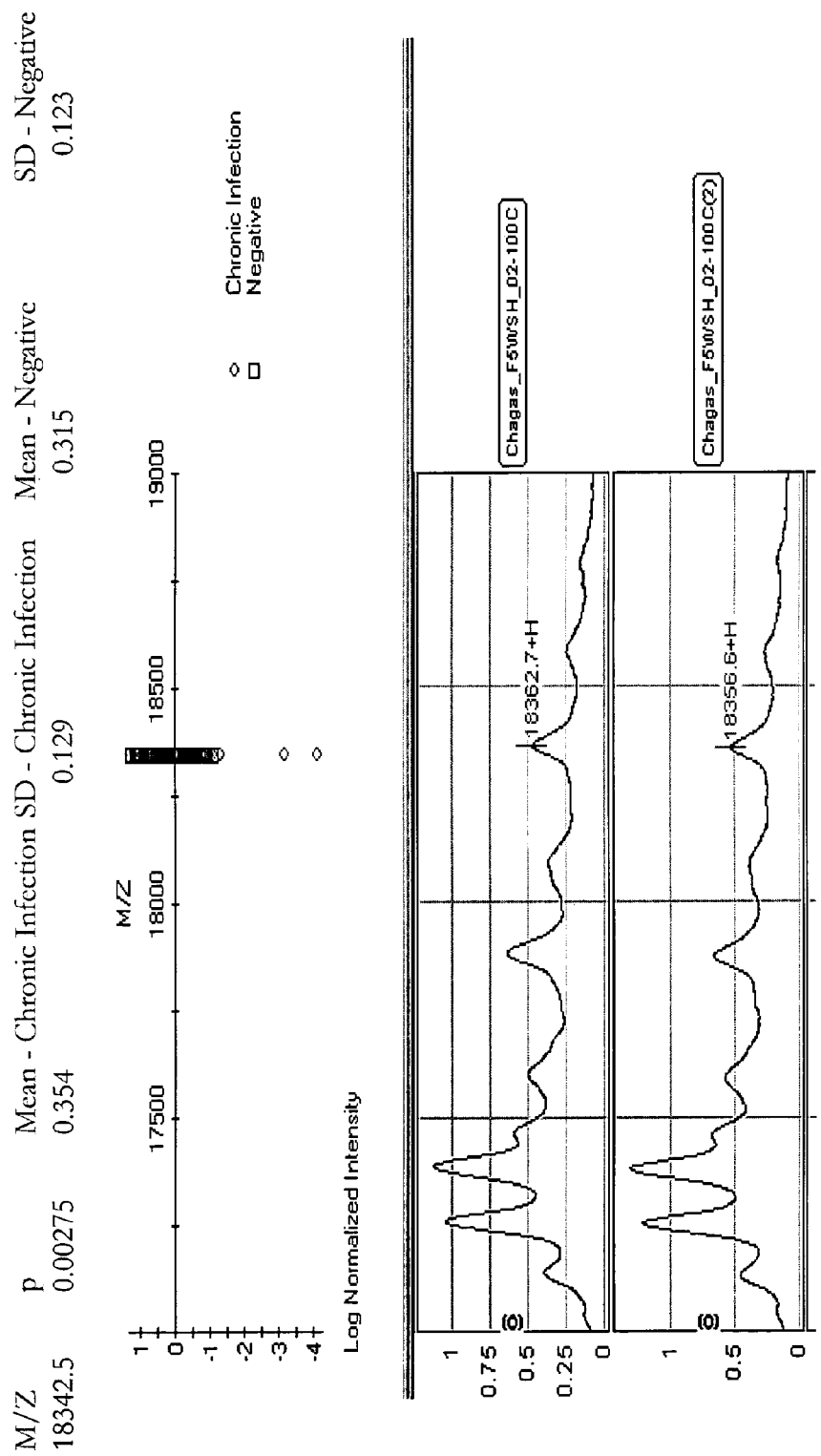

A biomarker is an organic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Common tests for statistical significance include, among others, t-test, ANOVA, Kruskal-Wallis, Wilcoxon, Mann-Whitney and odds ratio. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

II. Biomarkers for Chagas Disease

A. Biomarkers

This invention provides, among other useful features, polypeptide-based biomarkers that are differentially present in subjects having Chagas disease versus healthy uninfected healthy individuals. The biomarkers are characterized by mass-to-charge ratio as determined by mass spectrometry, by the shape of their spectral peak in time-of-flight mass spectrometry and by their binding characteristics to adsorbent surfaces. These characteristics provide one method to determine whether a particular detected biomolecule is a biomarker of this invention. These characteristics represent inherent characteristics of the biomolecules and not process limitations in the manner in which the biomolecules are discriminated. In one aspect, this invention provides these biomarkers in isolated form.

The biomarkers were discovered using SELDI technology employing ProteinChip arrays from Ciphergen Biosystems, Inc. (Fremont, Calif.) ("Ciphergen"). Serum samples were collected from subjects diagnosed with Chagas disease and subjects diagnosed as normal (non-demented). The samples were fractionated by anion exchange chromatography. Fractionated samples were applied to SELDI biochips and spectra of polypeptides in the samples were generated by time-of-flight mass spectrometry on a Ciphergen PBSII mass spectrometer. The spectra thus obtained were analyzed by Ciphergen Express™ Data Manager Software with Biomarker Wizard and Biomarker Pattern Software from Ciphergen Biosystems, Inc. The mass spectra for each group were subjected to scatter plot analysis. A Mann-Whitney test analysis was employed to compare Chagas disease and control groups for each protein cluster in the scatter plot, and proteins were selected that differed significantly (p<0.006, but preferably less than 0.0001) between the two groups. This method is described in more detail in the Example Section.

The biomarkers thus discovered are presented in Tables 1-4, and additionally in FIGS. 5-9. With respect to Table 1, the "ProteinChip assay" column refers to the chromatographic fraction in which the biomarker is found, the type of biochip to which the biomarker binds and the wash conditions, as per the Example. For Example, F1, F2, etc., refer to "Fraction 1," "Fraction 2," etc. "I" refers to the use of the commercially available IMAC-3 ProteinChip ("Ciphergen Biosystems, Inc."). "W" refers to the use of the commercially available WCX2 ProteinChip ("Ciphergen Biosystems, Inc."). "H" and "L" refers to the reading of SELDI-MS data at high and low intensities, respectively. This code, along with a unique number, is used to determine a Marker ID. In addition, all of the biomarkers disclosed herein were first discovered using ProteinChip assays which employed the use of sinapinic acid (SPA) as an Energy Absorbing Molecule (EAM), as described in greater detail below and in the Examples. The "S" which appears in the Marker ID for the biomarkers of Tables 2-4 refers to the use of SPA. Biomarkers may also be referred to as M### where the ### represents the biomarker's measured mass to charge ratio (M/Z), or they may be referred to by their molecular weights (e.g., "the 110 kDa biomarker"). Where a particular biomarker has been subjected to further identification protocols, as described herein, the marker identity is indicated in the Table along with a description of its length by reference to the full-length protein (e.g., the 13.6 kDa peak, labeled F1IH_1 in Table 1, corresponds to the C-terminal fragment of Apolipoprotein A1, amino acids 124-243).

TABLE 1

| M/Z (kDa) | p-value | Fraction, ProteinChip and beam intensity | Marker ID |
|---|---|---|---|
| 13.6 | <0.006 | F1IH | F1IH_1 C-terminal fragment of Apo A1 (124-243) |
| 16.3 | <0.006 | F1IH | F1IH_2 Dimer of truncated C3 anaphylatoxin (1-68) |
| 8.335027 | <0.006 | F1IL | F1IL_1 |
| 8.349768 | <0.006 | F1IL | F1IL_2 |
| 4.476274 | <0.006 | F1IL | F1IL_3 Double-charged peak of C3 anaphylatoxin des Arg (1-76) |
| 8.950683 | <0.006 | F1IL | F1IL_4 C3 anaphylatoxin des Arg (1-76) |
| 7.190033 | <0.006 | F1IL | F1IL_5 |
| 9.155242 | <0.006 | F1IL | F1IL_6 |
| 8.14304 | <0.006 | F1IL | F1IL_7 C-terminal truncation of C3 anaphylatoxin (1-68) |
| 9.254734 | <0.006 | F1IL | F1IL_8 |
| 8.935389 | <0.006 | F1IL | F1IL_9 |
| 8.4567 | <0.006 | F1IL | F1IL_10 |
| 4.066244 | <0.006 | F1IL | F1IL_11 |
| 8.130521 | <0.006 | F1IL | F1IL_12 |
| 8.43914 | <0.006 | F1IL | F1IL_13 |
| 4.808781 | <0.006 | F1IL | F1IL_14 |
| 8.642292 | <0.006 | F1IL | F1IL_15 |
| 9.299242 | <0.006 | F1IL | F1IL_16 |
| 4.21785 | <0.006 | F1IL | F1IL_17 |
| 2.491823 | <0.006 | F1IL | F1IL_18 |
| 4.079363 | <0.006 | F1IL | F1IL_19 |
| 4.174495 | <0.006 | F1IL | F1IL_20 |
| 3.29103 | <0.006 | F1IL | F1IL_21 |
| 10.070 | <0.006 | F1WH | F1WH_1 C-terminal fragment of Apo A1 (154-243) |
| 13.6 | <0.006 | F1WH | F1WH_2 C-terminal fragment of Apo A1 (124-243) |
| 13.85 | <0.006 | F1WH | F1WH_3 |
| 16.3 | <0.006 | F1WH | F1WH_4 Dimer of truncated C3 anaphylatoxin (1-68) |
| 16.5 | <0.006 | F1WH | F1WH_5 |
| 28.957 | <0.006 | F1WH | F1WH_6 N-terminal fragment of fibronectin (1-258) |
| 12.952 | <0.006 | F1WH | F1WH_7 |
| 28.79 | <0.006 | F1WH | F1WH_8 |
| 15.67 | <0.006 | F1WH | F1WH_9 |
| 16.7 | <0.006 | F1WH | F1WH_10 |

TABLE 1-continued

| M/Z (kDa) | p-value | Fraction, ProteinChip and beam intensity | Marker ID |
|---|---|---|---|
| 12.75 | <0.006 | F1WH | F1WH_11 |
| 31.78 | <0.006 | F1WH | F1WH_12 |
| 8.935 | <0.006 | F1WL | F1WL_1 |
| 4.480 | <0.006 | F1WL | F1WL_2 |
| 9.308 | <0.006 | F1WL | F1WL_3 C-terminal fragment of Apo A1 (161-243) |
| 8.351 | <0.006 | F1WL | F1WL_4 |
| 8.129 | <0.006 | F1WL | F1WL_5 C-terminal truncation of C3 anaphylatoxin (1-68) |
| 4.078 | <0.006 | F1WL | F1WL_6 |
| 8.335 | <0.006 | F1WL | F1WL_7 |
| 8.142 | <0.006 | F1WL | F1WL_8 |
| 7.483 | <0.006 | F1WL | F1WL_9 |
| 7.178 | <0.006 | F1WL | F1WL_10 |
| 6.454 | <0.006 | F1WL | F1WL_11 Apolipoprotein C1 (missing 2 N-terminal amino acids) |
| 6.636 | <0.006 | F1WL | F1WL_12 Apolipoprotein C1 |
| 89.6 | <0.006 | F2IH | F2IH_1 |
| 88.3 | <0.006 | F2IH | F2IH_2 |
| 37.7 | <0.006 | F2IH | F2IH_3 |
| 54.04 | <0.006 | F2IH | F2IH_4 |
| 91.16 | <0.006 | F2IH | F2IH_5 |
| 8.350 | <0.006 | F2IL | F2IL_1 |
| 8.156 | <0.006 | F2IL | F2IL_2 |
| 4.079 | <0.006 | F2IL | F2IL_3 |
| 28.7 | <0.006 | F2WH | F2WH_1 |
| 33.8 | <0.006 | F2WH | F2WH_2 |
| 4.812 | <0.006 | F2WL | F2WL_1 |
| 5.458 | <0.006 | F2WL | F2WL_2 |
| 4.072 | <0.006 | F2WL | F2WL_3 |
| 10.3 | <0.006 | F3IH | F3IH_1 |
| 10.46 | <0.006 | F3IH | F3IH_2 |
| 4.819 | <0.006 | F3IL | F3IL_1 |
| 4.157 | <0.006 | F3IL | F3IL_2 |
| 8.966 | <0.006 | F3IL | F3IL_3 |
| 5.995 | <0.006 | F3IL | F3IL_4 |
| 4.145 | <0.006 | F3IL | F3IL_5 |
| 4.495 | <0.006 | F3IL | F3IL_6 |
| 8.148 | <0.006 | F3IL | F3IL_7 |
| 13.6 | <0.006 | F3WH | F3WH_1 C-terminal fragment of Apo A1 (124-243) |
| 14.2 | <0.006 | F3WH | F3WH_2 |
| 14.09 | <0.006 | F3WH | F3WH_3 |
| 28.2 | <0.006 | F3WH | F3WH_4 |
| 28.393 | <0.006 | F3WH | F3WH_5 |
| 10.1 | <0.006 | F3WH | F3WH_6 |
| 17.47 | <0.006 | F3WH | F3WH_7 |
| 37.4 | <0.006 | F3WH | F3WH_8 |
| 8.943 | <0.006 | F3WL | F3WL_1 |
| 3.400 | <0.006 | F3WL | F3WL_2 |
| 3.384 | <0.006 | F3WL | F3WL_3 |
| 4.156 | <0.006 | F3WL | F3WL_4 |
| 5.993 | <0.006 | F3WL | F3WL_5 |
| 4.234 | <0.006 | F3WL | F3WL_6 |
| 4.219 | <0.006 | F3WL | F3WL_7 |
| 8.133 | <0.006 | F3WL | F3WL_8 C-terminal truncation of C3 anaphylatoxin (1-68) |
| 8.147 | <0.006 | F3WL | F3WL_9 |
| 6.452 | <0.006 | F3WL | F3WL_10 |
| 13.6 | <0.006 | F4IH | F4IH_1 C-terminal fragment of Apo A1 (124-243) |
| 10.046 | <0.006 | F4IH | F4IH_2 |
| 10.243 | <0.006 | F4IH | F4IH_3 |
| 24.77 | <0.006 | F4IH | F4IH_4 N-terminal fragment of Apo A1 (1-214) |
| 8.943 | <0.006 | F4IL | F4IL_1 |
| 8.146 | <0.006 | F4IL | F4IL_2 |
| 13.6 | <0.006 | F4WH | F4WH_1 |
| 10.039 | <0.006 | F4WH | F4WH_2 |
| 24.7 | <0.006 | F4WH | F4WH_3 |
| 9.348 | <0.006 | F4WH | F4WH_4 |
| 6.457 | <0.006 | F4WL | F4WL_1 |
| 8.132 | <0.006 | F4WL | F4WL_2 |
| 8.945 | <0.006 | F4WL | F4WL_3 |
| 3.383 | <0.006 | F4WL | F4WL_4 |
| 8.150 | <0.006 | F4WL | F4WL_5 |
| 9.305 | <0.006 | F4WL | F4WL_6 |
| 3.968 | <0.006 | F4WL | F4WL_7 |
| 5.017 | <0.006 | F4WL | F4WL_8 |
| 51.6 | <0.006 | F5IH | F5IH_1 |
| 8.142 | <0.006 | F5IL | F5IL_1 |
| 7.933 | <0.006 | F5IL | F5IL_2 |
| 4.627 | <0.006 | F5IL | F5IL_3 |
| 13.544 | <0.006 | F5WH | F5WH_1 |
| 14.36 | <0.006 | F5WH | F5WH_2 |
| 14.54 | <0.006 | F5WH | F5WH_3 |
| 17.89 | <0.006 | F5WH | F5WH_4 |
| 18.7 | <0.006 | F5WH | F5WH_5 |
| 33.5 | <0.006 | F5WH | F5WH_6 |
| 11.86 | <0.006 | F5WH | F5WH_7 |
| 6.453 | <0.006 | F5WL | F5WL_1 |
| 8.128 | <0.006 | F5WL | F5WL_2 |
| 8.948 | <0.006 | F5WL | F5WL_3 |
| 6.231 | <0.006 | F5WL | F5WL_4 |
| 6.335 | <0.006 | F5WL | F5WL_5 |
| 6.843 | <0.006 | F5WL | F5WL_6 |
| 5.990 | <0.006 | F5WL | F5WL_7 |
| 28.324 | <0.006 | F6IH | F6IH_1 |
| 84.3 | <0.006 | F6IH | F6IH_2 |
| 28.123 | <0.006 | F6IH | F6IH_3 |
| 56.4 | <0.006 | F6IH | F6IH_4 |
| 28.5 | <0.006 | F6IH | F6IH_5 |
| 8.951 | <0.006 | F6IL | F6IL_1 |
| 6.648 | <0.006 | F6IL | F6IL_2 |
| 8.145 | <0.006 | F6IL | F6IL_3 |
| 14.394 | <0.006 | F6WH | F6WH_1 |
| 14.579 | <0.006 | F6WH | F6WH_2 |
| 18.6 | <0.006 | F6WH | F6WH_3 |
| 8.939 | <0.006 | F6WL | F6WL_1 |
| 6.844 | <0.006 | F6WL | F6WL_2 |
| 3.322 | <0.006 | F6WL | F6WL_3 |
| 2.013 | <0.006 | F6WL | F6WL_4 |
| 6.639 | <0.006 | F6WL | F6WL_5 |

The biomarkers of this invention are characterized by their mass-to-charge ratio as determined by mass spectrometry. The mass-to-charge ratio of each biomarker is provided in Table 1 under the column heading "M/Z." The mass-to-charge ratios were determined from mass spectra generated on a Ciphergen Biosystems, Inc. PBS II mass spectrometer. This instrument has a mass accuracy of about +/−0.15 percent for markers with molecular weights of approximately 20 kDa or less, and roughly 2.0% for markers of molecular weights above approximately 20 kDa. Additionally, the instrument has a mass resolution of about 400 to 1000 m/dm, where m is mass and dm is the mass spectral peak width at 0.5 peak height. The mass-to-charge ratio of the biomarkers was determined using Biomarker Wizard™ software (Ciphergen Biosystems, Inc.). Biomarker Wizard assigns a mass-to-charge ratio to a biomarker by clustering the mass-to-charge ratios of the same peaks from all the spectra analyzed, as determined by the PBSII, taking the maximum and minimum mass-to-charge-ratio in the cluster, and dividing by two. Accordingly, the masses provided reflect these specifications.

Figure 1:
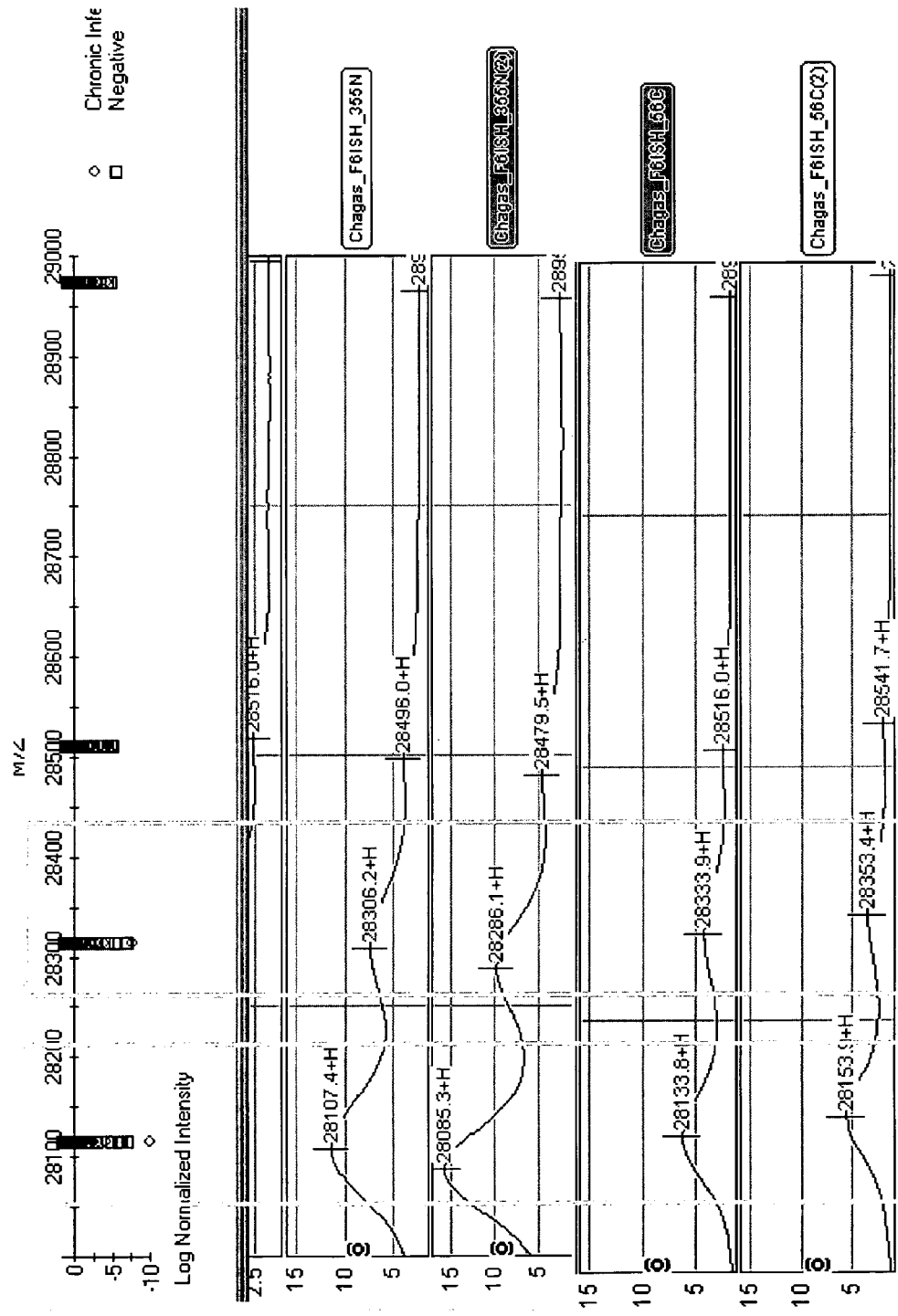
Figure 1T:
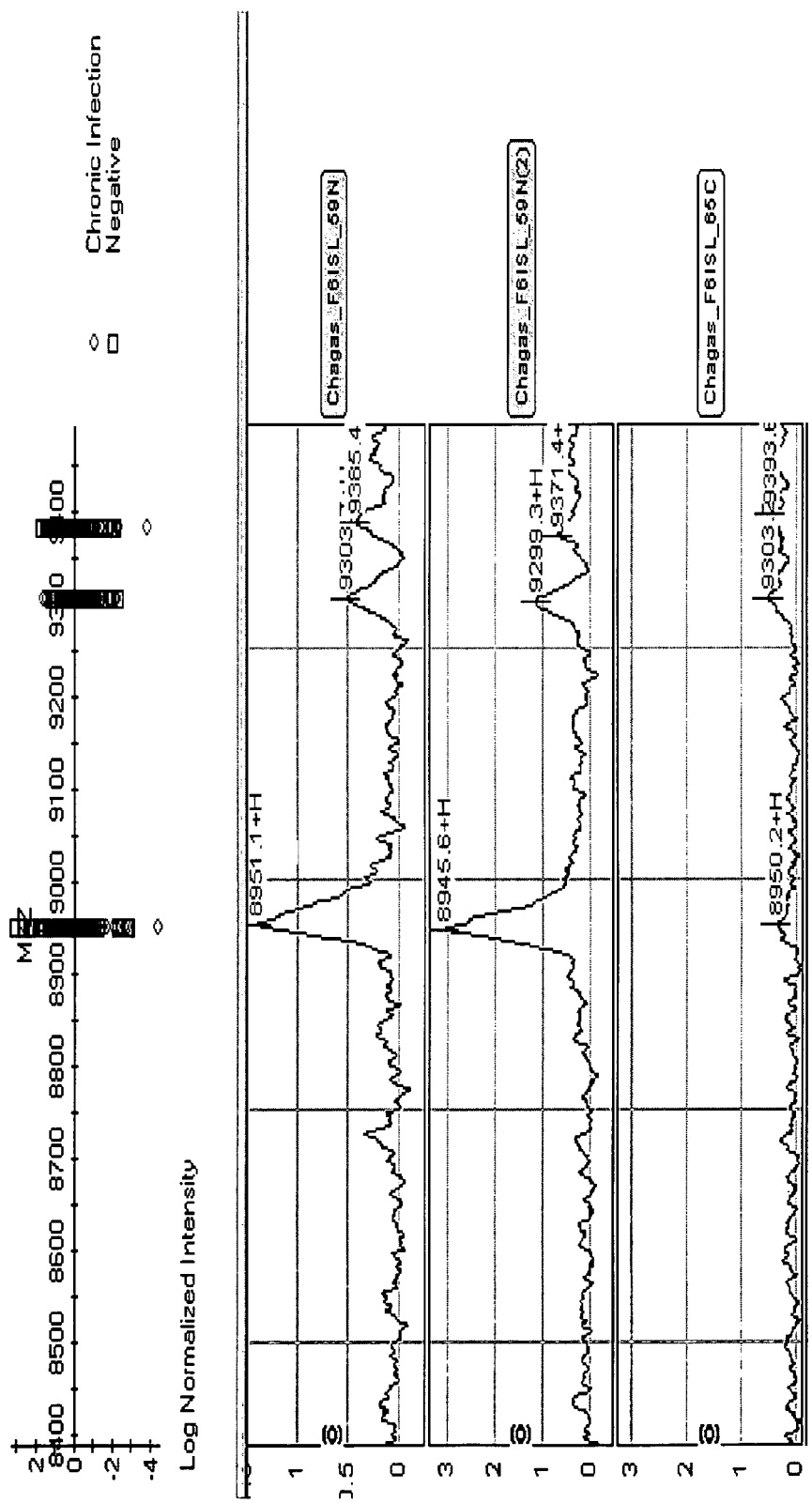
Figure 1:
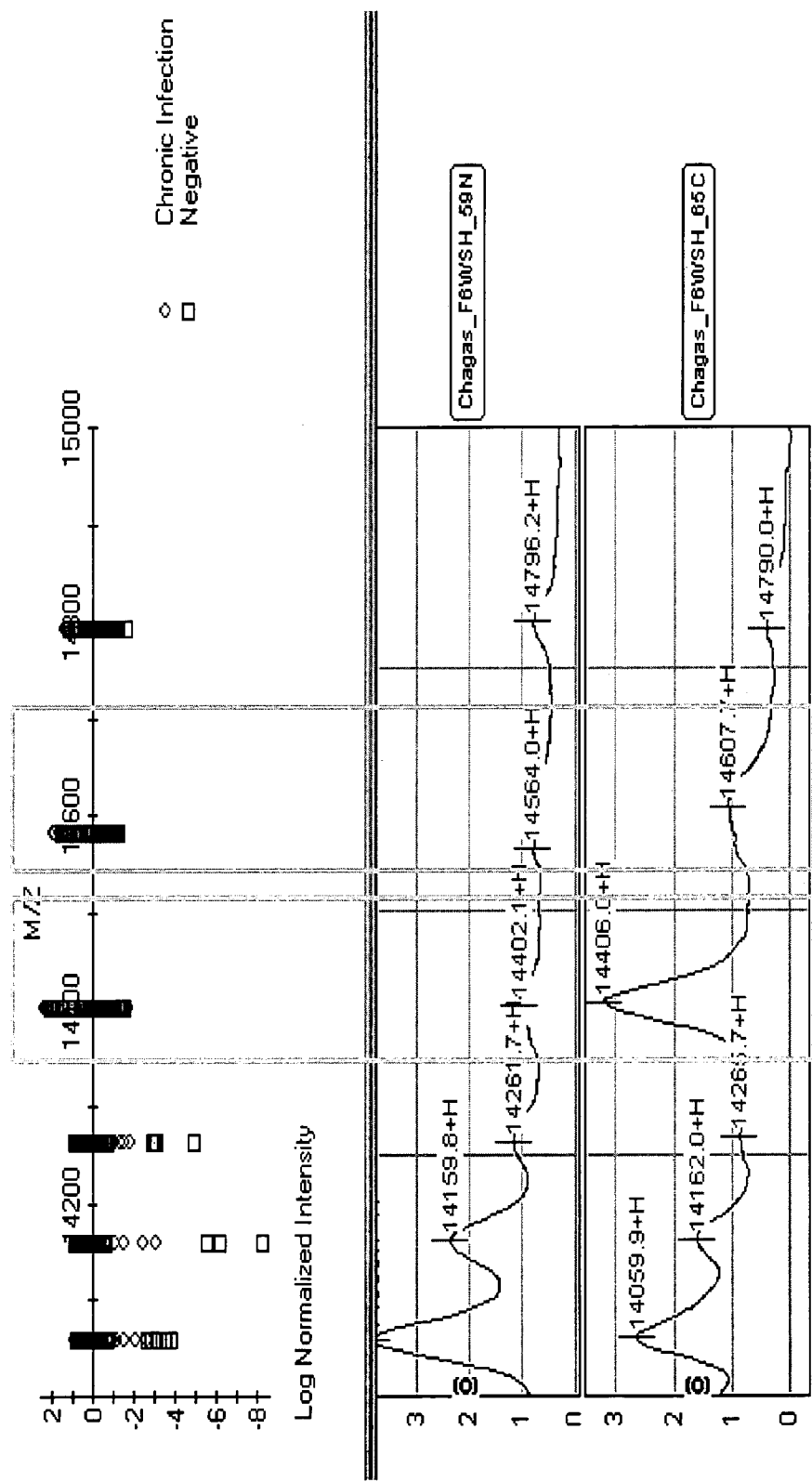
Figure 1W:
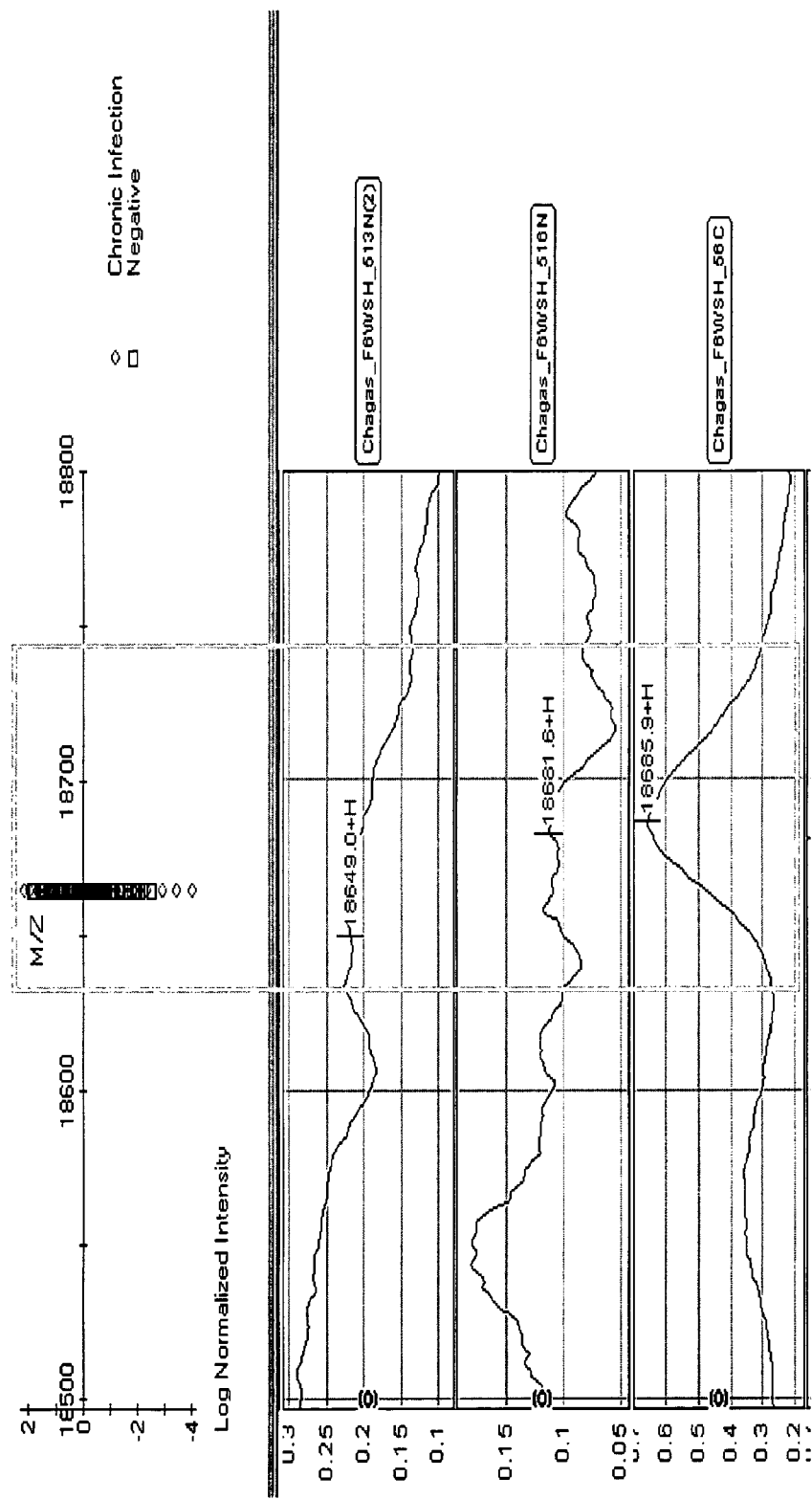

The biomarkers of this invention are further characterized by the shape of their spectral peak in time-of-flight mass spectrometry. Mass spectra showing the shapes of peaks corresponding to representative biomarkers are presented in FIG. 1.

The biomarkers of this invention are further characterized by their binding properties on chromatographic surfaces, i.e., their ability to bind to the IMAC-2 ProteinChips versus their ability to bind to WXC2 cation exchange ProteinChips.

The identities of certain biomarkers of this invention have been determined. The method by which this determination was made is described below. For biomarkers whose identify has been determined, the presence of the biomarker (or nucleic acid encoding the biomarker) in a sample or subject can be determined by other methods known in the art including, but not limited to, methods such as Western blotting, Southern blotting, or PCR.

Because the biomarkers of this invention are characterized by mass-to-charge ratio, binding properties and spectral shape, they can be detected by mass spectrometry without knowing their specific identity. However, if desired, biomarkers whose identity is not determined can be identified by, for example, determining the amino acid sequence of the polypeptides. For example, a biomarker can be peptide-mapped with a number of enzymes, such as trypsin or V8 protease, and the molecular weights of the digestion fragments can be used to search databases for sequences that match the molecular weights of the digestion fragments generated by the various enzymes. Alternatively, protein biomarkers can be sequenced using tandem MS technology. In this method, the protein is isolated by, for example, gel electrophoresis. A band containing the biomarker is cut out and the protein is subject to protease digestion. Individual protein fragments are separated by a first mass spectrometer. The fragment is then subjected to collision-induced cooling, which fragments the peptide and produces a polypeptide ladder. A polypeptide ladder is then analyzed by the second mass spectrometer of the tandem MS. The difference in masses of the members of the polypeptide ladder identifies the amino acids in the sequence. An entire protein can be sequenced this way, or a sequence fragment can be subjected to database mining to find identity candidates.

The preferred biological source for detection of the biomarkers is serum. However, in other embodiments, the biomarkers can be detected in any tissues of interest where infectious material may be found. In the case of blood samples, stocks of blood may be tested by isolating the blood serum according to techniques well-known in the art. The serum can then be analyzed according to the techniques described herein. If the measurements taken from blood samples indicate that the individual from which the blood was taken was infected with Chagas disease, then the blood may be treated with purification agents available to one skilled in the art including, but not limited to, agents such as gentian violet, ascorbic acid, and aminoloquinolone WR6026. Alternatively, the infected blood may be discarded or destroyed and only stocks of blood which have not tested positively for Chagas disease are retained.

The biomarkers of this invention are biomolecules. Accordingly, this invention provides these biomolecules in isolated form. The biomarkers can be isolated from biological fluids, such as serum. They can be isolated by any method known in the art, based on both their mass and their binding characteristics. For example, a sample comprising the biomolecules can be subject to chromatographic fractionation, as described herein, and subject to further separation by, e.g., acrylamide gel electrophoresis. Knowledge of the identity of the biomarker also allows their isolation by immunoaffinity chromatography.

B. Use of Modified Forms of Biomarkers for Chagas Disease

It has been found that proteins frequently exist in a sample in a plurality of different forms characterized by a detectably different mass. These forms can result from either, or both, of pre- and post-translational modification. Pre-translational modified forms include allelic variants, slice variants and RNA editing forms. Post-translationally modified forms include forms resulting from proteolytic cleavage (e.g., fragments of a parent protein), glycosylation, phosphorylation, lipidation, oxidation, methylation, cystinylation, sulphonation and acetylation. The collection of proteins including a specific protein and all modified forms of it is referred to herein as a "protein cluster." The collection of all modified forms of a specific protein, excluding the specific protein, itself, is referred to herein as a "modified protein cluster." Modified forms of any biomarker of this invention (including any of biomarkers listed in Tables 1-4 and the Figures herein) also may be used, themselves, as biomarkers. In certain cases the modified forms may exhibit better discriminatory power in diagnosis than the specific forms set forth herein.

Modified forms of a biomarker, including any of the biomarkers listed in Tables 1-4 or the Figures herein, can be initially detected by any methodology that can detect and distinguish the modified from the biomarker. A preferred method for initial detection involves first capturing the biomarker and modified forms of it, e.g., with biospecific capture reagents, and then detecting the captured proteins by mass spectrometry. More specifically, the proteins are captured using biospecific capture reagents, such as antibodies, aptamers or Affibodies that recognize the biomarker and modified forms of it. This method also will also result in the capture of protein interactors that are bound to the proteins or that are otherwise recognized by antibodies and that, themselves, can be biomarkers. Preferably, the biospecific capture reagents are bound to a solid phase. Then, the captured proteins can be detected by SELDI mass spectrometry or by eluting the proteins from the capture reagent and detecting the eluted proteins by traditional MALDI or by SELDI. The use of mass spectrometry is especially attractive because it can distinguish and quantify modified forms of a protein based on mass and without the need for labeling.

Preferably, the biospecific capture reagent is bound to a solid phase, such as a bead, a plate, a membrane or a chip. Methods of coupling biomolecules, such as antibodies, to a solid phase are well known in the art. They can employ, for example, bifunctional linking agents, or the solid phase can be derivatized with a reactive group, such as an epoxide or an imidizole, that will bind the molecule on contact. Biospecific capture reagents against different target proteins can be mixed in the same place, or they can be attached to solid phases in different physical or addressable locations. For example, one can load multiple columns with derivatized beads, each column able to capture a single protein cluster. Alternatively, one can pack a single column with different beads derivatized with capture reagents against a variety of protein clusters, thereby capturing all the analytes in a single place. Accordingly, antibody-derivatized bead-based technologies, such as xMAP technology of Luminex (Austin, Tex.) can be used to detect the protein clusters. However, the biospecific capture reagents must be specifically directed toward the members of a cluster in order to differentiate them.

In yet another embodiment, the surfaces of biochips can be derivatized with the capture reagents directed against protein clusters either in the same location or in physically different addressable locations. One advantage of capturing different clusters in different addressable locations is that the analysis becomes simpler.

After identification of modified forms of a protein and correlation with the clinical parameter of interest, the modified form can be used as a biomarker in any of the methods of this invention. At this point, detection of the modified from can be accomplished by any specific detection methodology including affinity capture followed by mass spectrometry, or traditional immunoassay directed specifically the modified form. Immunoassay requires biospecific capture reagents, such as antibodies, to capture the analytes. Furthermore, if the assay must be designed to specifically distinguish protein and modified forms of protein. This can be done, for example, by employing a sandwich assay in which one antibody captures more than one form and second, distinctly labeled antibodies, specifically bind, and provide distinct detection of, the various forms. Antibodies can be produced by immunizing animals with the biomolecules. This invention contemplates traditional immunoassays including, for example, sandwich immunoassays including ELISA or fluorescence-based immunoassays, as well as other enzyme immunoassays.

III. Detection of Biomarkers for Chagas Disease

The biomarkers of this invention can be detected by any suitable method. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

"Protein biochip" refers to a biochip adapted for the capture of polypeptides. Many protein biochips are described in the art. These include, for example, protein biochips produced by Ciphergen Biosystems, Inc. (Fremont, Calif.), Packard BioScience Company (Meriden Conn.), Zyomyx (Hayward, Calif.), Phylos (Lexington, Mass.) and Biacore (Uppsala, Sweden). Examples of such protein biochips are described in the following patents or published patent applications: U.S. Pat. No. 6,225,047; PCT International Publication No. WO 99/51773; U.S. Pat. No. 6,329,209, PCT International Publication No. WO 00/56934 and U.S. Pat. No. 5,242,828.

A. Detection by Mass Spectrometry

In a preferred embodiment, the biomarkers of this invention are detected by mass spectrometry, a method that employs a mass spectrometer to detect gas phase ions. Examples of mass spectrometers are time-of-flight, magnetic sector, quadrupole filter, ion trap, ion cyclotron resonance, electrostatic sector analyzer and hybrids of these.

In a further preferred method, the mass spectrometer is a laser desorption/ionization mass spectrometer. In laser desorption/ionization mass spectrometry, the analytes are placed on the surface of a mass spectrometry probe, a device adapted to engage a probe interface of the mass spectrometer and to present an analyte to ionizing energy for ionization and introduction into a mass spectrometer. A laser desorption mass spectrometer employs laser energy, typically from an ultraviolet laser, but also from an infrared laser, to desorb analytes from a surface, to volatilize and ionize them and make them available to the ion optics of the mass spectrometer.

1. SELDI

A preferred mass spectrometric technique for use in the invention is "Surface Enhanced Laser Desorption and Ionization" or "SELDI," as described, for example, in U.S. Pat. No. 5,719,060 and No. 6,225,047, both to Hutchens and Yip. This refers to a method of desorption/ionization gas phase ion spectrometry (e.g., mass spectrometry) in which an analyte (here, one or more of the biomarkers) is captured on the surface of a SELDI mass spectrometry probe. There are several versions of SELDI.

One version of SELDI is called "affinity capture mass spectrometry." It also is called "Surface-Enhanced Affinity Capture" or "SEAC". This version involves the use of probes that have a material on the probe surface that captures analytes through a non-covalent affinity interaction (adsorption) between the material and the analyte. The material is variously called an "adsorbent," a "capture reagent," an "affinity reagent" or a "binding moiety." Such probes can be referred to as "affinity capture probes" and as having an "adsorbent surface." The capture reagent can be any material capable of binding an analyte. The capture reagent may be attached directly to the substrate of the selective surface, or the substrate may have a reactive surface that carries a reactive moiety that is capable of binding the capture reagent, e.g., through a reaction forming a covalent or coordinate covalent bond. Epoxide and carbodiimidizole are useful reactive moieties to covalently bind polypeptide capture reagents such as antibodies or cellular receptors. Nitriloacetic acid and iminodiacetic acid are useful reactive moieties that function as chelating agents to bind metal ions that interact non-covalently with histidine containing peptides. Adsorbents are generally classified as chromatographic adsorbents and biospecific adsorbents.

"Chromatographic adsorbent" refers to an adsorbent material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents).

"Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid, a nucleic acid (e.g., DNA)-protein conjugate). In certain instances, the biospecific adsorbent can be a macromolecular structure such as a multiprotein complex, a biological membrane or a virus. Examples of biospecific adsorbents are antibodies, receptor proteins and nucleic acids. Biospecific adsorbents typically have higher specificity for a target analyte than chromatographic adsorbents. Further examples of adsorbents for use in SELDI can be found in U.S. Pat. No. 6,225,047. A "bioselective adsorbent" refers to an adsorbent that binds to an analyte with an affinity of at least $10^{-8}$ M.

Protein biochips produced by Ciphergen Biosystems, Inc. comprise surfaces having chromatographic or biospecific adsorbents attached thereto at addressable locations. Ciphergen ProteinChip® arrays include NP20 (hydrophilic); H4 and H50 (hydrophobic); SAX-2, Q-10 and LSAX-30 (anion exchange); WCX-2, CM-10 and LWCX-30 (cation exchange); IMAC-3, IMAC-30 and IMAC 40 (metal chelate); and PS-10, PS-20 (reactive surface with carboimidizole, expoxide) and PG-20 (protein G coupled through carboimidizole). Hydrophobic ProteinChip arrays have isopropyl or nonylphenoxy-poly(ethylene glycol)methacrylate functionalities. Anion exchange ProteinChip arrays have quaternary ammonium functionalities. Cation exchange ProteinChip arrays have carboxylate functionalities. Immobilized metal chelate ProteinChip arrays have nitriloacetic acid functionalities that adsorb transition metal ions, such as copper, nickel, zinc, and gallium, by chelation. Preactivated ProteinChip arrays have carboimidizole or epoxide functional groups that can react with groups on proteins for covalent binding.

Such biochips are further described in: U.S. Pat. No. 6,579,719 (Hutchens and Yip, "Retentate Chromatography," Jun. 17, 2003); PCT International Publication No. WO 00/66265 (Rich et al., "Probes for a Gas Phase Ion Spectrometer," Nov. 9, 2000); U.S. Pat. No. 6,555,813 (Beecher et al., "Sample Holder with Hydrophobic Coating for Gas Phase Mass Spectrometer," Apr. 29, 2003); U.S. patent application No. U.S. 2003 0032043 A1 (Pohl and Papanu, "Latex Based Adsorbent Chip," Jul. 16, 2002); and PCT International Publication No. WO 03/040700 (Um et al., "Hydrophobic Surface Chip," May 15, 2003); U.S. Provisional Patent Application No. 60/367,837 (Boschetti et al., "Biochips With Surfaces Coated With Polysaccharide-Based Hydrogels," May 5, 2002) and the U.S. patent application entitled "Photocrosslinked Hydrogel Surface Coatings" (Huang et al., filed Feb. 21, 2003).

In general, a probe with an adsorbent surface is contacted with the sample for a period of time sufficient to allow biomarker or biomarkers that may be present in the sample to bind to the adsorbent. After an incubation period, the substrate is washed to remove unbound material. Any suitable washing solutions can be used; preferably, aqueous solutions are employed. The extent to which molecules remain bound can be manipulated by adjusting the stringency of the wash. The elution characteristics of a wash solution can depend, for example, on pH, ionic strength, hydrophobicity, degree of chaotropism, detergent strength, and temperature. Unless the probe has both SEAC and SEND properties (as described herein), an energy absorbing molecule then is applied to the substrate with the bound biomarkers.

The biomarkers bound to the substrates are detected in a gas phase ion spectrometer such as a time-of-flight mass spectrometer. The biomarkers are ionized by an ionization source such as a laser, the generated ions are collected by an ion optic assembly, and then a mass analyzer disperses and analyzes the passing ions. The detector then translates information of the detected ions into mass-to-charge ratios. Detection of a biomarker typically will involve detection of signal intensity. Thus, both the quantity and mass of the biomarker can be determined.

Another version of SELDI is Surface-Enhanced Neat Desorption (SEND), which involves the use of probes comprising energy absorbing molecules that are chemically bound to the probe surface ("SEND probe"). The phrase "energy absorbing molecules" (EAM) denotes molecules that are capable of absorbing energy from a laser desorption/ionization source and, thereafter, contribute to desorption and ionization of analyte molecules in contact therewith. The EAM category includes molecules used in MALDI, frequently referred to as "matrix," and is exemplified by cinnamic acid derivatives, sinapinic acid (SPA), cyano-hydroxy-cinnamic acid (CHCA) and dihydroxybenzoic acid, ferulic acid, and hydroxyacetophenone derivatives. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-ethoxy)silyl propyl methacrylate. In another embodiment, the composition is a co-polymer of α-cyano-4-methacryloyloxycinnamic acid and octadecylmethacrylate ("C18 SEND"). SEND is further described in U.S. Pat. No. 6,124,137 and PCT International Publication No. WO 03/64594 (Kitagawa, "Monomers And Polymers Having Energy Absorbing Moieties Of Use In Desorption/Ionization Of Analytes," Aug. 7, 2003).

SEAC/SEND is a version of SELDI in which both a capture reagent and an energy absorbing molecule are attached to the sample presenting surface. SEAC/SEND probes therefore allow the capture of analytes through affinity capture and ionization/desorption without the need to apply external matrix. The C18 SEND biochip is a version of SEAC/SEND, comprising a C18 moiety which functions as a capture reagent, and a CHCA moiety which functions as an energy absorbing moiety.

Another version of SELDI, called Surface-Enhanced Photolabile Attachment and Release (SEPAR), involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker profile, pursuant to the present invention.

2. Other Mass Spectrometry Methods

In another mass spectrometry method, the biomarkers can be first captured on a chromatographic resin having chromatographic properties that bind the biomarkers. In the present example, this could include a variety of methods. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

3. Data Analysis

Analysis of analytes by time-of-flight mass spectrometry generates a time-of-flight spectrum. The time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation to generate a mass spectrum, baseline subtraction to eliminate instrument offsets and high frequency noise filtering to reduce high frequency noise.

Data generated by desorption and detection of biomarkers can be analyzed with the use of a programmable digital computer. The computer program analyzes the data to indicate the number of biomarkers detected, and optionally the strength of the signal and the determined molecular mass for each biomarker detected. Data analysis can include steps of determining signal strength of a biomarker and removing data deviating from a predetermined statistical distribution. For example, the observed peaks can be normalized, by calculating the height of each peak relative to some reference. The reference can be background noise generated by the instrument and chemicals such as the energy absorbing molecule which is set at zero in the scale.

The computer can transform the resulting data into various formats for display. The standard spectrum can be displayed, but in one useful format only the peak height and mass information are retained from the spectrum view, yielding a cleaner image and enabling biomarkers with nearly identical molecular weights to be more easily seen. In another useful format, two or more spectra are compared, conveniently highlighting unique biomarkers and biomarkers that are up- or down-regulated between samples. Using any of these formats, one can readily determine whether a particular biomarker is present in a sample.

Analysis generally involves the identification of peaks in the spectrum that represent signal from an analyte. Peak selection can be done visually, but software is available, as part of Ciphergen's ProteinChip® software package, that can automate the detection of peaks. In general, this software functions by identifying signals having a signal-to-noise ratio above a selected threshold and labeling the mass of the peak at the centroid of the peak signal. In one useful application, many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Software used to analyze the data can include code that applies an algorithm to the analysis of the signal to determine whether the signal represents a peak in a signal that corresponds to a biomarker according to the present invention. The software also can subject the data regarding observed biomarker peaks to classification tree or ANN analysis, to determine whether a biomarker peak or combination of biomarker peaks is present that indicates the status of the particular clinical parameter under examination. Analysis of the data may be "keyed" to a variety of parameters that are obtained, either directly or indirectly, from the mass spectrometric analysis of the sample. These parameters include, but are not limited to, the presence or absence of one or more peaks, the shape of a peak or group of peaks, the height of one or more peaks, the log of the height of one or more peaks, and other arithmetic manipulations of peak height data.

4. General Protocol for SELDI Detection of Biomarkers for Chagas Disease

A preferred protocol for the detection of the biomarkers of this invention is as follows. The biological sample to be tested, e.g., serum, preferably is subject to pre-fractionation before SELDI analysis. This simplifies the sample and improves sensitivity. Prior to the pre-fractionation, the serum (20 ul) is denatured using a 9 M urea/2% Chaps/50 mM Tris pH 9.0 buffer (U9 buffer). 30 µl of U9 is added to the 20 µl of serum and then this diluted serum is subjected to anion exchange fractionation. A preferred method of pre-fractionation involves contacting the sample with an anion exchange chromatographic material, such as Q HyperD (BioSepra, SA, a division of Ciphergen Biosystems, Inc.). The bound materials are then subject to stepwise pH elution using buffers at pH 9, pH 7, pH 5, pH 4 and pH 3. (See Example 1—Buffer list) as well as an organic solvent elution (The fractions in which the biomarkers are eluted are also indicated in Tables 1-4 and in the Figures by reference to the Marker IDs, e.g. F1IH_# F2WSL_#, etc.). Various fractions containing the biomarker are collected.

The sample to be tested (preferably pre-fractionated) is then contacted with an affinity capture probe comprising a cation exchange adsorbent (preferably a WCX ProteinChip array (Ciphergen Biosystems, Inc.)) or an IMAC adsorbent (preferably an IMAC3 ProteinChip array (Ciphergen Biosystems, Inc.)), again as indicated in the Marker IDs listed in Tables 1-4 and in the Figures. The probe is washed with a buffer that will retain the biomarker while washing away unbound molecules. Suitable washes for each chip are described in the Example. The biomarkers are detected by laser desorption/ionization mass spectrometry.

Alternatively, if antibodies that recognize the biomarker are available, for example in the case of MIP-1 a, these can be attached to the surface of a probe, such as a pre-activated PS10 or PS20 ProteinChip array (Ciphergen Biosystems, Inc.). These antibodies can capture the biomarkers from a sample onto the probe surface. Then the biomarkers can be detected by, e.g., laser desorption/ionization mass spectrometry.

B. Detection by Immunoassay

In another embodiment, the biomarkers of this invention can be measured by immunoassay. Immunoassay requires biospecific capture reagents, such as antibodies, to capture the biomarkers. Antibodies can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well known in the art.

This invention contemplates traditional immunoassays including, for example, sandwich immunoassays including ELISA or fluorescence-based immunoassays, as well as other enzyme immunoassays. In the SELDI-based immunoassay, a biospecific capture reagent for the biomarker is attached to the surface of an MS probe, such as a pre-activated ProteinChip array. The biomarker is then specifically captured on the biochip through this reagent, and the captured biomarker is detected by mass spectrometry.

IV. Determination of Subject Chagas Disease Status

A. Single Markers

The biomarkers of the invention can be used in diagnostic tests to assess Chagas disease status in a subject, e.g., to diagnose Chagas disease. The phrase "Chagas disease status" includes distinguishing, inter alia, chronic Chagas disease versus non-Chagas disease and, in particular, chronic asymptomatic Chagas disease versus non-infection or acute Chagas disease status versus non-infection. Based on this status, further procedures may be indicated, including additional diagnostic tests or therapeutic procedures or regimens.

The power of a diagnostic test to correctly predict status is commonly measured as the sensitivity of the assay, the specificity of the assay or the area under a receiver operated characteristic ("ROC") curve. Sensitivity is the percentage of true positives that are predicted by a test to be positive, while specificity is the percentage of true negatives that are predicted by a test to be negative. An ROC curve provides the sensitivity of a test as a function of 1-specificity. The greater the area under the ROC curve, the more powerful the predictive value of the test. Other useful measures of the utility of a test are positive predictive value and negative predictive value. Positive predictive value is the percentage of actual positives who test as positive. Negative predictive value is the percentage of actual negatives that test as negative.

The biomarkers of this invention show a statistical difference in different Chagas disease statuses of at least $p \leq 0.05$, $p \leq 10^{-2}$, $p \leq 10^{-3}$, $p \leq 10^{-4}$ or $p \leq 10^{-5}$. Diagnostic tests that use these biomarkers alone or in combination show a sensitivity and specificity of at least 75%, at least 80%, at least 85%, at least 90%, at least 95%, at least 98% and about 100%.

Each biomarker listed in Tables 1-4 and the Figures is differentially present in Chagas disease, and, therefore, each is individually useful in aiding in the determination of Chagas disease status. The method involves, first, measuring the selected biomarker in a subject sample using the methods described herein, e.g., capture on a SELDI biochip followed by detection by mass spectrometry and, second, comparing the measurement with a diagnostic amount or cut-off that distinguishes a positive Chagas disease status from a negative Chagas disease status. The diagnostic amount represents a measured amount of a biomarker above which or below which a subject is classified as having a particular Chagas disease status. For example, if the biomarker is up-regulated compared to normal during Chagas disease, then a measured amount above the diagnostic cut-off provides a diagnosis of Chagas disease. Alternatively, if the biomarker is down-regulated during Chagas disease, then a measured amount below the diagnostic cutoff provides a diagnosis of Chagas disease. As is well understood in the art, by adjusting the particular diagnostic cut-off used in an assay, one can increase sensitivity or specificity of the diagnostic assay depending on the preference of the diagnostician. The particular diagnostic cut-off can be determined, for example, by measuring the amount of the biomarker in a statistically significant number of samples from subjects with the different Chagas disease statuses, as was done here, and drawing the cut-off to suit the diagnostician's desired levels of specificity and sensitivity.

B. Combinations of Markers

While individual biomarkers are useful diagnostic biomarkers, it has been found that a combination of biomarkers can provide greater predictive value of a particular status than single biomarkers alone. Specifically, the detection of a plurality of biomarkers in a sample can increase the sensitivity and/or specificity of the test.

For example, the protocols described in Example 1 below were used to generate mass spectra from 73 Venezuelan patient samples. Of these 73 samples, 39 of the samples were obtained from patients chronically infected with Chagas disease and 34 were taken from healthy individuals living in the same endemic region. The peak masses and heights were abstracted into a discovery data set. This data set was used to train a learning algorithm employing classification and regression tree analysis (CART) (Ciphergen Biomarker Patterns Software™. In particular, CART chose many subsets of the peaks at random. For each subset, CART generated a best or near best decision tree to classify a sample as Chagas disease or non-Chagas disease. Among the many decision trees generated by CART, several had excellent sensitivity and specificity in distinguishing Chagas disease from non-Chagas disease.

Figure 3A:
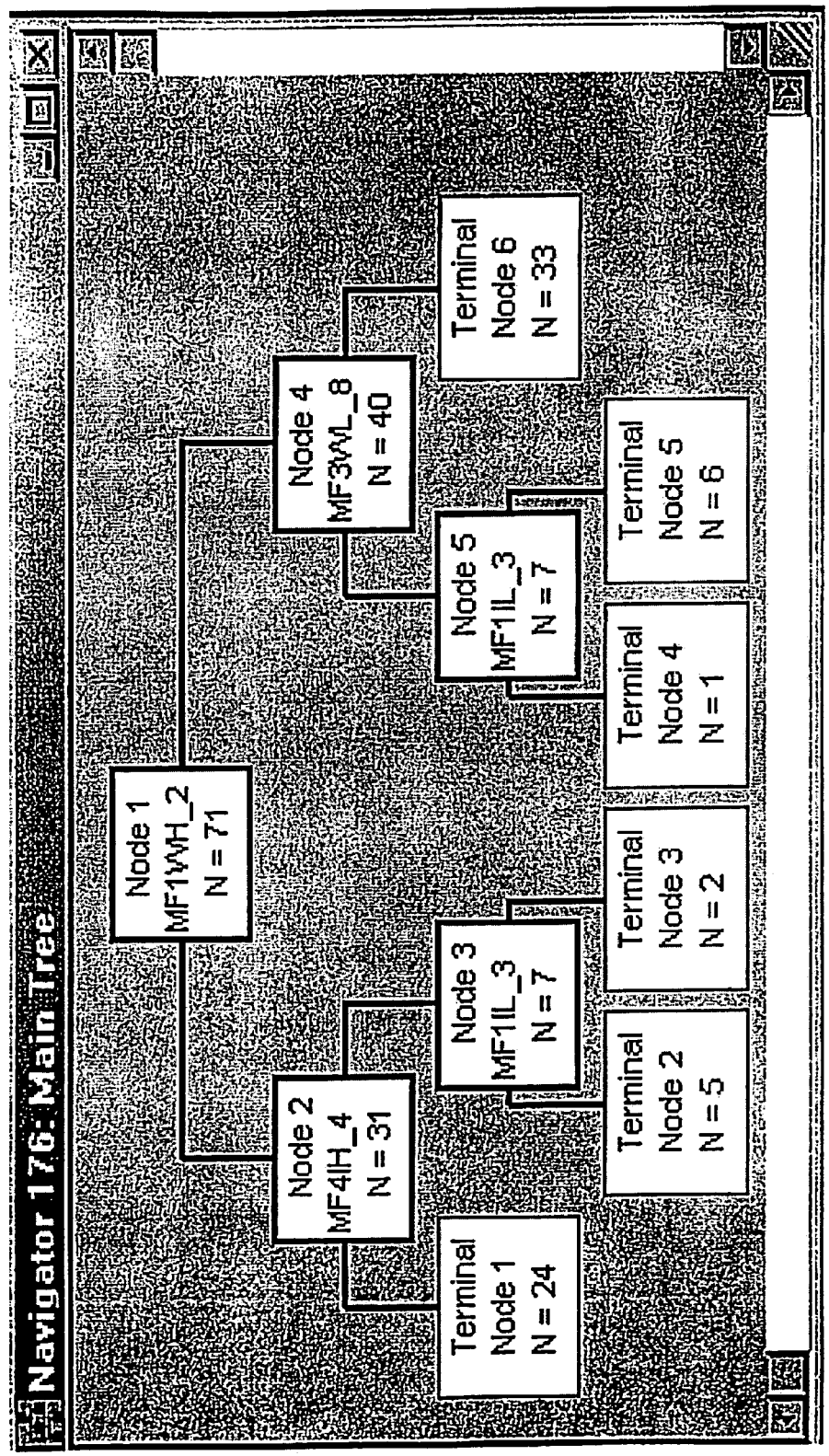
FIG. 3A-B shows the results of multivariate analyses utilizing five biomarkers to determine Chagas disease status. The detection of two or more biomarkers expressed independently of each other provides higher degrees of sensitivity and specificity for Chagas disease than may be provided by the detection of any single biomarker. The biomarkers used for the analysis shown in FIG. 3A-B are referred to in the figure by their marker IDs, by reference to Table 1.
Figure 3B:
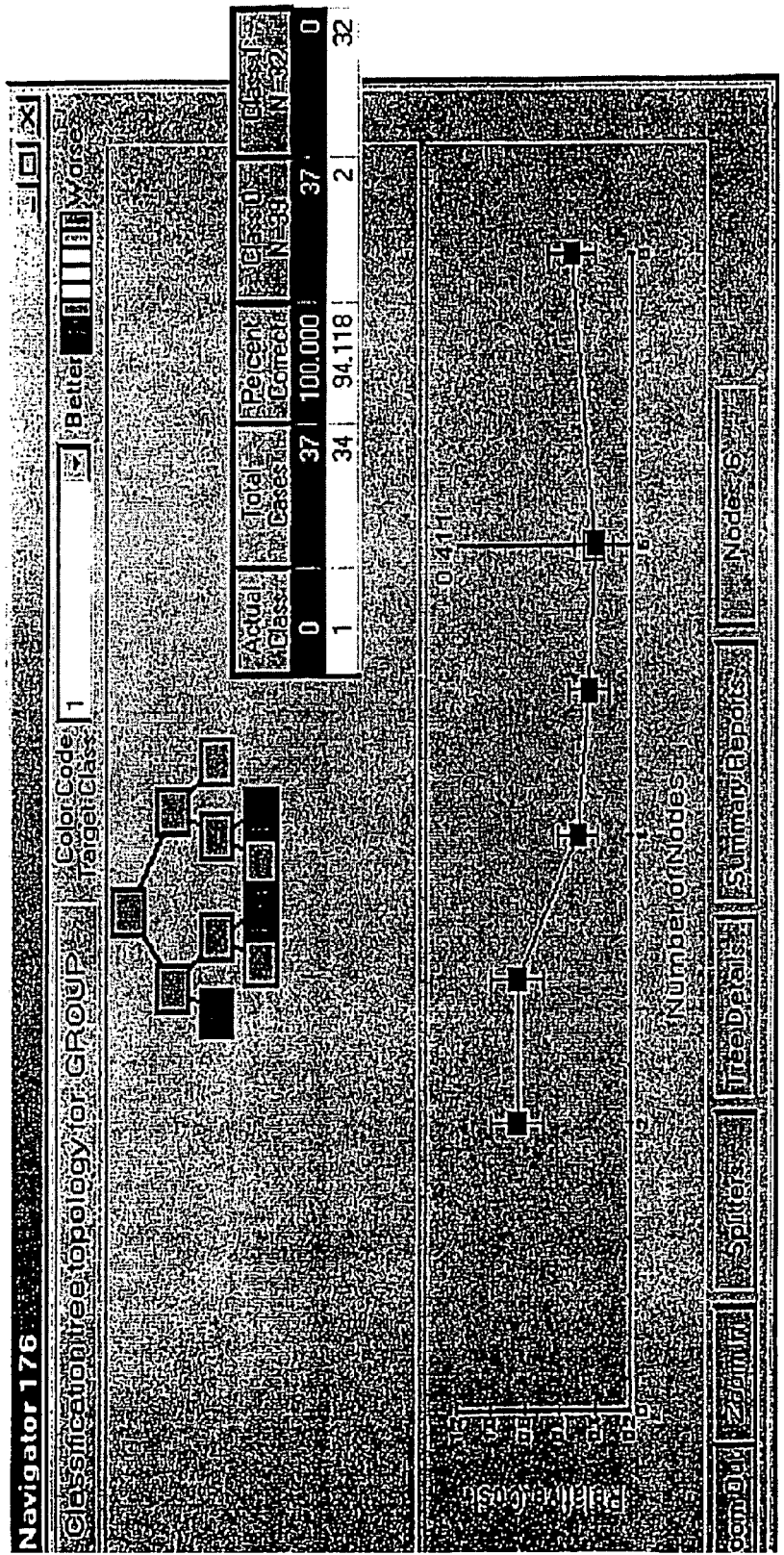
Figure 4:
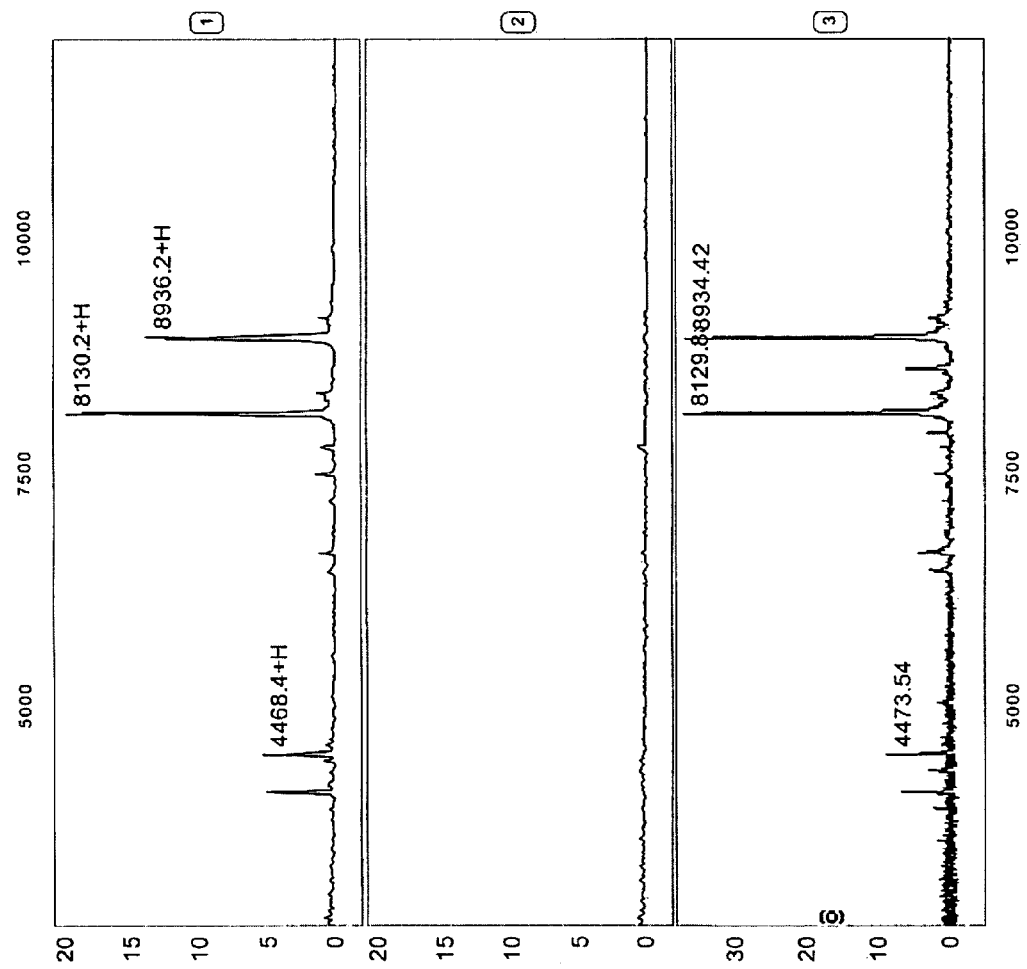
FIG. 4 shows a mass spectrophotometric analysis confirming the identity of the 8.1 kDa protein which was detected in fraction 1 on IMAC-Cu and WCX arrays using SPA as the EAM. Panels 1 and 2 show the spectrum of proteins bound by anti-C3a antibodies and control mouse IgG antibodies, respectively. The antibodies were coupled to Protein A HyperD beads. Panel 3 shows the spectrum from the discovery phase of the study. The blood sample was fractionated using anion exchange chromatography and Fraction 1 was profiled using a WCX array (low laser energy). The proteins utilized in the model are indicated by their marker IDs, by reference to Table 1, as follows: F1WH_2 (C-terminal fragment of ApoA1 (amino acids 124-243); F3WL_8 C-terminal truncation of C3 anaphylatoxin (amino acids 1-68); F41H 4, N-terminal fragment of ApoA1 (amino acids 1-214); F1IL_3 (Double-charged peak of C3 anaphylatoxin des Arg (amino acids 1-76).

An exemplary decision tree for qualifying the Chagas disease status of a sample taken from a subject is presented in FIG. 3. The identity of the biomarkers used is indicated in FIG. 3, by reference to Table 1. For example, the biomarker in "Node 1" in FIG. 3 is F1WH_2, corresponding to the Chagas disease biomarker with an estimated mass of 13.6 kD. The specificity and sensitivity of the multiple-biomarker analysis increases as the number of biomarkers in the decision tree is increased. FIG. 4B shows that 100% specificity and greater than 94% sensitivity can be achieved using the 5 biomarkers selected in this example. The sensitivity of the decision tree analysis is shown in an inset table in the Figure under the column "Percent Correct" and in the row Actual Class="0". The specificity is shown in the same column in the row Actual Class="1".

It is also noted that the specifics of the decision trees, in particular the cut-off values used in making branching decisions, depends on the details of the assay used to generate the discovery data set. The data acquisition parameters of the assay that produced the data used in the present analysis is provided in the Example. In developing a classification algorithm from, for example, a new sample set or a different assay protocol, the operator uses a protocol that detects these biomarkers and keys the learning algorithm to include them.

C. Biomarkers Specific to Chagas Disease

The methods further provide for specifically qualifying Chagas disease status in a subject in comparison to the status of a different parasitic disease (i.e., a non-Chagas disease), the method comprising: (a) measuring at least one biomarker in a biological sample from the subject, wherein the at least one biomarker specifically indicates the presence of Chagas disease and does not indicate the presence of a different parasitic infection; and (b) correlating the measurement with Chagas disease status in comparison to the status of a different parasitic infection. In one embodiment, the biological sample is a serum sample.

Figure 7:
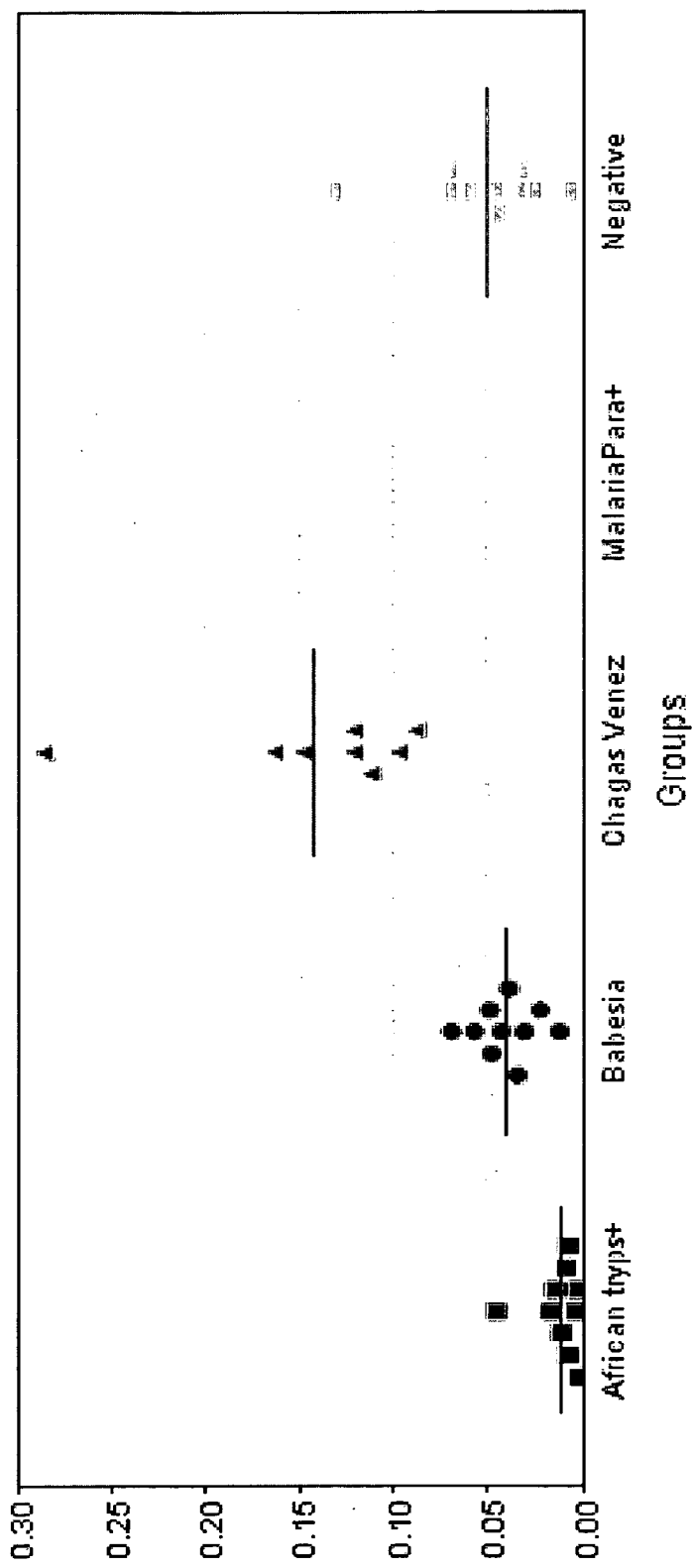
FIG. 7 shows the differential signal intensity of a 8.351 kDa peptide in Venezuelan patients infected with Chagas compared to uninfected healthy individuals and individuals infected with different parasitic diseases, here African trypanosomiasis (sleeping sickness), malaria, and babesiosis.
Figure 8:
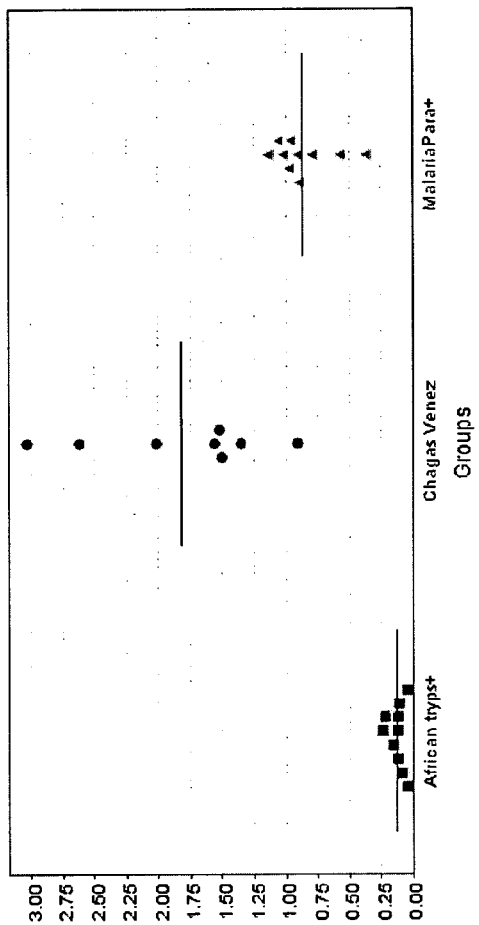
FIG. 8 shows the differential signal intensity of a 9.3 kDa peptide in Venezuelan patients infected with Chagas compared to individuals infected with a different parasitic diseases, here African trypanosomiasis (sleeping sickness) and malaria.
Figure 9A:
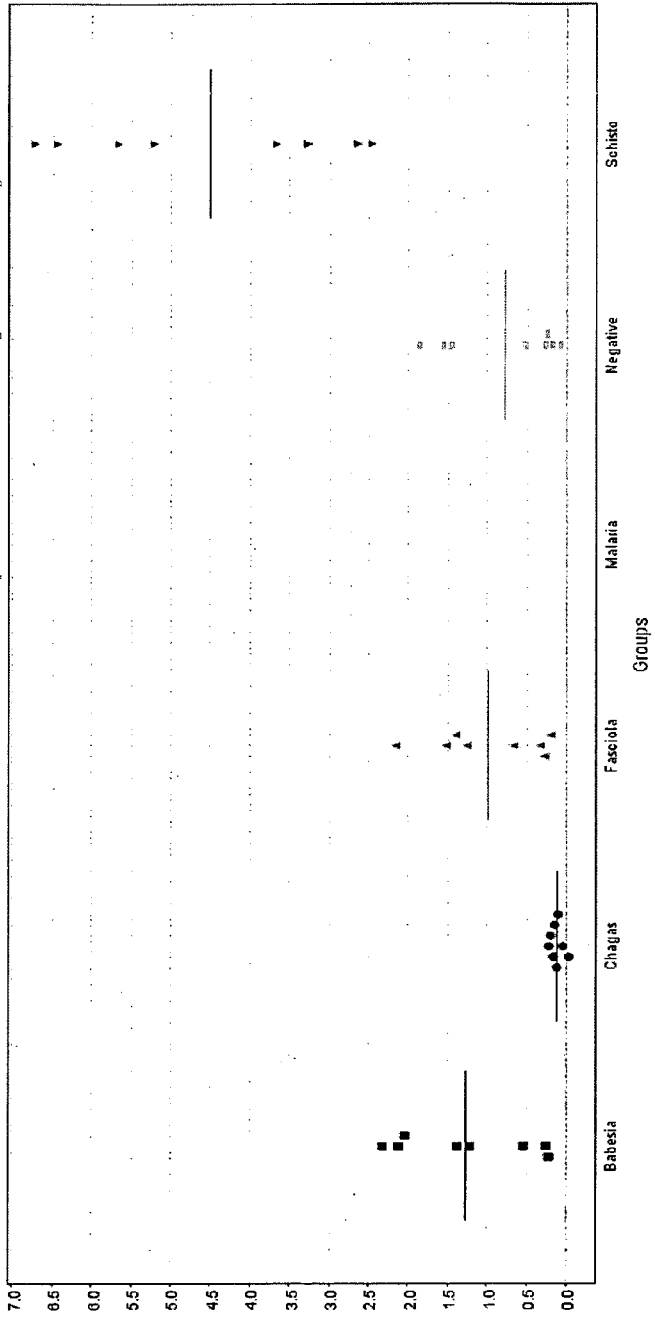
FIG. 9A-E demonstrates applying the methods of the present patent application to the identification of biomarkers indicating the status of other parasitic diseases, for example helminth infections, including biomarkers indicative of infection with organisms such as *Fasciola hepatica, Schistosoma mansoni, Strongyloides stercoralis, Echinococcus granulosis, Trichinella nativa, Filaria, Cysticercosis* and *Toxocara*.
Figure 9B:
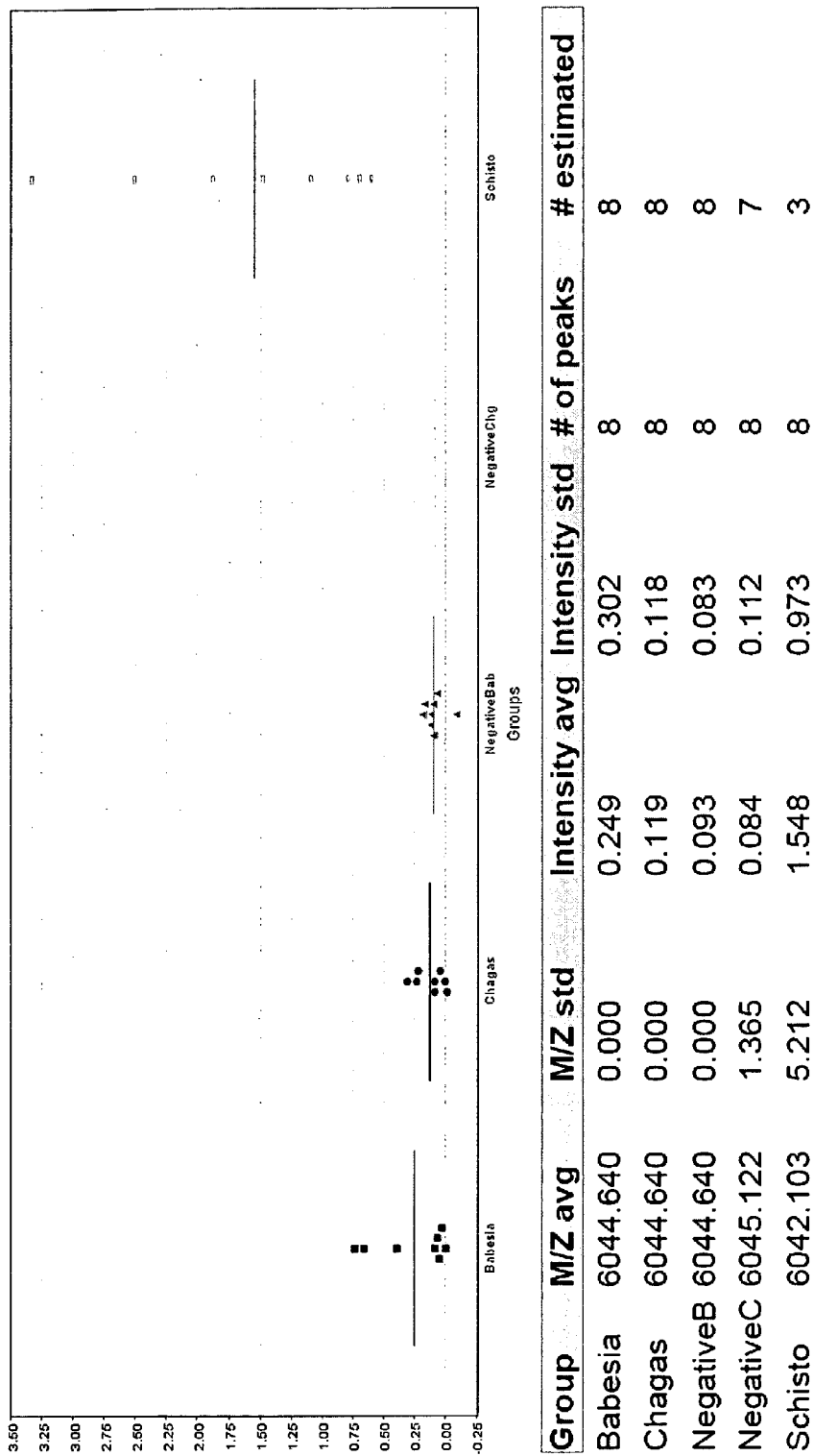
Figure 9C:
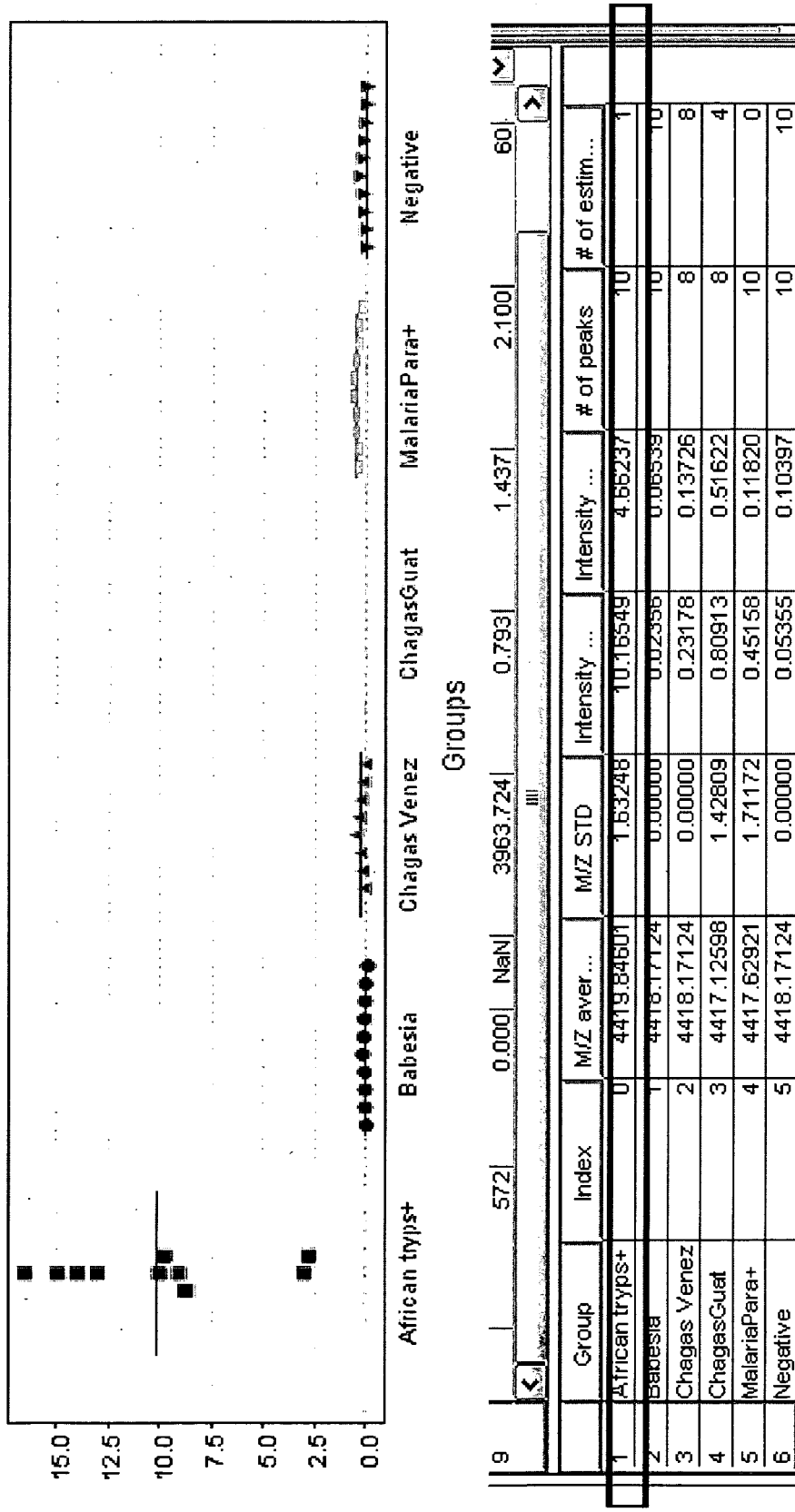
Figure 9D:
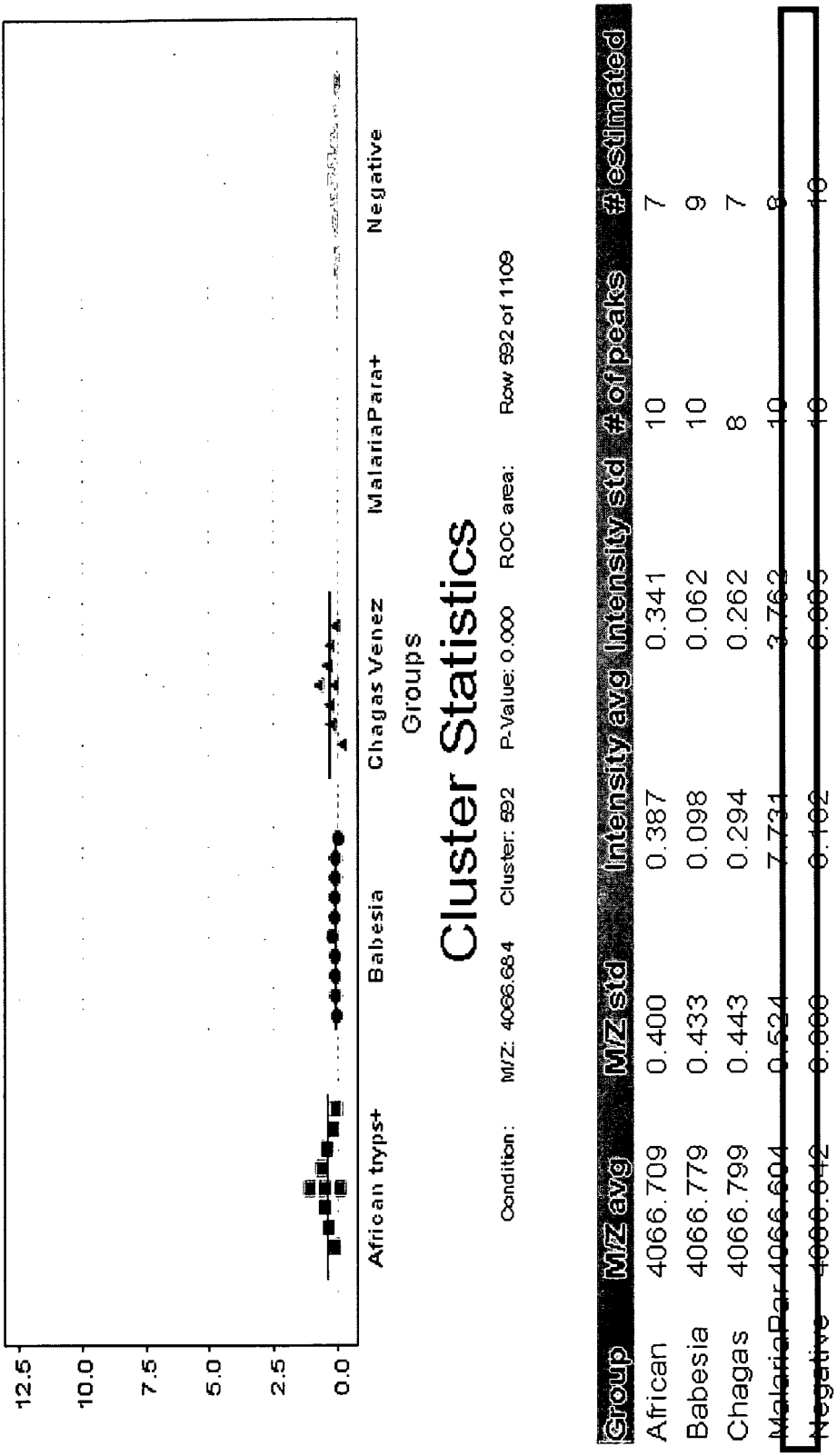
Figure 9E:
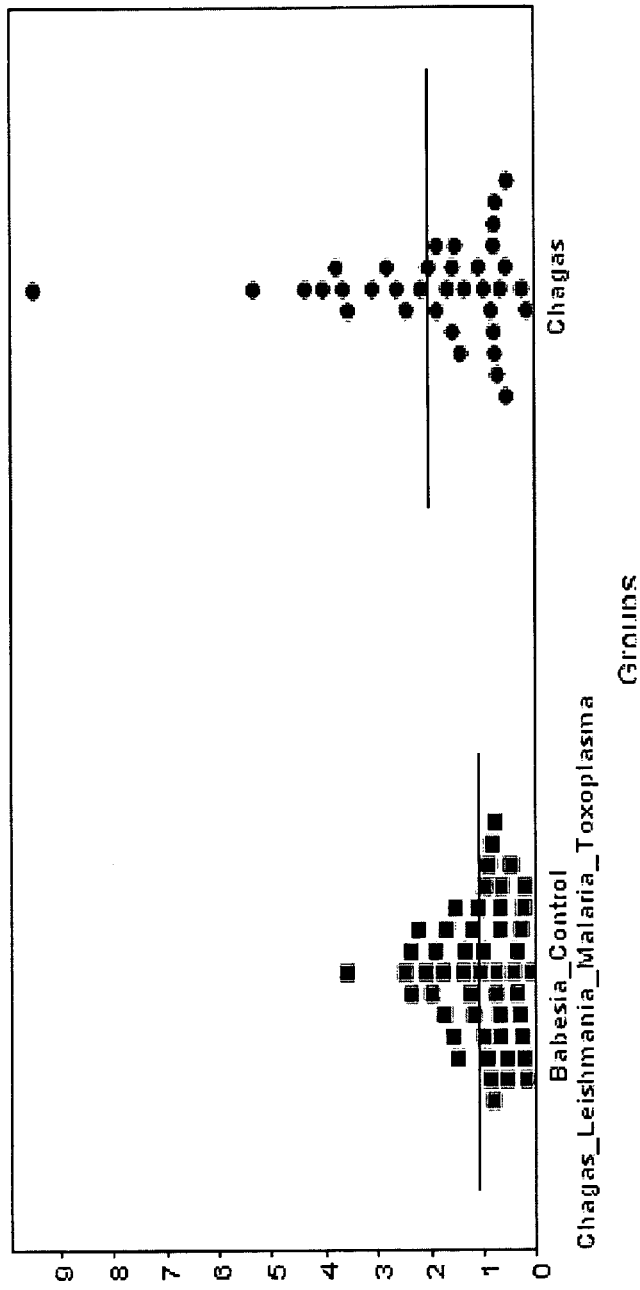

In one embodiment, the biomarkers specifically identify the presence or absence of Chagas disease as distinguished from a different parasitic infection, including a protozoa, a helminth or a malarial infection. In one embodiment, the biomarkers specifically identify the presence or absence of Chagas disease as distinguished from other protozoal infections, including Leishmaniasis, African trypanosomiasis (sleeping sickness) and babesiosis. In one embodiment, the biomarkers specifically identify the presence or absence of Chagas disease as distinguished from other kinetoplastidae or trypanosomal infections, including Leishmaniasis and African trypanosomiasis. In one embodiment, the biomarkers specifically identify the presence or absence of an infection with *T. cruzi* as distinguished from an infection with *T. brucei*, including *T. brucei* rhodesiense and *T. brucei* gambiense. In one embodiment, the biomarkers that specifically identify the presence or absence of a Chagas disease infection as distinguished from another parasitic disease are selected from the group consisting of biomarkers of molecular weight 8.351 kDa, 9.3 kDa, 7.3 kDa, 6.04 kDa, 4.4 kDa, 4.07 kDa and 5.1 kDa, as depicted in FIGS. 7-9. The presence of a biomarker specific for Chagas disease, or the presence of a biomarker specific for Chagas disease above (or below) a cut-off level (i.e., a comparatively greater or lesser presence of one or more of the biomarkers), is indicative of infection by *T. cruzi* and is indicative of Chagas disease in an individual.

D. Determining Risk of Developing Disease

In one embodiment, this invention provides methods for determining the risk of developing Chagas disease in a subject. Biomarker amounts or patterns are characteristic of various risk states, e.g., high, medium or low. The risk of developing Chagas disease is determined by measuring the relevant biomarker or biomarkers and then either submitting them to a classification algorithm or comparing them with a reference amount and/or pattern of biomarkers that is associated with the particular risk level.

E. Determining Stage of Disease

In one embodiment, this invention provides methods for determining the stage of Chagas disease in a subject. Each stage of Chagas disease has a characteristic amount of a biomarker or relative amounts of a set of biomarkers (a pattern). The stage of Chagas disease is determined by measuring the relevant biomarker or biomarkers and then either submitting them to a classification algorithm or comparing them with a reference amount and/or pattern of biomarkers that is associated with the particular stage.

F. Determining Course (Progression/Remission) of Disease

In one embodiment, this invention provides methods for determining the course of disease in a subject. Disease course refers to changes in disease status over time, including disease progression (worsening) and disease regression (improvement). Over time, the amounts or relative amounts (e.g., the pattern) of the biomarkers changes. For example, certain biomarkers increase with Chagas disease progresson or regression, while other biomarkers decrease with Chagas disease progression or regression. Therefore, the trend of these markers, either increased or decreased over time toward diseased or non-diseased indicates the course of the disease. Accordingly, this method involves measuring one or more biomarkers in a subject at at least two different time points, e.g., a first time and a second time, and comparing the change in amounts, if any. The course of Chagas disease is determined based on these comparisons. Similarly, this method is useful for determining the response to treatment. If a treatment is effective, then the biomarkers will trend toward normal, while if treatment is ineffective, the biomarkers will trend toward disease indications.

G. Subject Management

In certain embodiments of the methods of qualifying Chagas disease status, the methods further comprise managing subject treatment based on the status. Such management includes the actions of the physician or clinician subsequent to determining Chagas disease status. For example, if a physician makes a diagnosis of Chagas disease, then a certain regime of treatment may be administered, such as drugs shown to be effective in the treatment of Chagas disease, such as nifurtimox, benznidazole or allopurinol. Alternatively, a negative diagnosis of Chagas disease in an individual exhibiting Chagas-associated symptoms might be followed with further testing to determine if the patient is suffering from an infection by a parasite related to *T. cruzi* or an illness unrelated to infection by a trypanosome. If the diagnostic test gives an inconclusive result on Chagas disease status, further tests may be called for.

Additional embodiments of the invention relate to the communication of assay results or diagnoses or both to technicians, physicians or patients, for example. In certain embodiments, computers will be used to communicate assay results or diagnoses or both to interested parties, e.g., physicians and their patients. In some embodiments, the assays will be performed or the assay results analyzed in a country or jurisdiction which differs from the country or jurisdiction to which the results or diagnoses are communicated.

In a preferred embodiment of the invention, a diagnosis based on the presence or absence in a test subject of any of the biomarkers listed in Table 1-4 or in the Figures is communicated to the subject as soon as possible after the diagnosis is obtained. The diagnosis may be communicated to the subject by the subject's treating physician. Alternatively, the diagnosis may be sent to a test subject by email or communicated to the subject by phone. A computer may be used to communicate the diagnosis by email or phone. In certain embodiments, the message containing results of a diagnostic test may be generated and delivered automatically to the subject using a combination of computer hardware and software which will be familiar to artisans skilled in telecommunications. One example of a healthcare-oriented communications system is described in U.S. Pat. No. 6,283,761; however, the present invention is not limited to methods which utilize this particular communications system. In certain embodiments of the methods of the invention, all or some of the method steps, including the assaying of samples, diagnosing of diseases, and communicating of assay results or diagnoses, may be carried out in diverse (e.g., foreign) jurisdictions.

V. Generation of Classification Algorithms for Qualifying Chagas Disease Status

In some embodiments, data derived from the spectra (e.g., mass spectra or time-of-flight spectra) that are generated using samples such as "known samples" can then be used to "train" a classification model. A "known sample" is a sample that has been pre-classified. The data that are derived from the spectra and are used to form the classification model can be referred to as a "training data set." Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., Chagas disease versus uninfected, or asymptomatic Chagas diseased versus acute Chagas disease).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", *IEEE Transactions on Pattern Analysis and Machine Intelligence*, Vol. 22, No. 1, January 2000, the teachings of which are incorporated by reference.

In supervised classification, training data containing examples of known categories are presented to a learning mechanism, which learns one or more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are provided in U.S. patent application No. 2002 0138208 A1 to Paulse et al., "Method for analyzing mass spectra."

In other embodiments, the classification models that are created can be formed using unsupervised learning methods. Unsupervised classification attempts to learn classifications based on similarities in the training data set, without pre-classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

Learning algorithms asserted for use in classifying biological information are described, for example, in PCT International Publication No. WO 01/31580 (Barnhill et al., "Methods and devices for identifying patterns in biological systems and methods of use thereof"), U.S. patent application No. 2002 0193950 A1 (Gavin et al., "Method or analyzing mass spectra"), U.S. patent application No. 2003 0004402 A1 (Hitt et al., "Process for discriminating between biological states based on hidden patterns from biological data"), and U.S. patent application No. 2003 0055615 A1 (Zhang and Zhang, "Systems and methods for processing biological expression data").

The classification models can be formed on and used on any suitable digital computer. Suitable digital computers include micro, mini, or large computers using any standard or specialized operating system, such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

The learning algorithms described above are useful both for developing classification algorithms for the biomarkers already discovered, or for finding new biomarkers for Chagas disease. The classification algorithms, in turn, form the base for diagnostic tests by providing diagnostic values (e.g., cut-off points) for biomarkers used singly or in combination.

VI. Kits for Detection of Biomarkers for Chagas Disease

In another aspect, the present invention provides kits for qualifying Chagas disease status, which kits are used to detect biomarkers according to the invention. In one embodiment, the kit comprises a solid support, such as a chip, a microtiter plate or a bead or resin having a capture reagent attached thereon, wherein the capture reagent binds a biomarker of the invention. Thus, for example, the kits of the present invention can comprise mass spectrometry probes for SELDI, such as ProteinChip® arrays. In the case of biospecfic capture reagents, the kit can comprise a solid support with a reactive surface, and a container comprising the biospecific capture reagent.

The kit can also comprise a washing solution or instructions for making a washing solution, in which the combination of the capture reagent and the washing solution allows capture of the biomarker or biomarkers on the solid support for subsequent detection by, e.g., mass spectrometry. The kit may include more than type of adsorbent, each present on a different solid support.

In a further embodiment, such a kit can comprise instructions for suitable operational parameters in the form of a label or separate insert. For example, the instructions may inform a consumer about how to collect the sample, how to wash the probe or the particular biomarkers to be detected.

In yet another embodiment, the kit can comprise one or more containers with biomarker samples, to be used as standard(s) for calibration.

VII. Use of Biomarkers for Chagas Disease in Screening Assays

The methods of the present invention have other applications as well. For example, the biomarkers can be used to screen for compounds that modulate the expression of the biomarkers in vitro or in vivo, which compounds in turn may be useful in treating or preventing Chagas disease in patients. In another example, the biomarkers can be used to monitor the response to treatments for Chagas disease. In yet another example, the biomarkers can be used in heredity studies to determine if the subject is at risk for developing Chagas disease.

Thus, for example, the kits of this invention could include a solid substrate having an cation exchange function, such as a protein biochip (e.g., a Ciphergen WCX2 ProteinChip array) and a sodium acetate buffer for washing the substrate, as well as instructions providing a protocol to measure the biomarkers of this invention on the chip and to use these measurements to diagnose Chagas disease.

Compounds suitable for therapeutic testing may be screened initially by identifying compounds which interact with one or more biomarkers listed in Tables 1-4 or in the Figures herein. By way of example, screening might include recombinantly expressing a biomarker listed in Table 1-4 or in the Figures, purifying the biomarker, and affixing the biomarker to a substrate. Test compounds would then be contacted with the substrate, typically in aqueous conditions, and interactions between the test compound and the biomarker are measured, for example, by measuring elution rates as a function of salt concentration. Certain proteins may recognize and cleave one or more biomarkers of Tables 1-4, in which case the proteins may be detected by monitoring the digestion of one or more biomarkers in a standard assay, e.g., by gel electrophoresis of the proteins.

In a related embodiment, the ability of a test compound to inhibit the activity (i.e., non-enzymatic or enzymatic) of one or more of the biomarkers of Table 1-4 or the Figures may be measured. One of skill in the art will recognize that the techniques used to measure the activity of a particular biomarker will vary depending on the function and properties of the biomarker. For example, an enzymatic activity of a biomarker may be assayed provided that an appropriate substrate is available and provided that the concentration of the substrate or the appearance of the reaction product is readily measurable. The ability of potentially therapeutic test compounds to inhibit or enhance the activity of a given biomarker may be determined by measuring the rates of catalysis in the presence or absence of the test compounds. The ability of a test compound to interfere with a non-enzymatic (e.g., structural) function or activity of one of the biomarkers of Table 1-4 or of the Figures may also be measured. For example, the self-assembly of a multi-protein complex which includes one of the biomarkers described herein may be monitored by spectroscopy in the presence or absence of a test compound.

Test compounds capable of modulating the activity or expression of any of the biomarkers described in Tables 1-4 or the Figures may be administered to patients who are suffering from or are at risk of developing Chagas disease. For example, the administration of a test compound which increases the activity of a particular biomarker may diminish the symptoms of Chagas disease in a patient if the activity of the particular biomarker in vivo prevents the accumulation of harmful metabolites associated with Chagas disease. Conversely, the administration of a test compound which decreases the activity or expression of a particular biomarker may diminish or alleviate the symptoms of Chagas disease in a patient if the increased activity or expression is responsible, at least in part, for the onset of Chagas disease or for the ability of the parasite to propogate and effectuate the disease state in a patient.

In an additional aspect, the invention provides a method for identifying compounds useful for the treatment of disorders such as Chagas disease which are associated with increased levels of modified forms of the biomarkers listed in the Tables herein or the full-length biomarker proteins. For example, in one embodiment, cell extracts or expression libraries may be screened for compounds which inhibit the cleavage of the full-length proteins associated with the biomarkers listed in the Tables, including MIP-1a, M 10, Apo 1A, Fibronectin, and C3 anaphylatoxin, to form truncated forms of these biomarker proteins. In one embodiment of such a screening assay, cleavage of biomarker proteins, including MIP-1 a, M 110, Apo 1A, Fibronectin, and C3 anaphylatoxin, may be detected by attaching a fluorophore to the biomarker protein which remains quenched when the biomarker protein is uncleaved but which fluoresces when the protein is cleaved. Alternatively, a version of a full-length biomarker protein, including MIP-1a, M110, Apo 1A, Fibronectin, and C3 anaphylatoxin, or any other biomarker described herein may be modified so as to render the amide bond between amino acids x and y uncleavable may be used to selectively bind or "trap" the cellular protease which cleaves full-length biomarker protein at that site in vivo. Methods for screening and identifying proteases and their targets are well-documented in the scientific literature, e.g., in Lopez-Ottin et al. (Nature Reviews, 3:509-519 (2002)).

In yet another embodiment, the invention provides a method for treating or reducing the progression or likelihood of a disease, e.g., Chagas disease, which is associated with the increased levels of proteins truncated by enzymes from *T. cruzi*, (i.e., cruzipain). For example, combinatorial libraries may be screened for compounds which inhibit the ability of a protease from *T. cruzi* (i.e., cruzipain) to cleave one or more of the biomarker proteins described herein. Methods of screening chemical libraries for such compounds are well-known in art. See, e.g., Lopez-Otin et al. (2002). Alternatively, inhibitory compounds may be intelligently designed based on the structure of *T. cruzi* enzymes, including cruzipain.

At the clinical level, screening a test compound includes obtaining samples from test subjects before and after the subjects have been exposed to a test compound. The levels in the samples of one or more of the biomarkers described in Tables 1-4 and in the Figures may be measured and analyzed to determine whether the levels of the biomarkers change after exposure to a test compound. The samples may be analyzed by mass spectrometry, as described herein, or the samples may be analyzed by any appropriate means known to one of skill in the art. For example, the levels of one or more of the biomarkers described herein may be measured directly by Western blot using radio- or fluorescently-labeled antibodies which specifically bind to the biomarkers. Alternatively, changes in the levels of mRNA encoding the one or more biomarkers may be measured and correlated with the administration of a given test compound to a subject. In a further embodiment, the changes in the level of expression of one or more of the biomarkers may be measured using in vitro methods and materials. For example, human tissue cultured cells which express, or are capable of expressing, one or more of the biomarkers described herein may be contacted with test compounds. Subjects who have been treated with test compounds will be routinely examined for any physiological effects which may result from the treatment. In particular, the test compounds will be evaluated for their ability to decrease disease likelihood in a subject. Alternatively, if the test compounds are administered to subjects who have previously been diagnosed with Chagas disease, test compounds will be screened for their ability to slow or stop the progression of the disease.

The invention will be described in greater detail by way of specific examples. The following examples are offered for illustrative purposes, and are not intended to limit the invention in any manner. Those of skill in the art will readily recognize a variety of non-critical parameters that can be changed or modified to yield essentially the same results.

VIII. Examples

A. Example 1

Discovery of Biomarkers for Chagas Disease

For the study which led to the discovery of Chagas disease biomarkers listed in Table 1, study set of consisting of 73 samples was used. Of these 73 samples, 39 of the samples were obtained from patients chronically infected with Chagas disease and 34 were taken from healthy individuals living in the same endemic region. The samples were fractionated and evaluated according to the following protocol.

1. Anion Exchange Fractionation

Prior to the anion exchange pre-fractionation, serum (20 ul) is denatured using a 9 M urea/2% Chaps/50 mM Tris pH 9.0 buffer (U9 buffer). 30 µl of U9 is added to the 20 µl of serum and then this diluted serum is subjected to anion exchange fractionation.

Buffer List for anion exchange fractionation:
U1 (1M urea, 0.22% CHAPS, 50 mM Tris-HCl pH9)
50 mM Tris-HCl with 0.1% OGP pH9 (Wash buffer 1)
50 mM Hepes with 0.1% OGP pH7 (Wash buffer 2)
100 mM NaAcetate with 0.1% OGP pH5 (Wash buffer 3)
100 mM NaAcetate with 0.1% OGP pH4 (Wash buffer 4)
100 mM NaAcetate with 0.1% OGP pH3 (Wash buffer 5)
33.3% isopropanol/16.7% acetonitrile/0.1% trifluoracetic acid (Wash buffer 6)

Note: do not aliquot wash buffer 6 into the buffer tray until wash buffer 5 is being applied to the resin. This ensures that evaporation of the volatile organic solvents will not be an issue.

Material List:
Filter plate
6 v-well 96 well dishes, labeled F1-F6.

a. Wash Resin

Prepare resin by washing Hyper Q DF resin (BioSepra, Cergy, France) 3 times with 5 bed volumes 50 mM Tris-HCl pH9. Then store in 50 mM Tris-HCl pH9 in a 50% suspension.

b. Equilibrate Resin

Add 125 μL Hyper Q DF to each well in filter plate
Filter buffer
Add 150 μL U1 to each well
Filter buffer
Add 150 μL U1 to each well
Filter buffer
Add 150 μL U1 to each well
Filter buffer c. Bind Serum with Resin Pipet 150 4 of sample from each tube to appropriate well in filter plate Vortex 30' at 4° d. Collect Fractions

Place v-well 96 well plate F1 under filter plate
Collect flow-through in plate F1
Add 100 4 of wash buffer 1 to each well of filter plate
Vortex 10' at Room Temperature (RT)
Collect pH 9 eluant in plate F1
Fraction 1 contains the flow through and the pH 9 eluant.
Add 100 μL of wash buffer 2 to each well of filter plate
Vortex 10' at Room Temperature (RT)
Place v-well 96 well plate F2 under filter plate
Collect fraction 2 in plate F2
Add 100 μL of wash buffer 2 to each well of filter plate
Vortex 10' at Room Temperature (RT)
Collect remainder of fraction 2 in plate F2
Fraction 2 contains the pH 7 eluant.
Add 100 4 of wash buffer 3 to each well of filter plate
Vortex 10' at Room Temperature (RT)
Place v-well 96 well plate F3 under filter plate
Collect fraction 3 in plate F3
Add 100 μL of wash buffer 3 to each well of filter plate
Vortex 10' at Room Temperature (RT)
Collect remainder of fraction 3 in plate F3
Fraction 3 contains the pH 5 eluant.
Add 100 μL of wash buffer 4 to each well of filter plate
Vortex 10' at Room Temperature (RT)
Place v-well 96 well plate F4 under filter plate
Collect fraction 4 in plate F4
Add 100 μL of wash buffer 4 to each well of filter plate
Vortex 10' at Room Temperature (RT)
Collect remainder of fraction 4 in plate F4
Fraction 4 contains the pH 4 eluant.
Add 100 μL of wash buffer 5 to each well of filter plate
Vortex 10' at Room Temperature (RT)
Place v-well 96 well plate F5 under filter plate
Collect fraction 5 in plate F5
Add 100 μL of wash buffer 5 to each well of filter plate
Vortex 10' at Room Temperature (RT)
Collect remainder of fraction 5 in plate F5
Fraction 5 contains the pH 3 eluant.
Add 100 μL of wash buffer 6 to each well of filter plate
Vortex 10' at Room Temperature (RT)
Place v-well 96 well plate F6 under filter plate
Collect fraction 6 in plate F6
Add 100 μL of wash buffer 6 to each well of filter plate
Vortex 10' at Room Temperature (RT)
Collect remainder of fraction 6 in plate F6
Fraction 6 contains the organic solvent eluant.
Freeze until proceeding with chip binding protocol 2. Chip Binding Protocol.

Processing Samples using an IMAC-3 ProteinChip
Material:
Bioprocessors
IMAC Chips
Pap Pen
Votex (VWR VX-2500 Multitube Vortexer)
IMAC3 Chip Buffer:
A) Binding Buffer: 100 mM Sodium Phosphate+0.5M NaCl pH 7.0+0.1% Triton X
B) Copper: 100 mM $CuSO_4$+0.1% Triton X 20
C) 100 mM NaAcetate pH 4.0+0.1% Triton X 20
1. Place Chip in bioprocessor
2. Load IMAC chips with copper: Apply 500/well of 100 mM $CuSO_4$
3. Vortex 5 min (speed 100 rpm) at room temperature
4. Remove $CuSO_4$
5. Wash with water 1200/well
6. Vortex 5 min (speed 100 rpm)
7. Neutralize chips: Add 50 μl/well of 100 mM NaAcetate pH 4.0
8. Remove solution
9. Wash with water 1200/well
10. Vortex 5 min (speed 100 rpm)
11. Repeat steps 9 & 10 a further two times
12. Equilibrate Chips: Add 1200 Binding Buffer (PBS/0.5 M NaCl, pH 7.5)
13. Vortex 5 min (100 rpm)
14. Bind fractions to chips: Discard waste and add 80 μl Binding Buffer and 20 μl of fractions (containing samples)
15. Vortex 45-60 min (100 rpm)
16. Discard and wash (PBS/0.5M NaCl, 150 μl/well)
17. Vortex 5 min (100 rpm)
18. Repeat steps 16 & 17 a further two times
19. Rinse chip with $dH_2O$ (150W/well)
20. Add Matrix: Remove bioproceesor top and gasket
21. Rinse the Chips quickly with $dH_2O$
22. Dry chips
23. Circle spots with PAP pen
24. Add 0.5 μl SPA to Chips two times (air dry the spots between addition)
Ciphergen normally supplies EAM as 5 mg of dried powder in a tube.
Add 100 μl of 100% Acetonitrile (final concentration 50% ACN)+50 μl 2%
Trifluoroacetic acid (final conc. 0.5% TFA)+50 μl $dH_2O$.
Vortex 1 min (high speed) and leave it in the bunch for 5 min
Spin 2 min at high speed to pellet any particulates
Dry
Read within 1 hour
Weak Cation Exchanger (WCX2) ProteinChip® Arrays
Place chip in bioprocessor and add 150 μl of binding buffer to each well. Incubate for 5 min at RT on vortex (shaker setting). Remove buffer
Repeat Step 1
Remove buffer from well and immediately add 90 μl binding buffer+10 μl column fraction. Incubate on shaker for 30 min.
Aspirate sample from well and wash each well with 150 μl/well of binding buffer, 5 min at RT, with shaking. Remove sample
Repeat step 4 twice, for a total of 3 washes
Remove chip from bioprocessor and rinse chip briefly with H2O in a tube.
Air-dry the chip array, circle spots with PAP pen. Air dry. Add 2 times 0.5 μl EAM/spot.

Denaturing agents like urea are compatible with this chip surface and will alter the protein profile. GITC is a salt and will inhibit binding as other salts do.
Recommended binding buffers: 50 mM Tris, HEPES or Acetate (pH 4.0-9.5)
Recommended sample dilution: 50-2000 µg/ml total protein
Stringency modifiers: the addition of salts or changes in pH will alter the stringency of the binding step (see chip user notes)
3. Data Acquisition Settings:
Energy absorbing molecule: 50% SPA
Set high mass to 100000 Daltons, optimized from 2000 Daltons to 100000 Daltons.
Set starting laser intensity to 200.
Set starting detector sensitivity to 8.
Focus mass at 8000 Daltons.
Set Mass Deflector to 1000 Daltons.
Set data acquisition method to Seldi Quantitation
Set Seldi acquisition parameters 20. delta to 4. transients per to 10 ending position to 80.
Set warming positions with 2 shots at intensity 225
Process sample.

Methods used to analyze the data (shown in Table 1) are described above. Representative spectra appear in FIG. 1.

4. Determination of Biomarker Identity.
Identification of the 110 kDa protein

Proteins were separated on an acrylamide gel and a band containing the biomarker was cut out of the gel. The protein in the band was destained. The gel was dried using acetonitrile and then subject to digestion in a solution of trypsin. The digest fragments were analyzed on a Ciphergen PBSII mass spectrometer. The determined masses were used to interrogate the NCBInr protein database (using ProFound software), which identified the protein having the same tryptic digest pattern.

Figure 2:
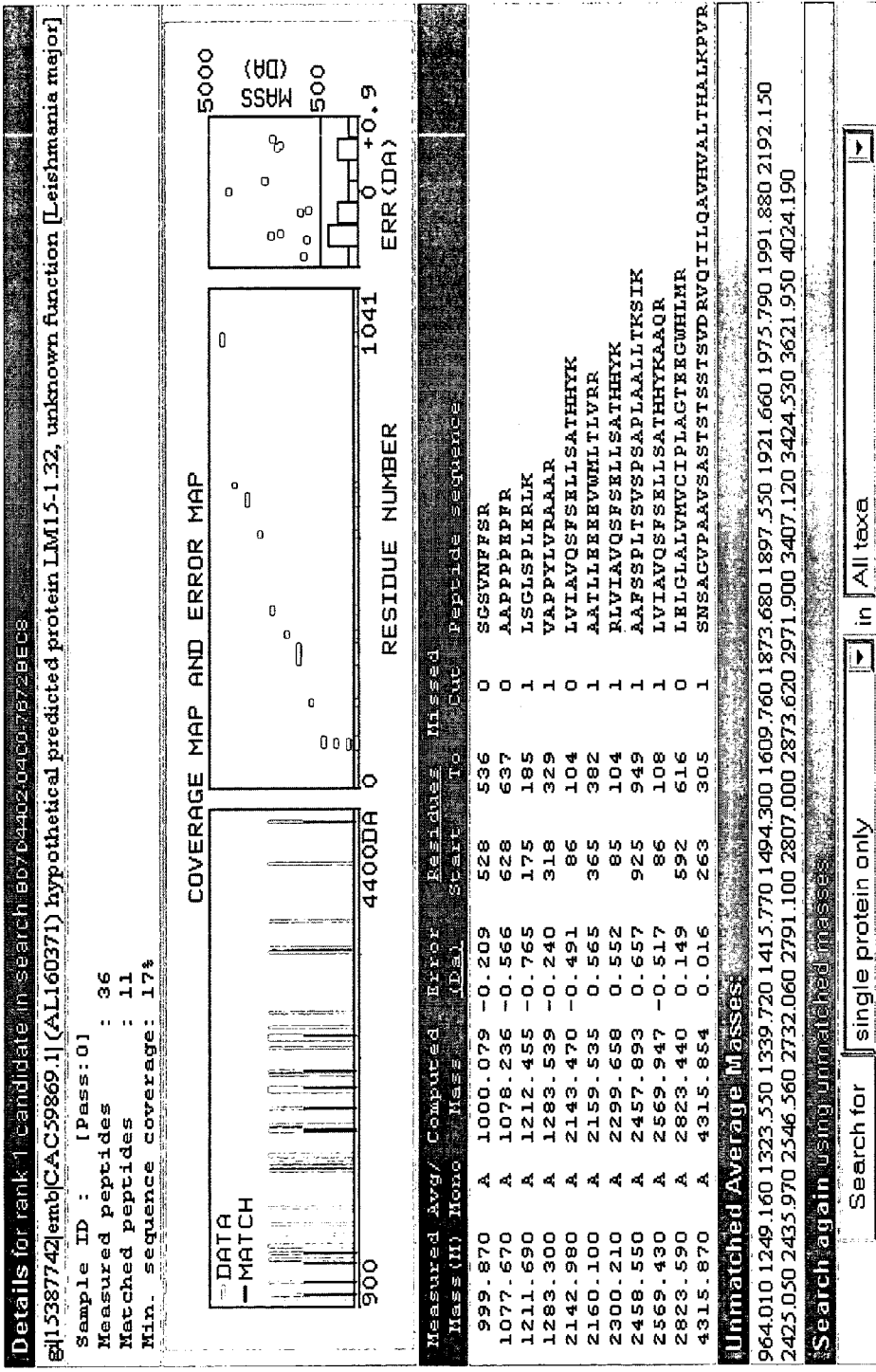
FIG. 2 shows the analysis of the trypsin digests of the 110 kDa Chagas disease biomarker (SEQ ID NOS:1-11).

Using the aforementioned techniques, an approximately 110 kDa protein was identified as a highly significant biomarker for Chagas disease. This protein, designated M110, is a novel protein with homology to a predicted protein (LM15-1.32) encoded by *Leishmanii major*. A summary of the search results and sequenced fragments of M110 are shown in FIG. 2.

Identification of the 7.861 kDa Protein

Another biomarker with a mass of 7.8 kD, M7.861, was identified as human MIP-1α The protein identity was confirmed using an ELISA assay and an antibody specific to MIP-1α Measurements of MIP-1α levels in Chagas disease infected subjects versus non-infected subjects showed that the mean level of MIP-1α in the serum of infected subjects (20.73 pg/ml) was significantly higher than the mean level in versus non-infected subjects (12.22 pg/ml).

Identification of the Purified 13.6 kDa Protein

The 13.6 kDa protein was detected in fraction 1 on IMAC-Cu and WCX arrays using SPA as the EAM. A tryptic digest of the 13.6 kDa protein was analyzed by mass-spectrometry in a single MS mode. Major unique peaks were further analyzed with tandem MS, and resulting CID data were submitted to Mascot Database for identification. The following ions were identified as tryptic fragments of Apolipoprotein A-I:

| m/z | Position | Sequence | SEQ ID NO: |
|---|---|---|---|
| 1012.57 | 207-215 | AKPALEDLR | 12 |
| 1157.62 | 178-188 | LEALKENGGAR | 13 |
| 1230.71 | 216-226 | QGLLPVLESFK | 14 |
| 1301.64 | 161-171 | THLAPYSDELR | 15 |
| 1318.64 | 141-151 | LSPLGEEMRDR | 16 |
| 1386.71 | 227-238 | VSFLSALEEYTK | 17 |

The amino acid sequence of ApoA-I is shown below (SEQ ID NO:18). Peptides identified by CID fragmentation are highlighted in italics.

```
          1          11          21          31          41          51
          |           |           |           |           |           |
  1 DEPPQSPWDR VKDLATVYVD VLKDSGRDYV SQFEGSALGK QLNLKLLDNW DSVTSTFSKL

61 REQLGPVTQE FWDNLEKETE GLRQEMSKDL EEVKAKVQPY LDDFQKKWQE EMELYRQKVE

121 PLRAELQEGA RQKLHELQEK LSPLGEEMRD RARAHVDALR THLAPYSDEL RQRLAARLEA

181 LKENCGARLA EYHAKATEHL STLSEKAKPA LEDLRQGLLP VLESFKVSFL SALEEYTKKL

241 NTQ
```

All six tryptic fragments were from the C-terminal half of the protein. The systematic chopping of amino acid from the N-terminus ended up at Arg123 (trypsin cut). The MW of the remaining C-terminal half was calculated to be 13,570.40 Da (the putative N-terminal Ala124 is underlined). The 13.6 kDa fragment thus corresponds to amino acids 124-243 of the full-length protein.

Identification of the 8.1 kDa Protein

The 8.1 kDa protein was detected in fraction 1 on IMAC-Cu and WCX arrays using SPA as the EAM. A tryptic digest of the 8.1 kDa protein was analyzed by mass-spectrometry in a single MS mode. Major unique peaks were further analyzed with tandem MS, and resulting CID data were submitted to Mascot Database for identification. The following ions were identified as tryptic fragments of Complement C3 anaphylatoxin:

| m/z | Position | Sequence | SEQ ID NO: |
|---|---|---|---|
| 1095.58 | 42-51 | FISLGEACKK | 19 |
| 1339.59 | 18-28 | ELRKCCEDGMR | 20 |
| 1588.74 | 52-64 | VFLDCCNYITELR | 21 |
| 1716.84 | 51-64 | KVFLDCCNYITELR | 22 |

The amino acid sequence of C3a is shown below (SEQ ID NO:23). Peptides identified by CID fragmentation are highlighted in italics.

```
     1          11         21         31         41         51
     |          |          |          |          |          |
  1 SVQLTEKRMD KVGKYPKELR KCCEDGMREN PMRFSCQRRT RFISLGEACK KVFLDCCNYI
 61 TELRRQHARA SHLGLAR
```

Confirmation of the Identified 8.1 kDa Protein by Immunoassay

Figure 5:
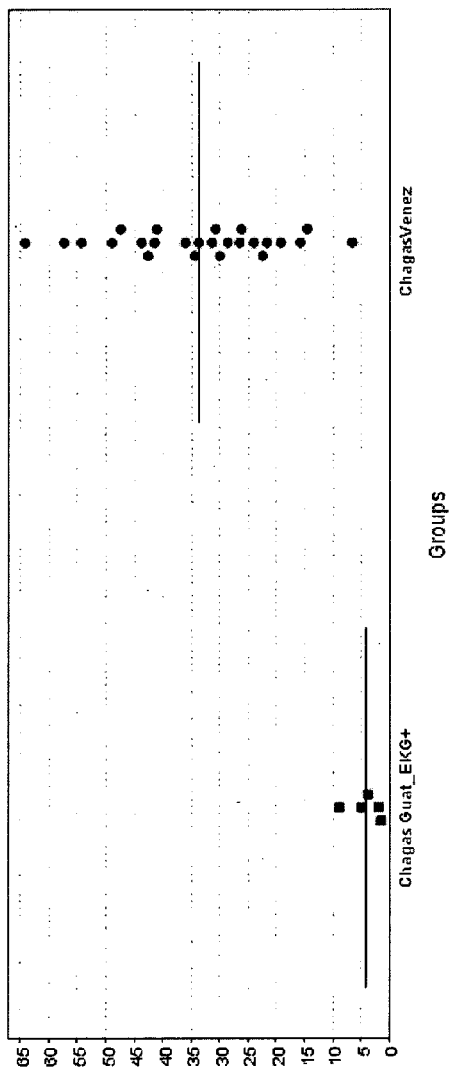
FIG. 5 shows a graphical representation of the differential signal intensity of a 8.127 kDa peptide from Apo-1 in asymptomatic chronically infected Venezuelan patients infected with Chagas versus acutely infected pediatric Guatemalan patients with EKG signs indicative of Chagas disease. In this case the difference in intensity of the biomarker is significant (p=0.001), but the signal is present at some level in both infected Venezuelan patients or in acutely infected Guatemalan patients with or without EKG signs indicative of Chagas disease. This biomarker is useful for qualifying chronic Chagas disease and for distinguishing between chronic and acutely infected individuals.
Figure 6:
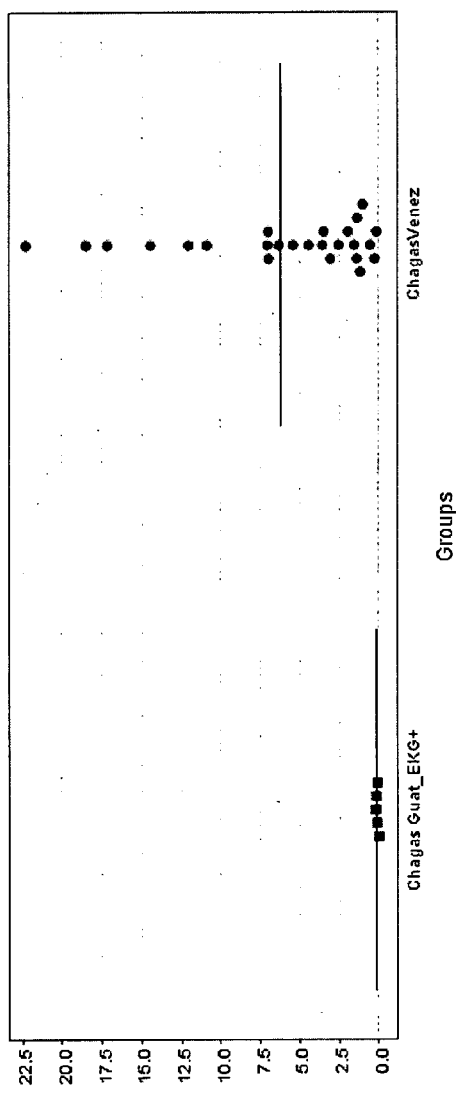
FIG. 6 shows a graphical representation of the differential signal intensity of a 8.937 kDa peptide in asymptomatic chronically infected Venezuelan patients infected with Chagas versus acutely infected Guatemalan patients with high EKG readings. In this case, the difference in intensity of the biomarker is significant (p=0.002), but the signal is present at some level in both infected Venezuelan patients or in acutely infected Guatemalan patients with or without EKG signs indicative of Chagas disease. This biomarker is useful for qualifying chronic Chagas disease and for distinguishing between chronic and acutely infected individuals.

Monoclonal anti-C3a antibody and control mouse IgG were coupled to ProteinA HyperD beads. The serum sample 506N containing according to the profiling study approximately equal amounts of the 8.1 kDa and 8.9 kDa proteins was incubated with beads. Unbound proteins were removed by wash with PBS, and bound proteins were eluted with 0.1 M acetic acid. Profiling of the eluted fractions showed that the 8.1 kDa and 8936 Da proteins specifically bound to the anti-C3a antibody, but not to control mouse IgG, thus confirming that both proteins are derivatives of human C3 anaphylatoxin (FIG. 5). C3 convertase activates Complement C3 by cleaving the alpha chain, releasing C3a anaphylatoxin. In the blood, C3a activity is under control of the carboxypeptidase N. The enzyme rapidly cuts off the C-terminal arginine, thereby generating C4ades-Arg (MW 8938.46). The 8.1 kda protein appears to be the product of further degradation/cleavage of C3ades-Arg. The systematic removal of N-terminal amino acids would result in the 8152.56 Da peptide. In contrast, the C-terminal amino acid removal would result in the 8132.52 Da peptide. Therefore, the 8.13 kDa biomarker corresponds to the C-terminal truncation of C3a, specifically amino acids 1-68 of the full-length protein. Most likely, this polypeptide is generated by trypsin cleavage at Arg69 followed by the removal of Arg by carboxypeptidase N. The putative C-terminal Ala68 is underlined. Table 1 includes representative fraction and chip conditions where the truncated C3 anaphylatoxin biomarker may be observed.

Identification of the 28.7 kDa Protein

As shown in Table 1, the 28.7 kDa protein was detected in fraction 1 on WCX array using SPA as the EAM. A tryptic digest of the 28.7 kDa protein was analyzed by mass-spectrometry in a single MS mode. Major unique peaks were further analyzed with tandem MS, and resulting CID data were submitted to Mascot Database for identification. The following ions were identified as tryptic fragments of Fibronectin:

| m/z | Position | Sequence | SEQ ID NO: |
|---|---|---|---|
| 1348.64 | 222-234 | GNLLQCICTGNGR | 24 |
| 1401.66 | 27-36 | HYQLNQQWER | 25 |
| 1527.63 | 86-99 | DSMIWDCTCIGAGR | 26 |
| 1677.77 | 37-52 | TYLGNALVCTCYGGSR | 27 |
| 1707.78 | 242-258 | HTSVQTTSSGSGPFTDV | 28 |
| 1866.85 | 102-118 | ISCTIANRCHEGGQSYK | 29 |
| 2789.18 | 5 3-76 | GFNCESKPEAEETCFDKYTGNTYR | 30 |

The N-terminal amino acid sequence of Fibronectin is shown below (SEQ ID NO:31). Peptides identified by CID fragmentation are highlighted in italics.

```
       1          11         21         31         41         51
       |          |          |          |          |          |
   1 QAQQMVQPQS PVAVSQSKPG CYDNGKHYQI NQQWERTYLG NALVCTCYGG SRGFNCESKP

61 EAEETCFDKY TGNTYRVGDT YERPKDSMIW DCTCIGAGRG RISCTIANRC HEGGQSYKIG

121 DTWRRPHETG GYMLECVCLG NGKGEWTCKP IAEKCFDHAA GTSYVVGETW EKPYQGWNMV

181 DCTCLGEGSG RITCTSRNRC NDQDTRTSYR IGDTWSKKDN RGNLLQCICT GNGRGEWKCE

241 RHTSVQTTSS GSGPFTDVRA AVYQPQPHPQ PPPYGHCVTD SGVVYSVGMQ WLKTQGNKQM
```

All seven identified tryptic fragments correspond to the N-terminus of Fibronectin. Importantly, one fragment with the M/Z of 1707 had a non-tryptic cut at the C-terminus, strongly suggesting that this is the C-terminal end of the 28.7 kDa protein. Indeed, the calculated MW of the sequence from the N-terminus to Val258 is 28,765.95 Da. This fragment contains 19 Cys, which are known to be involved in nine bridges (−18 Da). Also, the N-terminal Gln is modified to pyrrolidone carboxylic acid (−17 Da). The resulting MW is thus 28,731 Da. Most likely, this polypeptide is generated by trypsin cleavage at Arg259 followed by the removal of Arg by carboxypeptidase N. The C-terminal Val258 is underlined in the sequence above. Thus, this 28.7 kDa kilodalton protein corresponds to amino acids 1-258 of full-length fibronectin (see, e.g., marker F1WH_6 in Table 1). The 28.7 kDa fragment may represent the product of Fibronectin digestion by cruzipain, a trypanosomal protein which binds to the fibronectin network present in heart tissue.

Identification of the 24.7 kDa Protein

The 24.7 kDa Da protein was detected in fraction 4 on IMAC-Cu and WCX arrays using SPA as the EAM. A tryptic digest of the 24.7 kDa protein was analyzed by mass-spectrometry in a single MS mode. Major unique peaks were further analyzed with tandem MS, and resulting CID data were submitted to Mascot Database for identification. The following ions were identified as tryptic fragments of Apolipoprotein A-I:

| m/z | Position | Sequence | SEQ ID NO: |
|---|---|---|---|
| 1031.51 | 141-149 | LSPLGEEMR | 32 |
| 1226.54 | 1-10 | DEPPQSPWDR | 33 |
| 1301.64 | 161-171 | THLAPYSDELR | 34 |
| 1400.67 | 28-40 | DYVSQFEGSALGK | 35 |
| 1612.78 | 46-59 | LLDNW DSVTSTFSK | 36 |
| 1723.94 | 117-131 | QKVEPLRAELQEGAR | 37 |
| 1815.85 | 24-40 | DSGRDYVSQFEGSALGK | 38 |

The amino acid sequence of ApoA-I is shown below (SEQ ID NO:18). Peptides identified by OD fragmentation are highlighted in italics.

```
     1          11          21          31          41          51
     |          |           |           |           |           |
  1 DEPPQSPWDR VKDLATVYVD VLKDSGRDYV SQFEGSALGK QLNLKLLDNW DSVTSTFSKL

61 REQLGPVTQE FWDNLEKETE GLRQEMSKDL EEVKAKVQPY LDDFQKKWQE EMELYRQKVE

121 PLRAELQEGA RQKLHELQEK LSPLGEEMRD RARAHVDALR THLAPYSDEL RQRLAARLEA

181 LKENGGARLA EYHAKATEHL STLSEKAKPA LEDLRQGLLP VLESFKVSFL SALEEYTKKL

241 NTQ
```

The MW of the full-length ApoA-I is 28,078.62. Several fragments corresponded to the N-terminal part of ApoA-I. In contrast, the C-terminal fragments of the 13.6 kDa protein were not detected in the digest of the 24.7 kDa protein. Thus, the 24.7 kDa protein is the C-terminal truncation of ApoA-I, corresponding to amino acids 1-214 of the full-length protein (see, e.g., the F41H_4 biomarker in Table 1). The systematic removal of amino acids from the C-terminus resulted in the sequence with the theoretical MW of 24,756 Da. This polypeptide, then, is likely generated by trypsin cleavage at Arg215 followed by the removal of Arg by carboxypeptidase N. The C-terminal Leu214 is underlined in the above Apo A-I sequence.

Identification of the 16.3 kDa Protein.

The 16.3 kDa marker replicated the appearance of the 8133 Da marker identified as truncated C3a. Furthermore, the mass of the 16.3 kDa marker strongly suggested that it was a dimer of the 8133 Da marker. Two samples with very high (Chagas positive) and very low (Chagas negative) content of the 8133 Da protein were analyzed using a beads-based immunoassay with the monoclonal Ab against C3a. As expected, the pull-down of the 8133 Da protein was very specific. Similarly, the 16.3 kDa was specifically pulled down from the positive sample by C3a Ab, but not by a mouse control IgG antibody, indicating that the 16.3 kDa protein is a dimer of the truncated C3a fragment corresponding to amino acids 1-68 of the full-length protein (see, e.g., F1IH_2 and the corresponding monomer biomarker, F1IL_7, in Table 1). This dimer was found to be DTT-resistant, therefore it is not a Cys-bridged dimer.

Identification of the 9.3 and 10.1 kDa Proteins

The 9.3 kDa and 10.1 kDa markers (e.g., F1WL_3 and F1WH_1, respectively) were co-purified through anion exchange and reverse phase chromatography. These two markers migrated together through both reducing and non-reducing SDS-PAGE. Trypsin digestion of the gel-extracted bands showed the same Apolipoprotein A-I fragments identified for the 13.6 kDa marker, except for one peptide present in the 13.6 kDa digest, but absent in the 9.3/10.1 kDa digest. The latter tryptic fragment is the most N-terminal in the 13.6 kDa sequence, indicating that both 9.3 kDa and 10.1 kDa polypeptides represent further degradation of ApoA1 in the N— to C-terminal direction. The sequential removal of amino acid from the N-terminus of ApoA1 resulted in a theoretical molecular weights of 9306.59 Da (observed MW 9307 Da) and 10069.46 Da (observed MW 10070 Da) for the candidate biomarkers. Thus, the 9.3 kDa biomarker corresponds to a fragment consisting of amino acids 161-243 of full-length ApoA1, while the 10.1 kDa biomarker corresponds to a fragment consisting of amino acids 154-243 of full-length ApoA1.

B. Discovery of Additional Biomarkers

Using protocols similar to those described in Example A., above, additional sample sets were analyzed. The studies included samples taken from patients with parasitic diseases, such as the following.

TABLE 1B

| Parasitic Disease | Cause |
|---|---|
| Chagas | *T. cruzi* protozoa |
| Malaria | *plasmodium* protozoa |
| Toxoplasma | protozoan |
| *Schistosoma mansoni* | trematode/liver fluke |
| Babesia | protozoan |
| *Fasciola* | trematode/liver fluke |
| *Filaria* | intestinal nematode |
| Cysticercosis | *Taenia solium* flatworm |
| Hydatid disease | Echinococcosis/cestode |
| Toxocara | protozoan |
| Strongyloides | nematode, intestinal |
| Trichinellosis | nematode |
| Leishmania | protozoan |
| African Tryps | protozoan |

For example, Table 2 in the "Chagas versus Healthy" column shows the results of a biomarker discovery study analyzing samples taken from approximately 40 infected Chagas patients versus roughly the same number of healthy uninfected geographically matched controls. The infected set included 11 Guatemalen patients with acute Chagas disease, 12 patients from Cuba, 10 chronically infected patients from Venezuela and 3 Chagas infected Canadian patients. To obtain the set of biomarkers shown in the "Chagas versus Non-Chagas" column, a sample was used which included 11 Guatemalen patients with acute Chagas disease, 12 patients from Cuba, and 10 chronically infected patients from Venezuela and 3 Chagas infected Canadian patients. This sample was analyzed against the set which included the uninfected patient set as well as 42 patients infected with other parasitic diseases (*Babesia, Chagas, Leishmania, Malaria, Toxoplasma*). The p-values and specificities of some preferred biomarkers are highlighted in bold in Table 2A-2X.

Tables 3 and 4 collect a preferred set of biomarkers from each study with greater degrees of sensitivity and specificity, as indicated in Table 2 (typically, p-value less than 0.006; ROC greater than 0.7 or less 0.3). Note that when using combinations of biomarkers, an important consideration in increasing specificity will be to use biomarkers whose level of expression and/or intensity are independent of each other.

TABLE 2A

F5ISL

| Master ID | Chagas vs Healthy | | Chagas vs Non-Chagas | | M/Z Average (Da) |
|---|---|---|---|---|---|
| | p-value | ROC | p-value | ROC | |
| F5ISL_1 | 0.43993 | 0.59 | 0.28210 | 0.57 | 2437.21 |
| F5ISL_2 | 0.42433 | 0.46 | 0.15326 | 0.41 | 2473.05 |
| F5ISL_3 | 0.13587 | 0.61 | 0.27409 | 0.56 | 2507.49 |
| F5ISL_4 | 0.95752 | 0.49 | 0.57520 | 0.46 | 2541.94 |
| F5ISL_5 | 0.24129 | 0.61 | 0.15326 | 0.61 | 2576.33 |
| F5ISL_6 | 0.04579 | 0.71 | 0.00005 | 0.76 | 3170.99 |
| F5ISL_7 | 0.15811 | 0.34 | 0.65131 | 0.47 | 4253.38 |
| F5ISL_8 | 0.76957 | 0.56 | 0.00787 | 0.67 | 4274.46 |
| F5ISL_9 | 0.09871 | 0.66 | 0.17516 | 0.42 | 4632.14 |
| F5ISL_10 | 0.40905 | 0.56 | 0.41078 | 0.45 | 7928.86 |
| F5ISL_11 | 0.04579 | 0.30 | 0.94236 | 0.51 | 8145.12 |
| F5ISL_12 | 0.19192 | 0.34 | 0.00568 | 0.35 | 28104.33 |
| F5ISL_13 | 0.00715 | 0.76 | 0.00047 | 0.71 | 75548.95 |

TABLE 2B

F5ISH

| Master ID | Chagas vs Healthy | | Chagas vs Non-Chagas | | M/Z Average (Da) |
|---|---|---|---|---|---|
| | p-value | ROC | p-value | ROC | |
| F5ISH_1 | 0.23336 | 0.39 | 0.00615 | 0.34 | 27776.33 |
| F5ISH_2 | 0.04394 | 0.31 | 0.00004 | 0.26 | 28036.18 |
| F5ISH_3 | 0.01998 | 0.25 | 0.00006 | 0.24 | 28269.46 |
| F5ISH_4 | 0.26845 | 0.61 | 0.00173 | 0.67 | 37686.13 |
| F5ISH_5 | 0.05367 | 0.28 | 0.00567 | 0.33 | 43248.19 |
| F5ISH_6 | 0.13261 | 0.36 | 0.00100 | 0.31 | 44584.56 |
| F5ISH_7 | 0.03832 | 0.28 | 0.00030 | 0.29 | 59454.95 |
| F5ISH_8 | 0.11861 | 0.33 | 0.00292 | 0.32 | 60518.21 |
| F5ISH_9 | 0.07853 | 0.69 | 0.00060 | 0.71 | 75647.95 |
| F5ISH_10 | 0.00497 | 0.78 | 0.00012 | 0.75 | 103795.90 |
| F5ISH_11 | 0.01468 | 0.22 | 0.01229 | 0.34 | 154980.69 |
| F5ISH_12 | 0.37906 | 0.42 | 0.02678 | 0.40 | 160953.72 |

TABLE 2C

F6ISH

| Master ID | Chagas vs Healthy | | Chagas vs Non-Chagas | | M/Z Average (Da) |
|---|---|---|---|---|---|
| | p-value | ROC | p-value | ROC | |
| F6ISH_1 | 0.83326 | 0.50 | 0.64223 | 0.53 | 10196.53 |
| F6ISH_2 | 0.13205 | 0.70 | 0.01328 | 0.65 | 18089.54 |
| F6ISH_3 | 0.35596 | 0.64 | 0.00238 | 0.70 | 24752.79 |
| F6ISH_4 | 0.04294 | 0.27 | 0.07993 | 0.38 | 28084.41 |
| F6ISH_5 | 0.01582 | 0.24 | 0.09303 | 0.41 | 28275.51 |

TABLE 2C-continued

F6ISH

| Master ID | Chagas vs Healthy | | Chagas vs Non-Chagas | | M/Z Average (Da) |
|---|---|---|---|---|---|
| | p-value | ROC | p-value | ROC | |
| F6ISH_6 | 0.02057 | 0.24 | 0.18608 | 0.39 | 28400.83 |
| F6ISH_7 | 0.68558 | 0.44 | 0.04704 | 0.37 | 55418.73 |
| F6ISH_8 | 0.27791 | 0.39 | 0.00044 | 0.27 | 55962.00 |
| F6ISH_9 | 0.12393 | 0.33 | 0.00037 | 0.27 | 56167.48 |
| F6ISH_10 | 0.08313 | 0.33 | 0.00119 | 0.27 | 56414.40 |
| F6ISH_11 | 0.10888 | 0.33 | 0.00015 | 0.26 | 57022.49 |
| F6ISH_12 | 0.12393 | 0.30 | 0.00014 | 0.28 | 57908.91 |
| F6ISH_13 | 0.21241 | 0.39 | 0.00405 | 0.32 | 59108.57 |
| F6ISH_14 | 0.25022 | 0.36 | 0.01023 | 0.33 | 60116.69 |
| F6ISH_15 | 0.00030 | 0.90 | 0.00003 | 0.77 | 75426.74 |
| F6ISH_16 | 0.02651 | 0.76 | 0.02372 | 0.62 | 84266.77 |
| F6ISH_17 | 0.12393 | 0.64 | 0.00158 | 0.71 | 133669.32 |

TABLE 2D

F6ISL

| Master ID | Chagas vs Healthy | | Chagas vs Non-Chagas | | M/Z Average (Da) |
|---|---|---|---|---|---|
| | p-value | ROC | p-value | ROC | |
| F6ISL_1 | 0.87305 | 0.46 | 0.97937 | 0.49 | 3321.40 |
| F6ISL_2 | 0.59429 | 0.56 | 0.00496 | 0.67 | 5102.80 |
| F6ISL_3 | 0.37949 | 0.43 | 0.00203 | 0.67 | 6194.40 |
| F6ISL_4 | 0.65074 | 0.54 | 0.25529 | 0.43 | 6632.75 |
| F6ISL_5 | 0.93632 | 0.49 | 0.21460 | 0.43 | 6846.99 |
| F6ISL_6 | 0.15811 | 0.39 | 0.21780 | 0.42 | 8937.06 |
| F6ISL_7 | 0.54020 | 0.56 | 0.03780 | 0.62 | 24160.09 |
| F6ISL_8 | 0.45586 | 0.41 | 0.02188 | 0.36 | 43910.53 |
| F6ISL_9 | 0.20114 | 0.39 | 0.00078 | 0.29 | 44015.50 |
| F6ISL_10 | 0.11007 | 0.34 | 0.00215 | 0.30 | 56654.33 |
| F6ISL_11 | 0.03100 | 0.29 | 0.00047 | 0.28 | 56807.45 |
| F6ISL_12 | 0.11613 | 0.36 | 0.00215 | 0.31 | 56852.91 |
| F6ISL_13 | 0.29898 | 0.38 | 0.00320 | 0.32 | 59020.40 |
| F6ISL_14 | 0.47212 | 0.56 | 0.03053 | 0.63 | 74105.59 |
| F6ISL_15 | 0.01537 | 0.74 | 0.00339 | 0.67 | 75476.22 |

TABLE 2E

F4ISH

| Master ID | Chagas vs Healthy | | Chagas vs Non-Chagas | | M/Z Average (Da) |
|---|---|---|---|---|---|
| | p-value | ROC | p-value | ROC | |
| F4ISH_1 | 0.24430 | 0.34 | 0.01559 | 0.35 | 11705.05 |
| F4ISH_2 | 0.06000 | 0.29 | 0.02338 | 0.36 | 13598.02 |
| F4ISH_3 | 0.00940 | 0.22 | 0.10260 | 0.40 | 13996.67 |
| F4ISH_4 | 0.00501 | 0.19 | 0.00692 | 0.34 | 14076.61 |
| F4ISH_5 | 0.00092 | 0.17 | 0.00045 | 0.26 | 14162.34 |
| F4ISH_6 | 0.00074 | 0.17 | 0.00006 | 0.25 | 14203.94 |
| F4ISH_7 | 0.00172 | 0.17 | 0.00018 | 0.26 | 14252.34 |
| F4ISH_8 | 0.01560 | 0.24 | 0.00735 | 0.32 | 28304.14 |
| F4ISH_9 | 0.00501 | 0.21 | 0.00421 | 0.33 | 28866.98 |
| F4ISH_10 | 0.07817 | 0.33 | 0.02595 | 0.36 | 51287.67 |
| F4ISH_11 | 0.01436 | 0.73 | 0.00029 | 0.74 | 75141.77 |
| F4ISH_12 | 0.06859 | 0.70 | 0.00064 | 0.70 | 100518.18 |
| F4ISH_13 | 0.19924 | 0.62 | 0.00066 | 0.69 | 133704.04 |
| F4ISH_14 | 0.20989 | 0.65 | 0.02529 | 0.63 | 147717.15 |

TABLE 2F

F3WSH

| Master ID | Chagas vs Healthy p-value | ROC | Chagas vs Non-Chagas p-value | ROC | M/Z Average (Da) |
|---|---|---|---|---|---|
| F3WSH_1 | 0.00556 | 0.25 | 0.56589 | 0.54 | 10110.75 |
| F3WSH_2 | 0.34100 | 0.61 | 0.04498 | 0.62 | 11455.20 |
| F3WSH_3 | 0.01268 | 0.79 | 0.00626 | 0.68 | 12502.93 |
| F3WSH_4 | 0.06060 | 0.70 | 0.20526 | 0.42 | 13594.05 |
| F3WSH_5 | 0.69500 | 0.54 | 0.69517 | 0.48 | 14059.44 |
| F3WSH_6 | 0.65409 | 0.51 | 0.53547 | 0.46 | 14174.75 |
| F3WSH_7 | 0.38530 | 0.63 | 0.60346 | 0.47 | 17402.10 |
| F3WSH_8 | 0.00510 | 0.79 | 0.00000 | 0.80 | 24893.62 |
| F3WSH_9 | 0.37016 | 0.42 | 0.07118 | 0.39 | 27950.80 |
| F3WSH_10 | 0.59465 | 0.46 | 0.07262 | 0.40 | 28092.19 |
| F3WSH_11 | 0.43295 | 0.39 | 0.03528 | 0.38 | 28269.84 |
| F3WSH_12 | 0.30011 | 0.37 | 0.00486 | 0.32 | 29245.29 |
| F3WSH_13 | 0.15321 | 0.35 | 0.97819 | 0.50 | 37345.84 |
| F3WSH_14 | 0.28723 | 0.38 | 0.00172 | 0.31 | 51352.12 |

TABLE 2G

F3WSL

| Master ID | Chagas vs Healthy p-value | ROC | Chagas vs Non-Chagas p-value | ROC | M/Z Average (Da) |
|---|---|---|---|---|---|
| F3WSL_1 | 0.01298 | 0.76 | 0.001887 | 0.69 | 2694.25 |
| F3WSL_2 | 0.28700 | 0.63 | 0.000190 | 0.72 | 2790.34 |
| F3WSL_3 | 0.68216 | 0.50 | 0.003097 | 0.68 | 2993.03 |
| F3WSL_4 | 0.31243 | 0.58 | 0.000018 | 0.76 | 3013.11 |
| F3WSL_5 | 0.32569 | 0.63 | 0.001274 | 0.69 | 3033.30 |
| F3WSL_6 | 0.35329 | 0.60 | 0.010395 | 0.67 | 3148.90 |
| F3WSL_7 | 0.89142 | 0.47 | 0.251317 | 0.56 | 3388.92 |
| F3WSL_8 | 0.74321 | 0.53 | 0.006515 | 0.69 | 3412.41 |
| F3WSL_9 | 0.86988 | 0.47 | 0.005399 | 0.68 | 3499.33 |
| F3WSL_10 | 0.11332 | 0.65 | 0.000112 | 0.73 | 3655.82 |
| F3WSL_11 | 0.64256 | 0.58 | 0.411129 | 0.55 | 3744.27 |
| F3WSL_12 | 0.00292 | 0.81 | 0.002459 | 0.68 | 3932.19 |
| F3WSL_13 | 0.29953 | 0.63 | 0.000165 | 0.73 | 3982.22 |
| F3WSL_14 | 0.00223 | 0.19 | 0.003097 | 0.33 | 4077.76 |
| F3WSL_15 | 0.68216 | 0.47 | 0.795389 | 0.49 | 4149.05 |
| F3WSL_16 | 0.76394 | 0.47 | 0.005699 | 0.67 | 4220.44 |
| F3WSL_17 | 0.39737 | 0.58 | 0.000003 | 0.79 | 4242.16 |
| F3WSL_18 | 0.46105 | 0.55 | 0.000125 | 0.71 | 4424.62 |
| F3WSL_19 | 0.16382 | 0.65 | 0.000165 | 0.72 | 4450.87 |
| F3WSL_20 | 0.00087 | 0.86 | 0.000006 | 0.78 | 5380.70 |
| F3WSL_21 | 0.62313 | 0.42 | 0.000579 | 0.70 | 5643.49 |
| F3WSL_22 | 0.70230 | 0.53 | 0.000850 | 0.29 | 5901.48 |
| F3WSL_23 | 0.19005 | 0.65 | 0.000002 | 0.80 | 5988.65 |
| F3WSL_24 | 0.19005 | 0.65 | 0.000016 | 0.76 | 6008.67 |
| F3WSL_25 | 0.42852 | 0.63 | 0.000025 | 0.77 | 6146.33 |
| F3WSL_26 | 0.15571 | 0.65 | 0.000010 | 0.79 | 6192.87 |
| F3WSL_27 | 0.38232 | 0.63 | 0.000905 | 0.70 | 6391.74 |
| F3WSL_28 | 0.56643 | 0.45 | 0.863898 | 0.52 | 6450.92 |
| F3WSL_29 | 0.32569 | 0.37 | 0.000006 | 0.21 | 6499.23 |
| F3WSL_30 | 0.01511 | 0.24 | 0.000144 | 0.26 | 6519.18 |
| F3WSL_31 | 0.14791 | 0.65 | 0.000002 | 0.77 | 6877.34 |
| F3WSL_32 | 0.01511 | 0.76 | 0.000120 | 0.74 | 7080.70 |
| F3WSL_33 | 0.07597 | 0.68 | 0.000525 | 0.70 | 7559.15 |
| F3WSL_34 | 0.13321 | 0.32 | 0.277646 | 0.40 | 8126.14 |
| F3WSL_35 | 0.18098 | 0.37 | 0.594848 | 0.43 | 8141.63 |
| F3WSL_36 | 0.05960 | 0.68 | 0.000144 | 0.73 | 8859.26 |
| F3WSL_37 | 0.13321 | 0.37 | 0.034506 | 0.40 | 8934.40 |
| F3WSL_38 | 0.38232 | 0.60 | 0.001625 | 0.70 | 9185.80 |
| F3WSL_39 | 0.01202 | 0.76 | 0.000008 | 0.78 | 24827.43 |
| F3WSL_40 | 0.29953 | 0.40 | 0.006691 | 0.35 | 33349.46 |
| F3WSL_41 | 0.08544 | 0.68 | 0.068149 | 0.60 | 53760.45 |
| F3WSL_42 | 0.07597 | 0.35 | 0.003469 | 0.34 | 66517.71 |
| F3WSL_43 | 0.38232 | 0.55 | 0.005699 | 0.68 | 72985.70 |

TABLE 2H

F1WSL

| Master ID | Chagas vs Healthy p-value | ROC | Chagas vs Non-Chagas p-value | ROC | M/Z Average (Da) |
|---|---|---|---|---|---|
| F1WSL_1 | 0.54604 | 0.43 | 0.62577 | 0.48 | 2518.63 |
| F1WSL_2 | 0.93127 | 0.50 | 0.00598 | 0.68 | 2989.29 |
| F1WSL_3 | 0.07469 | 0.69 | 0.01187 | 0.68 | 3008.29 |
| F1WSL_4 | 0.52709 | 0.59 | 0.03154 | 0.65 | 3172.94 |
| F1WSL_5 | 0.12760 | 0.37 | 0.00559 | 0.32 | 3410.48 |
| F1WSL_6 | 0.54604 | 0.57 | 0.00662 | 0.69 | 3829.34 |
| F1WSL_7 | 0.43763 | 0.57 | 0.02053 | 0.36 | 3850.31 |
| F1WSL_8 | 0.11385 | 0.67 | 0.00088 | 0.72 | 3873.66 |
| F1WSL_9 | 0.05778 | 0.31 | 0.00287 | 0.31 | 3897.07 |
| F1WSL_10 | 0.15060 | 0.33 | 0.05109 | 0.38 | 4071.59 |
| F1WSL_11 | 0.02314 | 0.74 | 0.00297 | 0.69 | 4185.29 |
| F1WSL_12 | 0.00751 | 0.76 | 0.00126 | 0.73 | 4396.10 |
| F1WSL_13 | 0.32836 | 0.38 | 0.28232 | 0.44 | 4483.28 |
| F1WSL_14 | 0.31433 | 0.59 | 0.00662 | 0.69 | 4807.13 |
| F1WSL_15 | 0.00529 | 0.20 | 0.00191 | 0.32 | 5021.55 |
| F1WSL_16 | 0.10742 | 0.67 | 0.00022 | 0.75 | 5378.75 |
| F1WSL_17 | 0.05778 | 0.31 | 0.39958 | 0.55 | 5433.99 |
| F1WSL_18 | 0.01703 | 0.79 | 0.00439 | 0.69 | 5632.38 |
| F1WSL_19 | 0.45479 | 0.57 | 0.00037 | 0.73 | 6142.29 |
| F1WSL_20 | 0.23853 | 0.62 | 0.00014 | 0.76 | 6190.17 |
| F1WSL_21 | 0.19578 | 0.36 | 0.22700 | 0.42 | 6449.89 |
| F1WSL_22 | 0.05778 | 0.30 | 0.00598 | 0.31 | 6632.47 |
| F1WSL_23 | 0.04730 | 0.31 | 0.01387 | 0.34 | 6806.45 |
| F1WSL_24 | 0.01574 | 0.72 | 0.64952 | 0.49 | 7184.12 |
| F1WSL_25 | 0.02146 | 0.79 | 0.48500 | 0.45 | 7481.21 |
| F1WSL_26 | 0.00017 | 0.86 | 0.00032 | 0.73 | 7554.75 |
| F1WSL_27 | 0.05060 | 0.70 | 0.00037 | 0.72 | 7735.75 |
| F1WSL_28 | 0.54604 | 0.46 | 0.14962 | 0.40 | 8128.46 |
| F1WSL_29 | 0.45479 | 0.40 | 0.19854 | 0.42 | 8142.18 |
| F1WSL_30 | 0.38845 | 0.42 | 0.18350 | 0.42 | 8335.48 |
| F1WSL_31 | 0.40445 | 0.40 | 0.11810 | 0.40 | 8351.32 |
| F1WSL_32 | 0.01988 | 0.25 | 0.00540 | 0.32 | 8932.95 |
| F1WSL_33 | 0.00967 | 0.76 | 0.00019 | 0.76 | 10409.97 |
| F1WSL_34 | 0.00751 | 0.76 | 0.00023 | 0.74 | 10539.14 |
| F1WSL_35 | 0.97707 | 0.52 | 0.00807 | 0.68 | 11232.39 |
| F1WSL_36 | 0.27465 | 0.64 | 0.01013 | 0.64 | 12703.49 |
| F1WSL_37 | 0.52709 | 0.43 | 0.00108 | 0.70 | 28719.77 |
| F1WSL_38 | 0.26222 | 0.38 | 0.00834 | 0.68 | 36932.80 |

TABLE 2I

F1WSH

| Master ID | Chagas vs Healthy p-value | ROC | Chagas vs Non-Chagas p-value | ROC | M/Z Average (Da) |
|---|---|---|---|---|---|
| F1WSH_1 | 0.22056 | 0.36 | 0.22056 | 0.36 | 10006.31 |
| F1WSH_2 | 0.15041 | 0.35 | 0.15041 | 0.35 | 10069.27 |
| F1WSH_3 | 0.15811 | 0.35 | 0.15811 | 0.35 | 10073.29 |
| F1WSH_4 | 0.15041 | 0.35 | 0.15041 | 0.35 | 10075.50 |
| F1WSH_5 | 0.12902 | 0.33 | 0.12902 | 0.33 | 10077.45 |
| F1WSH_6 | 0.12244 | 0.33 | 0.12244 | 0.33 | 10078.60 |
| F1WSH_7 | 0.12244 | 0.33 | 0.12244 | 0.33 | 10079.39 |
| F1WSH_8 | 0.12902 | 0.33 | 0.12902 | 0.33 | 10080.13 |
| F1WSH_9 | 0.15041 | 0.35 | 0.15041 | 0.35 | 10082.30 |
| F1WSH_10 | 0.05189 | 0.29 | 0.05189 | 0.29 | 10100.16 |
| F1WSH_11 | 0.83129 | 0.46 | 0.83129 | 0.46 | 12723.86 |
| F1WSH_12 | 0.19192 | 0.39 | 0.19192 | 0.39 | 12929.77 |
| F1WSH_13 | 0.00838 | 0.26 | 0.00838 | 0.26 | 13589.55 |
| F1WSH_14 | 0.25215 | 0.36 | 0.25215 | 0.36 | 13952.94 |
| F1WSH_15 | 0.31155 | 0.61 | 0.31155 | 0.61 | 15661.83 |
| F1WSH_16 | 0.20114 | 0.39 | 0.20114 | 0.39 | 16271.62 |
| F1WSH_17 | 0.83129 | 0.46 | 0.83129 | 0.46 | 16516.70 |
| F1WSH_18 | 0.63168 | 0.51 | 0.63168 | 0.51 | 16788.70 |
| F1WSH_19 | 0.89407 | 0.51 | 0.89407 | 0.51 | 18621.48 |
| F1WSH_20 | 0.91517 | 0.46 | 0.91517 | 0.46 | 28729.81 |
| F1WSH_21 | 0.93632 | 0.54 | 0.93632 | 0.54 | 28889.99 |
| F1WSH_22 | 0.61286 | 0.49 | 0.61286 | 0.49 | 31730.11 |

TABLE 2I-continued

F1WSH

| Master ID | Chagas vs Healthy p-value | ROC | Chagas vs Non-Chagas p-value | ROC | M/Z Average (Da) |
|---|---|---|---|---|---|
| F1WSH_23 | 0.43993 | 0.41 | 0.43993 | 0.41 | 53928.97 |
| F1WSH_24 | 0.02529 | 0.26 | 0.02529 | 0.26 | 61867.95 |
| F1WSH_25 | 0.04876 | 0.31 | 0.04876 | 0.31 | 62260.46 |
| F1WSH_26 | 0.06230 | 0.31 | 0.06230 | 0.31 | 62368.09 |
| F1WSH_27 | 0.24129 | 0.40 | 0.24129 | 0.40 | 62937.29 |

TABLE 2J

F2WSL

| Master ID | Chagas vs Healthy p-value | ROC | Chagas vs Non-Chagas p-value | ROC | M/Z Average (Da) |
|---|---|---|---|---|---|
| F2WSL_1 | 0.51232 | 0.55 | 0.09931 | 0.61 | 2990.88 |
| F2WSL_2 | 0.95646 | 0.47 | 0.12505 | 0.40 | 4071.70 |
| F2WSL_3 | 0.00319 | 0.78 | 0.00783 | 0.66 | 4394.77 |
| F2WSL_4 | 0.07157 | 0.71 | 0.03762 | 0.61 | 4575.09 |
| F2WSL_5 | 0.93472 | 0.50 | 0.57072 | 0.54 | 4810.17 |
| F2WSL_6 | 0.10723 | 0.35 | 0.50128 | 0.55 | 5452.99 |
| F2WSL_7 | 0.36762 | 0.42 | 0.00471 | 0.33 | 34200.33 |

TABLE 2K

F2WSH

| Master ID | Chagas vs Healthy p-value | ROC | Chagas vs Non-Chagas p-value | ROC | M/Z Average (Da) |
|---|---|---|---|---|---|
| F2WSH_1 | 0.93472 | 0.53 | 0.80257 | 0.48 | 17119.69 |
| F2WSH_2 | 0.53006 | 0.58 | 0.05052 | 0.62 | 28721.90 |
| F2WSH_3 | 0.70230 | 0.47 | 0.02226 | 0.36 | 31716.47 |
| F2WSH_4 | 0.64256 | 0.45 | 0.07268 | 0.37 | 32505.96 |
| F2WSH_5 | 0.84844 | 0.53 | 0.14553 | 0.43 | 33800.52 |

TABLE 2L

F5WSL

| Master ID | Chagas vs Healthy p-value | ROC | Chagas vs Non-Chagas p-value | ROC | M/Z Average (Da) |
|---|---|---|---|---|---|
| F5WSL_1 | 0.15321 | 0.66 | 0.01045 | 0.65 | 2515.32 |
| F5WSL_2 | 0.02694 | 0.72 | 0.00344 | 0.70 | 2717.45 |
| F5WSL_3 | 0.02694 | 0.75 | 0.00068 | 0.71 | 2878.07 |
| F5WSL_4 | 0.14531 | 0.64 | 0.01253 | 0.66 | 3148.08 |
| F5WSL_5 | 0.69500 | 0.46 | 0.01574 | 0.63 | 3177.70 |
| F5WSL_6 | 0.75804 | 0.56 | 0.00965 | 0.33 | 4062.36 |
| F5WSL_7 | 0.37016 | 0.41 | 0.43 | 0.54706 | 4133.16 |
| F5WSL_8 | 0.55645 | 0.42 | 0.01319 | 0.34 | 4745.72 |
| F5WSL_9 | 0.10431 | 0.68 | 0.00234 | 0.68 | 5277.01 |
| F5WSL_10 | 0.31336 | 0.61 | 0.02063 | 0.63 | 5469.51 |
| F5WSL_11 | 0.69500 | 0.56 | 0.00162 | 0.70 | 5989.66 |
| F5WSL_12 | 0.20758 | 0.65 | 0.00248 | 0.68 | 6008.46 |
| F5WSL_13 | 0.73682 | 0.51 | 0.00195 | 0.69 | 6192.91 |
| F5WSL_14 | 0.11681 | 0.35 | 0.54149 | 0.47 | 6231.01 |
| F5WSL_15 | 0.13773 | 0.35 | 0.31176 | 0.42 | 6334.92 |
| F5WSL_16 | 0.40081 | 0.42 | 0.32952 | 0.55 | 6451.57 |
| F5WSL_17 | 0.00016 | 0.12 | 0.00003 | 0.23 | 6836.65 |
| F5WSL_18 | 0.44956 | 0.45 | 0.47720 | 0.54 | 8128.52 |
| F5WSL_19 | 0.95533 | 0.51 | 0.13035 | 0.58 | 8579.30 |

TABLE 2L-continued

F5WSL

| Master ID | Chagas vs Healthy p-value | ROC | Chagas vs Non-Chagas p-value | ROC | M/Z Average (Da) |
|---|---|---|---|---|---|
| F5WSL_20 | 0.02165 | 0.29 | 0.54149 | 0.45 | 8947.28 |
| F5WSL_21 | 0.40081 | 0.40 | 0.24713 | 0.58 | 9291.62 |
| F5WSL_22 | 0.00155 | 0.84 | 0.00091 | 0.71 | 15267.51 |
| F5WSL_23 | 0.03105 | 0.75 | 0.06433 | 0.62 | 48884.47 |

TABLE 2M

F5WSH

| Master ID | Chagas vs Healthy p-value | ROC | Chagas vs Non-Chagas p-value | ROC | M/Z Average (Da) |
|---|---|---|---|---|---|
| F5WSH_1 | 0.10129 | 0.69 | 0.000006 | 0.80 | 10036.09 |
| F5WSH_2 | 0.10129 | 0.64 | 0.000048 | 0.75 | 10112.27 |
| F5WSH_3 | 0.86305 | 0.55 | 0.000097 | 0.74 | 10207.38 |
| F5WSH_4 | 0.07949 | 0.69 | 0.000638 | 0.73 | 10435.82 |
| F5WSH_5 | 0.25018 | 0.59 | 0.000406 | 0.71 | 10775.19 |
| F5WSH_6 | 0.01988 | 0.74 | 0.000009 | 0.77 | 10896.88 |
| F5WSH_7 | 0.03339 | 0.72 | 0.000000 | 0.88 | 10973.45 |
| F5WSH_8 | 0.00369 | 0.79 | 0.000005 | 0.80 | 11106.17 |
| F5WSH_9 | 0.00105 | 0.84 | 0.589417 | 0.50 | 11865.96 |
| F5WSH_10 | 0.37283 | 0.41 | 0.003806 | 0.69 | 12112.62 |
| F5WSH_11 | 0.93127 | 0.50 | 0.000617 | 0.71 | 13397.15 |
| F5WSH_12 | 0.02494 | 0.69 | 0.723651 | 0.51 | 13539.82 |
| F5WSH_13 | 0.01574 | 0.76 | 0.830538 | 0.50 | 14038.99 |
| F5WSH_14 | 0.14261 | 0.67 | 0.874313 | 0.48 | 14063.23 |
| F5WSH_15 | 0.19578 | 0.64 | 0.000077 | 0.76 | 15260.86 |
| F5WSH_16 | 0.00062 | 0.81 | 0.002652 | 0.69 | 15395.25 |
| F5WSH_17 | 0.00142 | 0.81 | 0.017657 | 0.62 | 15592.45 |
| F5WSH_18 | 0.02686 | 0.69 | 0.045442 | 0.62 | 17743.31 |
| F5WSH_19 | 0.21640 | 0.36 | 0.003279 | 0.68 | 17901.53 |
| F5WSH_20 | 0.25018 | 0.36 | 0.001661 | 0.68 | 18093.56 |
| F5WSH_21 | 0.45479 | 0.41 | 0.032346 | 0.65 | 18761.64 |
| F5WSH_22 | 0.03108 | 0.29 | 0.397140 | 0.55 | 21983.97 |
| F5WSH_23 | 0.70861 | 0.53 | 0.003920 | 0.31 | 23152.28 |
| F5WSH_24 | 0.02890 | 0.30 | 0.000576 | 0.72 | 24913.62 |
| F5WSH_25 | 0.75183 | 0.52 | 0.004158 | 0.31 | 29155.34 |
| F5WSH_26 | 0.03339 | 0.29 | 0.260214 | 0.41 | 33508.17 |
| F5WSH_27 | 0.54604 | 0.46 | 0.007574 | 0.33 | 51295.58 |
| F5WSH_28 | 0.79584 | 0.48 | 0.000329 | 0.28 | 56742.73 |
| F5WSH_29 | 0.28748 | 0.42 | 0.004409 | 0.32 | 59336.98 |
| F5WSH_30 | 0.28748 | 0.39 | 0.004409 | 0.32 | 59669.53 |
| F5WSH_31 | 0.19578 | 0.34 | 0.005098 | 0.33 | 60588.18 |
| F5WSH_32 | 0.13494 | 0.34 | 0.002071 | 0.69 | 75823.33 |
| F5WSH_33 | 0.50848 | 0.57 | 0.002136 | 0.33 | 95220.61 |
| F5WSH_34 | 0.04418 | 0.29 | | | |

TABLE 2N

F4WSL

| Master ID | Chagas vs Healthy p-value | ROC | Chagas vs Non-Chagas p-value | ROC | M/Z Average (Da) |
|---|---|---|---|---|---|
| F4WSL_1 | 0.00317 | 0.80 | 0.000127 | 0.73 | 3010.33 |
| F4WSL_2 | 0.73348 | 0.53 | 0.001180 | 0.69 | 3178.31 |
| F4WSL_3 | 0.05728 | 0.72 | 0.606858 | 0.49 | 3382.81 |
| F4WSL_4 | 0.30701 | 0.64 | 0.046159 | 0.63 | 3969.24 |
| F4WSL_5 | 0.33467 | 0.42 | 0.639341 | 0.46 | 5019.46 |
| F4WSL_6 | 0.09410 | 0.28 | 0.963355 | 0.50 | 6458.30 |
| F4WSL_7 | 0.01156 | 0.78 | 0.002083 | 0.71 | 7564.24 |
| F4WSL_8 | 0.22241 | 0.67 | 0.001386 | 0.70 | 7737.45 |
| F4WSL_9 | 0.18232 | 0.38 | 0.832623 | 0.49 | 8132.25 |
| F4WSL_10 | 0.64983 | 0.44 | 0.538133 | 0.45 | 8150.86 |

TABLE 2N-continued

F4WSL

| Master ID | Chagas vs Healthy | | Chagas vs Non-Chagas | | M/Z Average (Da) |
|---|---|---|---|---|---|
| | p-value | ROC | p-value | ROC | |
| F4WSL_11 | 0.25637 | 0.33 | 0.144018 | 0.42 | 8943.87 |
| F4WSL_12 | 0.21184 | 0.36 | 0.706371 | 0.50 | 9305.26 |
| F4WSL_13 | | | | | |

TABLE 2O

F4WSH

| Master ID | Chagas vs Healthy | | Chagas vs Non-Chagas | | M/Z Average (Da) |
|---|---|---|---|---|---|
| | p-value | ROC | p-value | ROC | |
| F4WSH_1 | 0.17971 | 0.39 | 0.722112 | 0.47 | 10111.80 |
| F4WSH_2 | 0.14704 | 0.62 | 0.617205 | 0.47 | 13601.95 |
| F4WSH_3 | 0.37839 | 0.63 | 0.152097 | 0.58 | 24762.11 |
| F4WSH_4 | 0.03813 | 0.28 | 0.000041 | 0.24 | 95163.38 |

TABLE 2P

F6WSL

| Master ID | Chagas vs Healthy | | Chagas vs Non-Chagas | | M/Z Average (Da) |
|---|---|---|---|---|---|
| | p-value | ROC | p-value | ROC | |
| F6WSL_1 | 0.63168 | 0.46 | 0.427855 | 0.44 | 3110.28 |
| F6WSL_2 | 0.81058 | 0.51 | 0.717381 | 0.49 | 3321.25 |
| F6WSL_3 | 0.59429 | 0.44 | 0.208303 | 0.42 | 3330.05 |
| F6WSL_4 | 0.68955 | 0.41 | 0.623261 | 0.54 | 6631.71 |
| F6WSL_5 | 0.29898 | 0.64 | 0.972500 | 0.51 | 6844.57 |
| F6WSL_6 | 0.29898 | 0.41 | 0.388791 | 0.45 | 8938.10 |
| F6WSL_7 | 0.57599 | 0.46 | 0.258908 | 0.42 | 48509.95 |
| F6WSL_8 | 0.03313 | 0.29 | 0.000935 | 0.27 | 48614.08 |
| F6WSL_9 | 0.00201 | 0.18 | 0.037016 | 0.36 | 65062.92 |
| F6WSL_10 | 0.32445 | 0.39 | 0.023417 | 0.37 | 73971.36 |

TABLE 2Q

F6WSH

| Master ID | Chagas vs Healthy | | Chagas vs Non-Chagas | | M/Z Average (Da) |
|---|---|---|---|---|---|
| | p-value | ROC | p-value | ROC | |
| F6WSH_1 | 0.63168 | 0.46 | 0.427855 | 0.44 | 3110.28 |
| F6WSH_2 | 0.81058 | 0.51 | 0.717381 | 0.49 | 3321.25 |
| F6WSH_3 | 0.59429 | 0.44 | 0.208303 | 0.42 | 3330.05 |
| F6WSH_4 | 0.68955 | 0.41 | 0.623261 | 0.54 | 6631.71 |
| F6WSH_5 | 0.29898 | 0.64 | 0.972500 | 0.51 | 6844.57 |
| F6WSH_6 | 0.29898 | 0.41 | 0.388791 | 0.45 | 8938.10 |
| F6WSH_7 | 0.57599 | 0.46 | 0.258908 | 0.42 | 48509.95 |
| F6WSH_8 | 0.03313 | 0.29 | 0.000935 | 0.27 | 48614.08 |
| F6WSH_9 | 0.00201 | 0.18 | 0.037016 | 0.36 | 65062.92 |
| F6WSLH_10 | 0.32445 | 0.39 | 0.023417 | 0.37 | 73971.36 |

TABLE 2R

F1ISL

| Master ID | Chagas vs Healthy | | Chagas vs Non-Chagas | | M/Z Average (Da) |
|---|---|---|---|---|---|
| | p-value | ROC | p-value | ROC | |
| F1ISL_1 | 0.47233 | 0.59 | 0.00008 | 0.76 | 3183.51 |
| F1ISL_2 | 0.52709 | 0.57 | 0.00000 | 0.81 | 3200.64 |
| F1ISL_3 | 0.38845 | 0.41 | 0.85509 | 0.52 | 3292.18 |
| F1ISL_4 | 0.01454 | 0.76 | 0.00023 | 0.71 | 3788.89 |
| F1ISL_5 | 0.66631 | 0.55 | 0.00197 | 0.69 | 3877.48 |
| F1ISL_6 | 0.02686 | 0.26 | 0.00191 | 0.32 | 3903.41 |
| F1ISL_7 | 0.00095 | 0.15 | 0.00472 | 0.32 | 4073.87 |
| F1ISL_8 | 0.01703 | 0.27 | 0.00239 | 0.31 | 4105.74 |
| F1ISL_9 | 0.02146 | 0.25 | 0.00088 | 0.28 | 4175.72 |
| F1ISL_10 | 0.23853 | 0.38 | 0.00004 | 0.22 | 4230.14 |
| F1ISL_11 | 0.81810 | 0.46 | 0.00217 | 0.32 | 4238.67 |
| F1ISL_12 | 0.19578 | 0.38 | 0.00028 | 0.26 | 4260.76 |
| F1ISL_13 | 0.34278 | 0.40 | 0.00458 | 0.32 | 4275.27 |
| F1ISL_14 | 0.02146 | 0.29 | 0.00894 | 0.34 | 4292.31 |
| F1ISL_15 | 0.31433 | 0.40 | 0.00501 | 0.33 | 4351.52 |
| F1ISL_16 | 0.08986 | 0.31 | 0.00016 | 0.26 | 4481.20 |
| F1ISL_17 | 0.03108 | 0.29 | 0.00307 | 0.67 | 4661.41 |
| F1ISL_18 | 0.04730 | 0.69 | 0.00869 | 0.68 | 4797.37 |
| F1ISL_19 | 0.45479 | 0.57 | 0.01028 | 0.65 | 4811.15 |
| F1ISL_20 | 0.58492 | 0.57 | 0.00246 | 0.68 | 5154.34 |
| F1ISL_21 | 0.02314 | 0.69 | 0.00069 | 0.71 | 5288.40 |
| F1ISL_22 | 0.00689 | 0.76 | 0.00000 | 0.82 | 5380.40 |
| F1ISL_23 | 0.01841 | 0.74 | 0.00074 | 0.71 | 5591.40 |
| F1ISL_24 | 0.42085 | 0.58 | 0.00091 | 0.72 | 5620.59 |
| F1ISL_25 | 0.03339 | 0.72 | 0.00239 | 0.67 | 5635.51 |
| F1ISL_26 | 0.75183 | 0.57 | 0.03446 | 0.35 | 5764.27 |
| F1ISL_27 | 0.25018 | 0.62 | 0.00058 | 0.70 | 6007.31 |
| F1ISL_28 | 0.01841 | 0.74 | 0.00016 | 0.74 | 6067.44 |
| F1ISL_29 | 0.15894 | 0.67 | 0.00001 | 0.78 | 6145.12 |
| F1ISL_30 | 0.30070 | 0.62 | 0.00000 | 0.82 | 6191.34 |
| F1ISL_31 | 0.00443 | 0.79 | 0.00000 | 0.81 | 6217.49 |
| F1ISL_32 | 0.00307 | 0.81 | 0.00006 | 0.75 | 6256.47 |
| F1ISL_33 | 0.00173 | 0.81 | 0.00271 | 0.67 | 6292.96 |
| F1ISL_34 | 0.00190 | 0.81 | 0.00000 | 0.80 | 6348.54 |
| F1ISL_35 | 0.00190 | 0.81 | 0.00001 | 0.76 | 6377.81 |
| F1ISL_36 | 0.02890 | 0.74 | 0.00001 | 0.78 | 6398.74 |
| F1ISL_37 | 0.18603 | 0.64 | 0.00020 | 0.75 | 6532.08 |
| F1ISL_38 | 0.31433 | 0.38 | 0.01057 | 0.34 | 6808.21 |
| F1ISL_39 | 0.54604 | 0.52 | 0.08889 | 0.39 | 7190.03 |
| F1ISL_40 | 0.00578 | 0.81 | 0.00564 | 0.69 | 7429.92 |
| F1ISL_41 | 0.01454 | 0.76 | 0.03208 | 0.64 | 7487.05 |
| F1ISL_42 | 0.01574 | 0.76 | 0.00000 | 0.80 | 7555.93 |
| F1ISL_43 | 0.75183 | 0.53 | 0.00022 | 0.74 | 7738.82 |
| F1ISL_44 | 0.00443 | 0.21 | 0.03365 | 0.36 | 8129.09 |
| F1ISL_45 | 0.00529 | 0.23 | 0.04354 | 0.37 | 8144.24 |
| F1ISL_46 | 0.00336 | 0.17 | 0.03529 | 0.41 | 8334.56 |
| F1ISL_47 | 0.00631 | 0.20 | 0.06638 | 0.39 | 8349.58 |
| F1ISL_48 | 0.02146 | 0.22 | 0.00776 | 0.33 | 8440.26 |
| F1ISL_49 | 0.01703 | 0.26 | 0.00945 | 0.34 | 8449.38 |
| F1ISL_50 | 0.01988 | 0.29 | 0.02450 | 0.32 | 8457.02 |
| F1ISL_51 | 0.28748 | 0.42 | 0.01147 | 0.32 | 8642.68 |
| F1ISL_52 | 0.64554 | 0.47 | 0.00108 | 0.28 | 8675.93 |
| F1ISL_53 | 0.05060 | 0.29 | 0.00074 | 0.30 | 8741.03 |
| F1ISL_54 | 0.00889 | 0.24 | 0.00348 | 0.32 | 8933.11 |
| F1ISL_55 | 0.00307 | 0.19 | 0.00458 | 0.30 | 8949.87 |
| F1ISL_56 | 0.02494 | 0.27 | 0.86264 | 0.51 | 9154.81 |
| F1ISL_57 | 0.03585 | 0.27 | 0.00869 | 0.69 | 9254.28 |
| F1ISL_58 | 0.05060 | 0.29 | 0.00239 | 0.70 | 9302.80 |
| F1ISL_59 | 0.07949 | 0.29 | 0.00137 | 0.71 | 9372.34 |
| F1ISL_60 | 0.06579 | 0.34 | 0.00162 | 0.72 | 9512.39 |
| F1ISL_61 | 0.05060 | 0.69 | 0.00203 | 0.69 | 10425.58 |
| F1ISL_62 | 0.00967 | 0.79 | 0.00108 | 0.72 | 12728.23 |
| F1ISL_63 | 0.16762 | 0.36 | 0.00337 | 0.68 | 28797.66 |
| F1ISL_64 | 0.13494 | 0.64 | 0.06089 | 0.62 | 36203.31 |
| F1ISL_65 | 0.05778 | 0.32 | 0.00116 | 0.30 | 67405.39 |

TABLE 2S

F1ISH check this out

| Master ID | Chagas vs Healthy p-value | ROC | Chagas vs Non-Chagas p-value | ROC | M/Z Average (Da) |
|---|---|---|---|---|---|
| F1ISH_1 | 0.02708 | 0.71 | 0.00163 | 0.68 | 10414.53 |
| F1ISH_2 | 1.00000 | 0.49 | 0.00509 | 0.37 | 11743.97 |
| F1ISH_3 | 0.00715 | 0.76 | 0.00003 | 0.78 | 12714.74 |
| F1ISH_4 | 0.40905 | 0.39 | 0.50029 | 0.47 | 13588.84 |
| F1ISH_5 | 0.07438 | 0.33 | 0.06602 | 0.40 | 16312.03 |
| F1ISH_6 | 0.08345 | 0.29 | 0.00495 | 0.66 | 28774.99 |
| F1ISH_7 | 0.00201 | 0.20 | 0.01810 | 0.35 | 69109.75 |

TABLE 2T

F2ISL

| Master ID | Chagas vs Healthy p-value | ROC | Chagas vs Non-Chagas p-value | ROC | M/Z Average (Da) |
|---|---|---|---|---|---|
| F2ISL_1 | 0.21069 | 0.36 | 0.01438 | 0.35 | 3509.87 |
| F2ISL_2 | 0.06230 | 0.71 | 0.75637 | 0.53 | 4078.84 |
| F2ISL_3 | 0.00127 | 0.81 | 0.00005 | 0.75 | 4397.12 |
| F2ISL_4 | 0.15041 | 0.66 | 0.00434 | 0.67 | 4429.43 |
| F2ISL_5 | 0.03539 | 0.66 | 0.00368 | 0.69 | 4510.82 |
| F2ISL_6 | 0.08345 | 0.66 | 0.00015 | 0.73 | 4582.77 |
| F2ISL_7 | 0.97875 | 0.54 | 0.00106 | 0.70 | 6147.07 |
| F2ISL_8 | 0.12244 | 0.31 | 0.03473 | 0.38 | 8155.79 |
| F2ISL_9 | 0.42433 | 0.41 | 0.49054 | 0.47 | 8356.10 |
| F2ISL_10 | 0.17440 | 0.39 | 0.04650 | 0.37 | 43543.21 |
| F2ISL_11 | 0.59429 | 0.44 | 0.01101 | 0.33 | 49105.79 |

TABLE 2U

F2ISH

| Master ID | Chagas vs Healthy p-value | ROC | Chagas vs Non-Chagas p-value | ROC | M/Z Average (Da) |
|---|---|---|---|---|---|
| F2ISH_1 | 0.12902 | 0.38 | 0.14526 | 0.40 | 10982.95 |
| F2ISH_2 | 0.39410 | 0.40 | 0.11676 | 0.39 | 11832.63 |
| F2ISH_3 | 0.50555 | 0.41 | 0.76951 | 0.52 | 37709.02 |
| F2ISH_4 | 0.15811 | 0.34 | 0.86315 | 0.48 | 54031.83 |
| F2ISH_5 | 0.15041 | 0.36 | 0.02504 | 0.37 | 88226.08 |
| F2ISH_6 | 0.15811 | 0.34 | 0.95190 | 0.49 | 89062.98 |
| F2ISH_7 | 0.63168 | 0.41 | 0.51248 | 0.55 | 89941.18 |
| F2ISH_8 | 0.61286 | 0.44 | 0.31745 | 0.44 | 91183.36 |

TABLE 2V

F3ISL

| Master ID | Chagas vs Healthy p-value | ROC | Chagas vs Non-Chagas p-value | ROC | M/Z Average (Da) |
|---|---|---|---|---|---|
| F3ISL_1 | 0.94291 | 0.53 | 0.39164 | 0.56 | 4160.88 |
| F3ISL_2 | 0.54272 | 0.43 | 0.64776 | 0.53 | 4819.12 |
| F3ISL_3 | 1.00000 | 0.52 | 0.11236 | 0.62 | 5992.34 |
| F3ISL_4 | 0.26701 | 0.70 | 0.00752 | 0.68 | 6149.50 |
| F3ISL_5 | 0.09240 | 0.27 | 0.82819 | 0.48 | 8145.73 |
| F3ISL_6 | 0.18523 | 0.33 | 0.68093 | 0.48 | 8963.86 |
| F3ISL_7 | 0.13262 | 0.30 | 0.00921 | 0.32 | 28930.20 |
| F3ISL_8 | 0.00650 | 0.21 | 0.00247 | 0.28 | 30705.35 |

TABLE 2W

F3ISH

| Master ID | Chagas vs Healthy p-value | ROC | Chagas vs Non-Chagas p-value | ROC | M/Z Average (Da) |
|---|---|---|---|---|---|
| F3ISH_1 | 0.63594 | 0.56 | 0.51746 | 0.46 | 10257.40 |
| F3ISH_2 | 0.89241 | 0.50 | 0.99229 | 0.50 | 10444.29 |
| F3ISH_3 | 0.54277 | 0.44 | 0.00234 | 0.33 | 11642.51 |
| F3ISH_4 | 0.17621 | 0.66 | 0.00086 | 0.72 | 24919.40 |
| F3ISH_5 | 0.01121 | 0.22 | 0.00063 | 0.30 | 29079.28 |
| F3ISH_6 | 0.00683 | 0.22 | 0.00015 | 0.26 | 30617.80 |
| F3ISH_7 | 0.01636 | 0.22 | 0.00022 | 0.28 | 37518.65 |

TABLE 2X

F4ISL

| Master ID | Chagas vs Healthy p-value | ROC | Chagas vs Non-Chagas p-value | ROC | M/Z Average (Da) |
|---|---|---|---|---|---|
| F4ISL_1 | 0.14261 | 0.64 | 0.00233 | 0.71 | 3174.20 |
| F4ISL_2 | 0.11385 | 0.65 | 0.00557 | 0.71 | 3191.33 |
| F4ISL_3 | 0.64554 | 0.57 | 0.00217 | 0.69 | 3782.82 |
| F4ISL_4 | 0.19578 | 0.62 | 0.02666 | 0.66 | 3824.52 |
| F4ISL_5 | 0.06579 | 0.69 | 0.00005 | 0.75 | 5380.50 |
| F4ISL_6 | 0.04730 | 0.69 | 0.00021 | 0.75 | 6008.33 |
| F4ISL_7 | 0.95415 | 0.52 | 0.00415 | 0.67 | 6192.58 |
| F4ISL_8 | 0.01342 | 0.76 | 0.00065 | 0.72 | 7562.65 |
| F4ISL_9 | 0.28748 | 0.34 | 0.61863 | 0.48 | 8144.89 |
| F4ISL_10 | 0.08455 | 0.31 | 0.00106 | 0.29 | 8945.38 |
| F4ISL_11 | 0.03585 | 0.29 | 0.01359 | 0.34 | 30027.72 |
| F4ISL_12 | 0.04124 | 0.31 | 0.02666 | 0.36 | 51843.34 |

TABLE 3

Preferred Biomarkers: Chagas vs Healthy

| Master ID | Chagas vs Healthy p-value | ROC | M/Z Average (Da) |
|---|---|---|---|
| F6ISH_15 | 0.00030 | 0.90 | 75426.74 |
| F4ISH_4 | 0.00501 | 0.19 | 14076.61 |
| F4ISH_5 | 0.00092 | 0.17 | 14162.34 |
| F4ISH_6 | 0.00074 | 0.17 | 14203.94 |
| F4ISH_7 | 0.00172 | 0.17 | 14252.34 |
| F4ISH_9 | 0.00501 | 0.21 | 28866.98 |
| F3WSH_1 | 0.00556 | 0.25 | 10110.75 |
| F3WSH_8 | 0.00510 | 0.79 | 24893.62 |
| F3WSL_12 | 0.00292 | 0.81 | 3932.19 |
| F3WSL_14 | 0.00223 | 0.19 | 4077.76 |
| F3WSL_20 | 0.00087 | 0.86 | 5380.70 |
| F1WSL_26 | 0.00017 | 0.86 | 7554.75 |
| F2WSL_3 | 0.00319 | 0.78 | 4394.77 |
| F5WSL_17 | 0.00016 | 0.12 | 6836.65 |
| F5WSL_22 | 0.00155 | 0.84 | 15267.51 |
| F5WSH_8 | 0.00369 | 0.79 | 11106.17 |
| F5WSH_9 | 0.00105 | 0.84 | 11865.96 |
| F5WSH_16 | 0.00062 | 0.81 | 15395.25 |
| F5WSH_17 | 0.00142 | 0.81 | 15592.45 |
| F4WSL_1 | 0.00317 | 0.80 | 3010.33 |
| F6WSH_9 | 0.00201 | 0.18 | 65062.92 |
| F6WSH_9 | 0.00201 | 0.18 | 65062.92 |
| F1ISL_7 | 0.00095 | 0.15 | 4073.87 |
| F1ISL_31 | 0.00443 | 0.79 | 6217.49 |
| F1ISL_32 | 0.00307 | 0.81 | 6256.47 |
| F1ISL_33 | 0.00173 | 0.81 | 6292.96 |
| F1ISL_34 | 0.00190 | 0.81 | 6348.54 |
| F1ISL_35 | 0.00190 | 0.81 | 6377.81 |
| F1ISL_40 | 0.00578 | 0.81 | 7429.92 |
| F1ISL_44 | 0.00443 | 0.21 | 8129.09 |

TABLE 3-continued

Preferred Biomarkers: Chagas vs Healthy

| Master ID | Chagas vs Healthy p-value | ROC | M/Z Average (Da) |
|---|---|---|---|
| F1ISL_45 | 0.00529 | 0.23 | 8144.24 |
| F1ISL_46 | 0.00336 | 0.17 | 8334.56 |
| F1ISL_55 | 0.00307 | 0.19 | 8949.87 |
| F1ISH_7 | 0.00201 | 0.20 | 69109.75 |
| F2ISL_3 | 0.00127 | 0.81 | 4397.12 |

TABLE 4

Preferred Biomarkers: Chagas vs Non-Chagas

| Master ID | Chagas vs Non-Chagas p-value | ROC | M/Z Average (Da) |
|---|---|---|---|
| F5ISL_6 | 0.00005 | 0.76 | 3170.99 |
| F5ISL_13 | 0.00047 | 0.71 | 75548.95 |
| F5ISH_2 | 0.00004 | 0.26 | 28036.18 |
| F5ISH_3 | 0.00006 | 0.24 | 28269.46 |
| F5ISH_7 | 0.00030 | 0.29 | 59454.95 |
| F5ISH_9 | 0.00060 | 0.71 | 75647.95 |
| F5ISH_10 | 0.00012 | 0.75 | 103795.90 |
| F6ISH_8 | 0.00044 | 0.27 | 55962.00 |
| F6ISH_9 | 0.00037 | 0.27 | 56167.48 |
| F6ISH_10 | 0.00119 | 0.27 | 56414.40 |
| F6ISH_11 | 0.00015 | 0.26 | 57022.49 |
| F6ISH_12 | 0.00014 | 0.28 | 57908.91 |
| F6ISH_15 | 0.00003 | 0.77 | 75426.74 |
| F6ISL_9 | 0.00078 | 0.29 | 44015.50 |
| F6ISL_11 | 0.00047 | 0.28 | 56807.45 |
| F4ISH_5 | 0.00045 | 0.26 | 14162.34 |
| F4ISH_6 | 0.00006 | 0.25 | 14203.94 |
| F4ISH_7 | 0.00018 | 0.26 | 14252.34 |
| F4ISH_11 | 0.00029 | 0.74 | 75141.77 |
| F4ISH_12 | 0.00064 | 0.70 | 100518.18 |
| F3WSH_8 | 0.00000 | 0.80 | 24893.62 |
| F3WSL_4 | 0.000018 | 0.76 | 3013.11 |
| F3WSL_17 | 0.000003 | 0.79 | 4242.16 |
| F3WSL_20 | 0.000006 | 0.78 | 5380.70 |
| F3WSL_23 | 0.000002 | 0.80 | 5988.65 |
| F3WSL_24 | 0.000016 | 0.76 | 6008.67 |
| F3WSL_25 | 0.000025 | 0.77 | 6146.33 |
| F3WSL_26 | 0.000010 | 0.79 | 6192.87 |
| F3WSL_29 | 0.000006 | 0.21 | 6499.23 |
| F3WSL_31 | 0.000002 | 0.77 | 6877.34 |
| F3WSL_39 | 0.000008 | 0.78 | 24827.43 |
| F1WSL_8 | 0.00088 | 0.72 | 3873.66 |
| F1WSL_12 | 0.00126 | 0.73 | 4396.10 |
| F1WSL_16 | 0.00022 | 0.75 | 5378.75 |
| F1WSL_19 | 0.00037 | 0.73 | 6142.29 |
| F1WSL_20 | 0.00014 | 0.76 | 6190.17 |
| F1WSL_26 | 0.00032 | 0.73 | 7554.75 |
| F1WSL_27 | 0.00037 | 0.72 | 7735.75 |
| F1WSL_33 | 0.00019 | 0.76 | 10409.97 |
| F1WSL_34 | 0.00023 | 0.74 | 10539.14 |
| F5WSL_2 | 0.00344 | 0.70 | 2717.45 |
| F5WSL_3 | 0.00068 | 0.71 | 2878.07 |
| F5WSL_11 | 0.00162 | 0.70 | 5989.66 |
| F5WSL_17 | 0.00003 | 0.23 | 6836.65 |
| F5WSL_22 | 0.00091 | 0.71 | 15267.51 |
| F5WSH_1 | 0.000006 | 0.80 | 10036.09 |
| F5WSH_2 | 0.000048 | 0.75 | 10112.27 |
| F5WSH_3 | 0.000097 | 0.74 | 10207.38 |
| F5WSH_6 | 0.000009 | 0.77 | 10896.88 |
| F5WSH_7 | 0.000000 | 0.88 | 10973.45 |
| F5WSH_8 | 0.000005 | 0.80 | 11106.17 |
| F5WSH_15 | 0.000077 | 0.76 | 15260.86 |
| F4WSH_4 | 0.000041 | 0.24 | 95163.38 |
| F1ISL_1 | 0.00008 | 0.76 | 3183.51 |
| F1ISL_2 | 0.00000 | 0.81 | 3200.64 |
| F1ISL_4 | 0.00023 | 0.71 | 3788.89 |
| F1ISL_9 | 0.00088 | 0.28 | 4175.72 |

TABLE 4-continued

Preferred Biomarkers: Chagas vs Non-Chagas

| Master ID | Chagas vs Non-Chagas p-value | ROC | M/Z Average (Da) |
|---|---|---|---|
| F1ISL_10 | 0.00004 | 0.22 | 4230.14 |
| F1ISL_12 | 0.00028 | 0.26 | 4260.76 |
| F1ISL_16 | 0.00016 | 0.26 | 4481.20 |
| F1ISL_21 | 0.00069 | 0.71 | 5288.40 |
| F1ISL_22 | 0.00000 | 0.82 | 5380.40 |
| F1ISL_23 | 0.00074 | 0.71 | 5591.40 |
| F1ISL_24 | 0.00091 | 0.72 | 5620.59 |
| F1ISL_28 | 0.00016 | 0.74 | 6067.44 |
| F1ISL_29 | 0.00001 | 0.78 | 6145.12 |
| F1ISL_30 | 0.00000 | 0.82 | 6191.34 |
| F1ISL_31 | 0.00000 | 0.81 | 6217.49 |
| F1ISL_32 | 0.00006 | 0.75 | 6256.47 |
| F1ISL_36 | 0.00001 | 0.78 | 6398.74 |
| F1ISL_37 | 0.00020 | 0.75 | 6532.08 |
| F1ISL_42 | 0.00000 | 0.80 | 7555.93 |
| F1ISL_43 | 0.00022 | 0.74 | 7738.82 |
| F1ISL_52 | 0.00108 | 0.28 | 8675.93 |
| F1ISL_53 | 0.00074 | 0.30 | 8741.03 |
| F1ISL_58 | 0.00239 | 0.70 | 9302.80 |
| F1ISL_59 | 0.00137 | 0.71 | 9372.34 |
| F1ISL_60 | 0.00162 | 0.72 | 9512.39 |
| F1ISL_62 | 0.00108 | 0.72 | 12728.23 |
| F1ISH_3 | 0.00003 | 0.78 | 12714.74 |
| F2ISL_3 | 0.00005 | 0.75 | 4397.12 |
| F2ISL_6 | 0.00015 | 0.73 | 4582.77 |
| F3ISL_8 | 0.00247 | 0.28 | 30705.35 |
| F3ISH_4 | 0.00086 | 0.72 | 24919.40 |
| F3ISH_6 | 0.00015 | 0.26 | 30617.80 |
| F4ISL_1 | 0.00233 | 0.71 | 3174.20 |
| F4ISL_2 | 0.00557 | 0.71 | 3191.33 |
| F4ISL_5 | 0.00005 | 0.75 | 5380.50 |
| F4ISL_6 | 0.00021 | 0.75 | 6008.33 |
| F4ISL_8 | 0.00065 | 0.72 | 7562.65 |
| F4ISL_10 | 0.00106 | 0.29 | 8945.38 |

C. Use of Biomarkers to Differentiate Between Different Stages of Chagas

This example demonstrates the use of the methods of the present invention to identify biomarkers that indicate whether the individual is acutely infected versus chronically infected with Chagas disease. Samples were analyzed from chronically infected Venezuelan patients and compared to samples from acutely infected Guatemalan pediatric patients (as measured by an EKG test). The results are summarized in Table 5, below, and in FIGS. 5 and 6.

| MW (kDa) | Protein | Figure | Significance |
|---|---|---|---|
| 6.454 | Apo-1 | 6A-C | p = 0.7 |
| 8.127 | Apo-1 | 7A-C | p = 0.001 |
| 8.127 | | 7D | p = 0.2 |
| 8.351 | | 8A-C | p = 0.08 |
| 8.937 | | 9A-C | p = 0.002 |
| 9.308 | Apo-1 (C-term) | 10A-C | p = 0.218 |

D. Use of the Biomarkers to Differentiate Between Different Parasitic Diseases

This example demonstrates the use of the present methods to identify biomarkers that indicate the status in an individual of the presence or absence of Chagas disease as distinguished from a different trypanosome infection or another parasitic infection. Here, biomarkers were identified that indicated the presence or absence of Chagas disease as distinguished from a different trypanosome infection, such as African trypanosomiasis (sleeping sickness), a protozoal infection, such as babesiosis, and a parasitic infection, such as malaria. The biomarkers that specifically indicate the presence or absence of Chagas disease also were compared to uninfected individuals. Several biomarkers specific for Chagas disease were identified. For example, an 8.351 kDa biomarker and a 9.3 kDa biomarker. The presence, or the comparatively greater presence, of one or more of these biomarkers in a sample from an individual is indicative of the specific presence of a T. cruzi infection and the specific presence of Chagas disease. The results are depicted in FIGS. 7-9.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for qualifying Chagas disease status in a human subject comprising:
   a. measuring two or more biomarkers in a biological sample from the subject, wherein the two or more biomarkers comprise a fragment of a human fibronectin polypeptide and a fragment of a human ApoA1 polypeptide, wherein:
      i. the fragment of the fibronectin polypeptide is an 28.5 kDa N-terminal fragment, and
      ii. the fragment of the ApoA-1 polypeptide is selected from the group consisting of an 14 kDa C-terminal fragment, an 25 kDa N-terminal fragment, an 9 kDa C-terminal fragment, and an 10 kDa C-terminal fragment; and
   b. correlating the measurement with Chagas disease status, wherein the correlating comprises comparing the measurement to a diagnostic amount, the diagnostic amount distinguishing a positive Chagas disease status from a negative Chagas disease status.

2. The method of claim 1, further comprising measuring human macrophage inflammatory protein-1α (MIP-1α).

3. The method of any of claims 1 or 2, wherein said measuring two or more biomarkers is carried out by capturing the biomarker on an adsorbent surface of a SELDI probe and detecting the captured biomarkers by laser desorption-ionization mass spectrometry.

4. The method of any of claims 1 or 2, wherein said measuring two or more biomarkers is carried out by immunoassay.

5. The method of any of claims 1 or 2, wherein the sample is serum.

6. The method of any of claims 1 or 2, wherein the correlating is performed by a software classification algorithm that determines the subject's Chagas disease status as being positive or negative.

7. The method of any of claims 1 or 2, wherein the positive Chagas disease status is selected from chronic symptomatic, chronic asymptomatic, acute and the negative Chagas disease status is uninfected.

8. The method of any of claims 1 or 2, wherein the positive Chagas disease status is infected and the negative Chagas disease status is healthy.

9. The method of claim 1, wherein said measuring two or more biomarkers involves each of the biomarkers selected from the group consisting of the 25 kDa N-terminal fragment of ApoA-1, and the 14 kDa C-terminal fragment of ApoA-1.

10. The method of any of claims 1 or 2, wherein the negative Chagas disease status qualifies as non-Chagas disease.

11. The method of any of claims 1 or 2, further comprising:
    c. managing the subject's treatment based on the subject's Chagas disease status.

12. The method of claim 3, wherein the adsorbent is a cation exchange adsorbent.

13. The method of claim 3, wherein the adsorbent is a metal chelate adsorbent.

14. The method of claim 11, further comprising
    d. administering one or more drugs selected from the group consisting of nifurtimox, benznidazole and allopurinol to a subject having a positive Chagas disease status.

15. The method of claim 14, further comprising:
    e. measuring the two or more biomarkers after steps a-d.

16. The method of claim 1, wherein the step of measuring two or more biomarkers further includes measuring a fragment of the C3 polypeptide selected from the group consisting of an 8 kDa N-terminal fragment.

17. The method of claim 1, wherein the step of measuring two or more biomarkers further includes measuring a 110 kDa trypanosome protein M110 with homology to *Leishmania major* protein LM 15-1.32.

18. The method of claim 1, wherein the 28.5 kDa N-terminal fragment of the human fibronectin polypeptide comprises amino acid residues 1-258 of SEQ ID NO:31.

19. The method of claim 1, wherein the 14 kDa C-terminal fragment of the human ApoA1 polypeptide comprises amino acid residues 124-243 of SEQ ID NO:18.

20. The method of claim 1, wherein the 25 kDa N-terminal fragment of the human ApoA1 polypeptide comprises amino acid residues 1-214 of SEQ ID NO:18.

21. The method of claim 1, wherein the 9 kDa C-terminal fragment of the human ApoA1 polypeptide comprises amino acid residues 161-243 of SEQ ID NO:18.

22. The method of claim 1, wherein the 10 kDa C-terminal fragment of the human ApoA1 polypeptide comprises amino acid residues 154-243 of SEQ ID NO:18.

23. The method of claim 16, wherein the 8 kDa N-terminal fragment of the C3 anaphylatoxin polypeptide comprises amino acid residues 1-68 SEQ ID NO: 23.

24. The method of claim 16, wherein the 16 kDa dimmer of the C3 anaphylatoxin polypeptide comprises amino acid residues 1-68 of SEQ ID NO: 23.

* * * * *

```
                        SEQUENCE LISTING

<160> NUMBER OF SEQ ID NOS: 38

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 1

Ser Gly Ser Val Asn Phe Phe Ser Arg
  1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 2

Ala Ala Pro Pro Pro Pro Glu Pro Phe Arg
  1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 3

Leu Ser Gly Leu Ser Pro Leu Glu Arg Leu Lys
  1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 4
```

```
Val Ala Pro Pro Tyr Leu Val Arg Ala Ala Ala Arg
  1               5                  10

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 5

Leu Val Ile Ala Val Gln Ser Phe Ser Glu Leu Leu Ser Ala Thr His
  1               5                  10                  15

His Tyr Lys

<210> SEQ ID NO 6
<211> LENGTH: 18
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 6

Ala Ala Thr Leu Leu Glu Glu Glu Val Trp Met Leu Thr Leu Val
  1               5                  10                  15

Arg Arg

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 7

Arg Leu Val Ile Ala Val Gln Ser Phe Ser Glu Leu Leu Ser Ala Thr
  1               5                  10                  15

His His Tyr Lys
             20

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 8

Ala Ala Phe Ser Ser Pro Leu Thr Ser Val Ser Pro Ser Ala Pro Leu
  1               5                  10                  15

Ala Ala Leu Leu Thr Lys Ser Ile Lys
             20                  25

<210> SEQ ID NO 9
<211> LENGTH: 23
```

```
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 9

Leu Val Ile Ala Val Gln Ser Phe Ser Glu Leu Leu Ser Ala Thr His
 1               5                  10                  15

His Tyr Lys Ala Ala Gln Arg
            20

<210> SEQ ID NO 10
<211> LENGTH: 25
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 10

Leu Glu Leu Gly Leu Ala Leu Val Met Val Cys Ile Pro Leu Ala Gly
 1               5                  10                  15

Thr Glu Glu Gly Trp His Leu Met Arg
            20                  25

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence:Trypanosoma
      cruzi M110 protein (Leishmanii major LM15-1.32
      homolog) Chagas disease biomarker tryptic digest
      fragment peptide

<400> SEQUENCE: 11

Ser Asn Ser Ala Gly Val Pro Ala Ala Val Ser Ala Ser Thr Ser Thr
 1               5                  10                  15

Ser Ser Thr Ser Val Asp Arg Val Gln Thr Ile Leu Gln Ala Val His
            20                  25                  30

Val Ala Leu Thr His Ala Leu Lys Pro Val Arg
            35                  40

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence:13.6 kDa
      fragment of Apolipoprotein A-I (ApoA-I) Chagas
      disease biomarker tryptic digest fragment peptide

<400> SEQUENCE: 12

Ala Lys Pro Ala Leu Glu Asp Leu Arg
 1               5

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence:13.6 kDa
      fragment of Apolipoprotein A-I (ApoA-I) Chagas
``` disease biomarker tryptic digest fragment peptide

<400> SEQUENCE: 13

Leu Glu Ala Leu Lys Glu Asn Gly Gly Ala Arg
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence:13.6 kDa
      fragment of Apolipoprotein A-I (ApoA-I) Chagas
      disease biomarker tryptic digest fragment peptide

<400> SEQUENCE: 14

Gln Gly Leu Leu Pro Val Leu Glu Ser Phe Lys
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence:13.6 kDa
      fragment of Apolipoprotein A-I (ApoA-I) Chagas
      disease biomarker tryptic digest fragment peptide

<400> SEQUENCE: 15

Thr His Leu Ala Pro Tyr Ser Asp Glu Leu Arg
1               5                   10

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence:13.6 kDa
      fragment of Apolipoprotein A-I (ApoA-I) Chagas
      disease biomarker tryptic digest fragment peptide

<400> SEQUENCE: 16

Leu Ser Pro Leu Gly Glu Glu Met Arg Asp Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:13.6 kDa
      fragment of Apolipoprotein A-I (ApoA-I) Chagas
      disease biomarker tryptic digest fragment peptide

<400> SEQUENCE: 17

Val Ser Phe Leu Ser Ala Leu Glu Glu Tyr Thr Lys
1               5                   10

<210> SEQ ID NO 18
<211> LENGTH: 243
<212> TYPE: PRT
<213> ORGANISM: Homo sapiens
<220> FEATURE:
<223> OTHER INFORMATION: 13.6 kDa fragment of Apolipoprotein A-I
      (ApoA-I)

<400> SEQUENCE: 18

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence:8.13 kDa
      fragment C-terminal truncation of Complement C3
      anaphylatoxin (C3a) Chagas disease biomarker
      tryptic digest fragment peptide

<400> SEQUENCE: 19

Phe Ile Ser Leu Gly Glu Ala Cys Lys Lys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence:8.13 kDa
      fragment C-terminal truncation of Complement C3
      anaphylatoxin (C3a) Chagas disease biomarker
      tryptic digest fragment peptide

<400> SEQUENCE: 20

Glu Leu Arg Lys Cys Cys Glu Asp Gly Met Arg
1               5                   10

<210> SEQ ID NO 21
<211> LENGTH: 13

```
<212> TYPE: PRT
<213> ORGANISM: Artificial Sequence
<220> FEATURE:
<223> OTHER INFORMATION: Description of Artificial Sequence:8.13 kDa
      fragment C-terminal truncation of Complement C3
      anaphylatoxin (C3a) Chagas disease biomarker
      tryptic digest fragment peptide

<400> SEQUENCE: 21

Val Phe Leu Asp Cys Cys Asn Tyr Ile Thr Glu Leu Arg
 1               5                  10

<210> SEQ ID NO 22
<211> LENGTH: 14
<212> TYPE: PRT
<213> ORGANISM: Artificial Sequence
<220> FEATURE:
<223> OTHER INFORMATION: Description of Artificial Sequence:8.13 kDa
      fragment C-terminal truncation of Complement C3
      anaphylatoxin (C3a) Chagas disease biomarker
      tryptic digest fragment peptide

<400> SEQUENCE: 22

Lys Val Phe Leu Asp Cys Cys Asn Tyr Ile Thr Glu Leu Arg
 1               5                  10

<210> SEQ ID NO 23
<211> LENGTH: 77
<212> TYPE: PRT
<213> ORGANISM: Homo sapiens
<220> FEATURE:
<223> OTHER INFORMATION: 8.13 kDa C-terminal truncation of Complement
      C3 anaphylatoxin

<400> SEQUENCE: 23

Ser Val Gln Leu Thr Glu Lys Arg Met Asp Lys Val Gly Lys Tyr Pro
 1               5                  10                  15

Lys Glu Leu Arg Lys Cys Cys Glu Asp Gly Met Arg Glu Asn Pro Met
             20                  25                  30

Arg Phe Ser Cys Gln Arg Arg Thr Arg Phe Ile Ser Leu Gly Glu Ala
         35                  40                  45

Cys Lys Lys Val Phe Leu Asp Cys Cys Asn Tyr Ile Thr Glu Leu Arg
     50                  55                  60

Arg Gln His Ala Arg Ala Ser His Leu Gly Leu Ala Arg
 65                  70                  75

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence:N-terminal
      28.7 kDa fragment of Fibronectin Chagas disease
      biomarker tryptic digest fragment peptide

<400> SEQUENCE: 24

Gly Asn Leu Leu Gln Cys Ile Cys Thr Gly Asn Gly Arg
 1               5                  10

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence:N-terminal
      28.7 kDa fragment of Fibronectin Chagas disease
      biomarker tryptic digest fragment peptide
```

```
<400> SEQUENCE: 25

His Tyr Gln Ile Asn Gln Gln Trp Glu Arg
 1               5                  10

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence:N-terminal
      28.7 kDa fragment of Fibronectin Chagas disease
      biomarker tryptic digest fragment peptide

<400> SEQUENCE: 26

Asp Ser Met Ile Trp Asp Cys Thr Cys Ile Gly Ala Gly Arg
 1               5                  10

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence:N-terminal
      28.7 kDa fragment of Fibronectin Chagas disease
      biomarker tryptic digest fragment peptide

<400> SEQUENCE: 27

Thr Tyr Leu Gly Asn Ala Leu Val Cys Thr Cys Tyr Gly Gly Ser Arg
 1               5                  10                  15

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence:N-terminal
      28.7 kDa fragment of Fibronectin Chagas disease
      biomarker tryptic digest fragment peptide

<400> SEQUENCE: 28

His Thr Ser Val Gln Thr Thr Ser Ser Gly Ser Gly Pro Phe Thr Asp
 1               5                  10                  15

Val

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence:N-terminal
      28.7 kDa fragment of Fibronectin Chagas disease
      biomarker tryptic digest fragment peptide

<400> SEQUENCE: 29

Ile Ser Cys Thr Ile Ala Asn Arg Cys His Glu Gly Gly Gln Ser Tyr
 1               5                  10                  15

Lys

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence:N-terminal
      28.7 kDa fragment of Fibronectin Chagas disease
      biomarker tryptic digest fragment peptide

<400> SEQUENCE: 30
```

Gly Phe Asn Cys Glu Ser Lys Pro Glu Ala Glu Glu Thr Cys Phe Asp
1               5                   10                  15

Lys Tyr Thr Gly Asn Thr Tyr Arg
            20

<210> SEQ ID NO 31
<211> LENGTH: 300
<212> TYPE: PRT
<213> ORGANISM: Homo sapiens
<220> FEATURE:
<223> OTHER INFORMATION: N-terminal 28.7 fragment of Fibronectin

<400> SEQUENCE: 31

Gln Ala Gln Gln Met Val Gln Pro Gln Ser Pro Val Ala Val Ser Gln
1               5                   10                  15

Ser Lys Pro Gly Cys Tyr Asp Asn Gly Lys His Tyr Gln Ile Asn Gln
            20                  25                  30

Gln Trp Glu Arg Thr Tyr Leu Gly Asn Ala Leu Val Cys Thr Cys Tyr
        35                  40                  45

Gly Gly Ser Arg Gly Phe Asn Cys Glu Ser Lys Pro Glu Ala Glu Glu
    50                  55                  60

Thr Cys Phe Asp Lys Tyr Thr Gly Asn Thr Tyr Arg Val Gly Asp Thr
65                  70                  75                  80

Tyr Glu Arg Pro Lys Asp Ser Met Ile Trp Asp Cys Thr Cys Ile Gly
                85                  90                  95

Ala Gly Arg Gly Arg Ile Ser Cys Thr Ile Ala Asn Arg Cys His Glu
            100                 105                 110

Gly Gly Gln Ser Tyr Lys Ile Gly Asp Thr Trp Arg Arg Pro His Glu
        115                 120                 125

Thr Gly Gly Tyr Met Leu Glu Cys Val Cys Leu Gly Asn Gly Lys Gly
    130                 135                 140

Glu Trp Thr Cys Lys Pro Ile Ala Glu Lys Cys Phe Asp His Ala Ala
145                 150                 155                 160

Gly Thr Ser Tyr Val Val Gly Glu Thr Trp Glu Lys Pro Tyr Gln Gly
                165                 170                 175

Trp Met Met Val Asp Cys Thr Cys Leu Gly Glu Gly Ser Gly Arg Ile
            180                 185                 190

Thr Cys Thr Ser Arg Asn Arg Cys Asn Asp Gln Asp Thr Arg Thr Ser
        195                 200                 205

Tyr Arg Ile Gly Asp Thr Trp Ser Lys Lys Asp Asn Arg Gly Asn Leu
    210                 215                 220

Leu Gln Cys Ile Cys Thr Gly Asn Gly Arg Gly Glu Trp Lys Cys Glu
225                 230                 235                 240

Arg His Thr Ser Val Gln Thr Thr Ser Ser Gly Ser Gly Pro Phe Thr
                245                 250                 255

Asp Val Arg Ala Ala Val Tyr Gln Pro Gln Pro His Pro Gln Pro Pro
            260                 265                 270

Pro Tyr Gly His Cys Val Thr Asp Ser Gly Val Val Tyr Ser Val Gly
        275                 280                 285

Met Gln Trp Leu Lys Thr Gln Gly Asn Lys Gln Met
    290                 295                 300

<210> SEQ ID NO 32
<211> LENGTH: 9
<212> TYPE: PRT
<213> ORGANISM: Artificial Sequence
<220> FEATURE:

```
<223> OTHER INFORMATION: Description of Artificial Sequence:C-terminal
      truncation 24.7 kDa fragment of Apolipoprotein A-I
      (ApoA-I) Chagas disease biomarker tryptic digest
      fragment peptide

<400> SEQUENCE: 32

Leu Ser Pro Leu Gly Glu Glu Met Arg
 1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence:C-terminal
      truncation 24.7 kDa fragment of Apolipoprotein A-I
      (ApoA-I) Chagas disease biomarker tryptic digest
      fragment peptide

<400> SEQUENCE: 33

Asp Glu Pro Pro Gln Ser Pro Trp Asp Arg
 1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence:C-terminal
      truncation 24.7 kDa fragment of Apolipoprotein A-I
      (ApoA-I) Chagas disease biomarker tryptic digest
      fragment peptide

<400> SEQUENCE: 34

Thr His Leu Ala Pro Tyr Ser Asp Glu Leu Arg
 1               5                   10

<210> SEQ ID NO 35
<211> LENGTH: 13
<212> TYPE: PRT
<213> ORGANISM: Artificial Sequence
<220> FEATURE:
<223> OTHER INFORMATION: Description of Artificial Sequence:C-terminal
      truncation 24.7 kDa fragment of Apolipoprotein A-I
      (ApoA-I) Chagas disease biomarker tryptic digest
      fragment peptide

<400> SEQUENCE: 35

Asp Tyr Val Ser Gln Phe Glu Gly Ser Ala Leu Gly Lys
 1               5                   10

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence:C-terminal
      truncation 24.7 kDa fragment of Apolipoprotein A-I
      (ApoA-I) Chagas disease biomarker tryptic digest
      fragment peptide

<400> SEQUENCE: 36

Leu Leu Asp Asn Trp Asp Ser Val Thr Ser Thr Phe Ser Lys
 1               5                   10

<210> SEQ ID NO 37
<211> LENGTH: 15
<212> TYPE: PRT
<213> ORGANISM: Artificial Sequence
<220> FEATURE:
```

```
<223> OTHER INFORMATION: Description of Artificial Sequence:C-terminal
      truncation 24.7 kDa fragment of Apolipoprotein A-I
      (ApoA-I) Chagas disease biomarker tryptic digest
      fragment peptide

<400> SEQUENCE: 37

Gln Lys Val Glu Pro Leu Arg Ala Glu Leu Gln Glu Gly Ala Arg
  1               5                  10                  15

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence:C-terminal
      truncation 24.7 kDa fragment of Apolipoprotein A-I
      (ApoA-I) Chagas disease biomarker tryptic digest
      fragment peptide

<400> SEQUENCE: 38

Asp Ser Gly Arg Asp Tyr Val Ser Gln Phe Glu Gly Ser Ala Leu Gly
  1               5                  10                  15

Lys
```